US008343757B2

(12) United States Patent
Deng et al.

(10) Patent No.: US 8,343,757 B2
(45) Date of Patent: Jan. 1, 2013

(54) POLYNUCLEOTIDES ALLOWING THE EXPRESSION AND SECRETION OF RECOMBINANT PSEUDO-VIRUS CONTAINING FOREIGN EPITOPES, THEIR PRODUCTION, AND USE

(75) Inventors: Qiang Deng, Shanghai (CN); Marie-Louise Michel, Paris (FR)

(73) Assignees: Institut Pasteur, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 13/037,931

(22) Filed: Mar. 1, 2011

(65) Prior Publication Data
US 2011/0243986 A1 Oct. 6, 2011

Related U.S. Application Data

(63) Continuation of application No. 12/209,749, filed on Sep. 12, 2008, now abandoned.

(60) Provisional application No. 60/960,091, filed on Sep. 14, 2007, provisional application No. 61/136,125, filed on Aug. 13, 2008, provisional application No. 61/136,154, filed on Aug. 14, 2008.

(51) Int. Cl.
*C12N 15/00* (2006.01)
*C12N 15/09* (2006.01)

(52) U.S. Cl. .................... 435/320.1; 435/370; 435/91.4; 424/227.1

(58) Field of Classification Search .......................... None
See application file for complete search history.

(56) References Cited

U.S. PATENT DOCUMENTS 5,980,901 A 11/1999 Shih et al.
5,981,274 A 11/1999 Tyrrell et al.

FOREIGN PATENT DOCUMENTS

WO   WO 2009/034182   3/2009

OTHER PUBLICATIONS

NCBI, Hepatitis B virus , Strain ayw genome published Jan. 28, 2003.*
Christman et al., Proc. Natl. Acad. Sci. USA, 1982, vol. 79, pp. 1815-1819.
Yuan et al.,J. Virol. 1998, vol. 72, No. 3, pp. 2163-2167.
Michel et al., Vaccine, Feb. 2007, vol. 25, pp. 1901-1911.
Netter et al., Vaccine, 2003, vol. 21, pp. 2692-2697.
Pumpens et al., (A) Intervirology 2001, vol. 44, pp. 98-114.
Pumpens et al., (B) Intervirology 2002, vol. 45, pp. 24-32.
Dudek et al., Virology 2006, vol. 344 (1)M OO, 230-239.
International Search Report, PCT/EP2008/062208.

* cited by examiner

*Primary Examiner* — Bao Li
(74) *Attorney, Agent, or Firm* — Finnegan, Henderson, Farabow, Garrett & Dunner L.L.P.

(57) ABSTRACT

This invention provides a new approach to the design of a virus with a defective replication cycle, which can be rescued by wild type virus co-infection, and which expresses foreign antigenic epitopes that contribute to the elimination of virus infected cells and then to viral clearance. The vector of the invention, by expression of epitopes derived from common pathogens, by-passes existing tolerance of virus specific T cell responses. The vector will only replicate in virus infected cells.

15 Claims, 18 Drawing Sheets

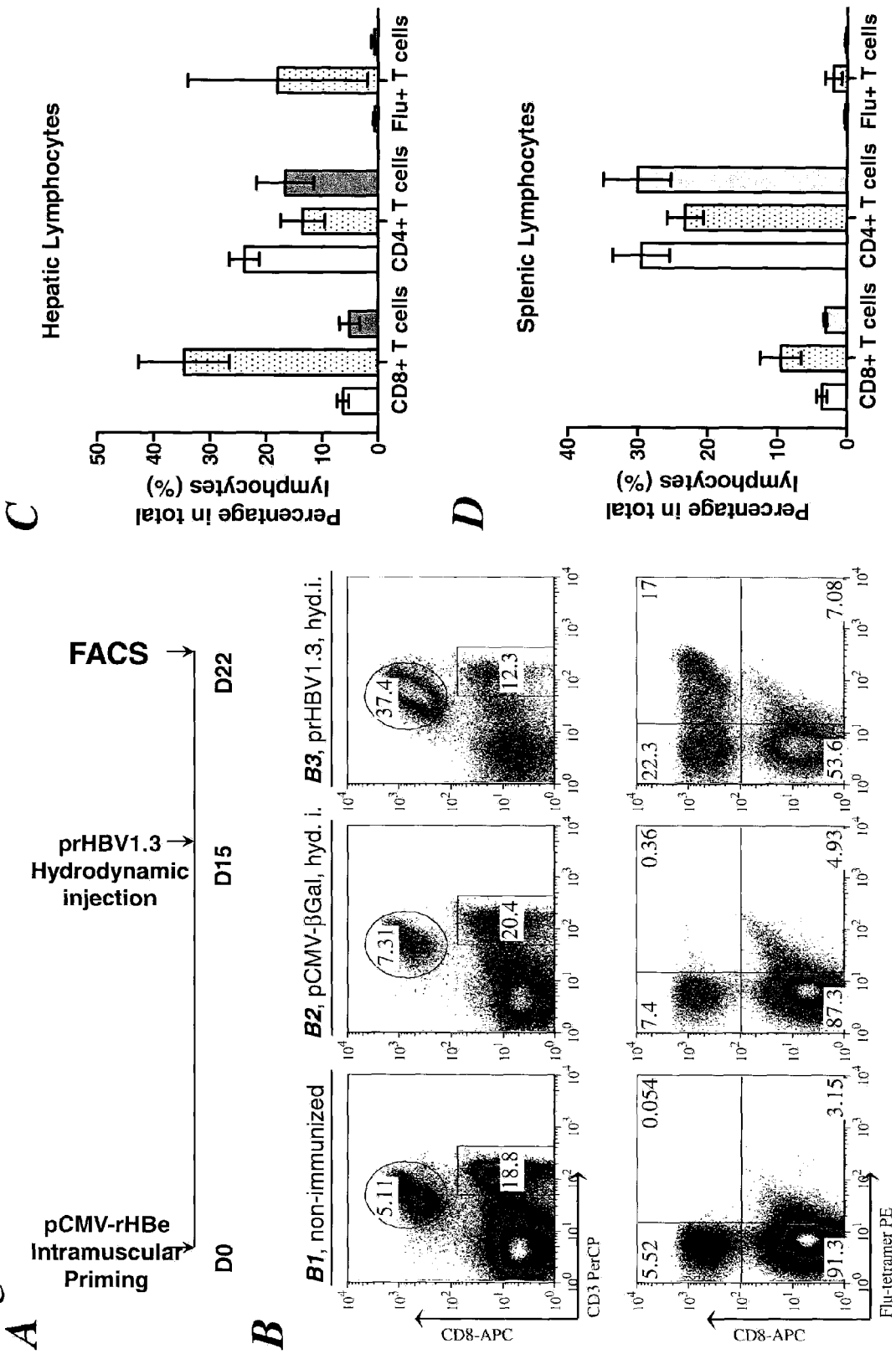

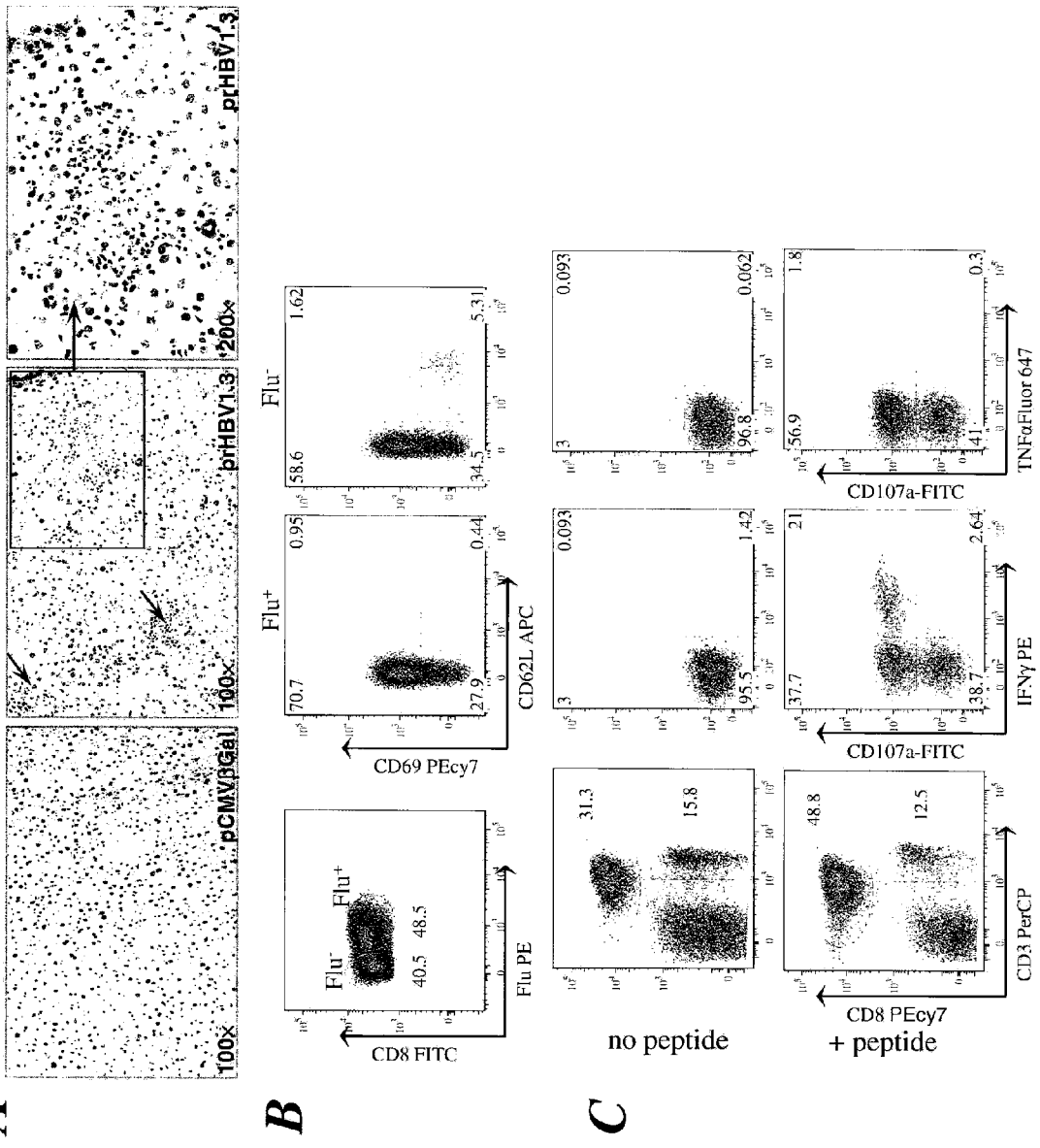
Figure 16 (1)

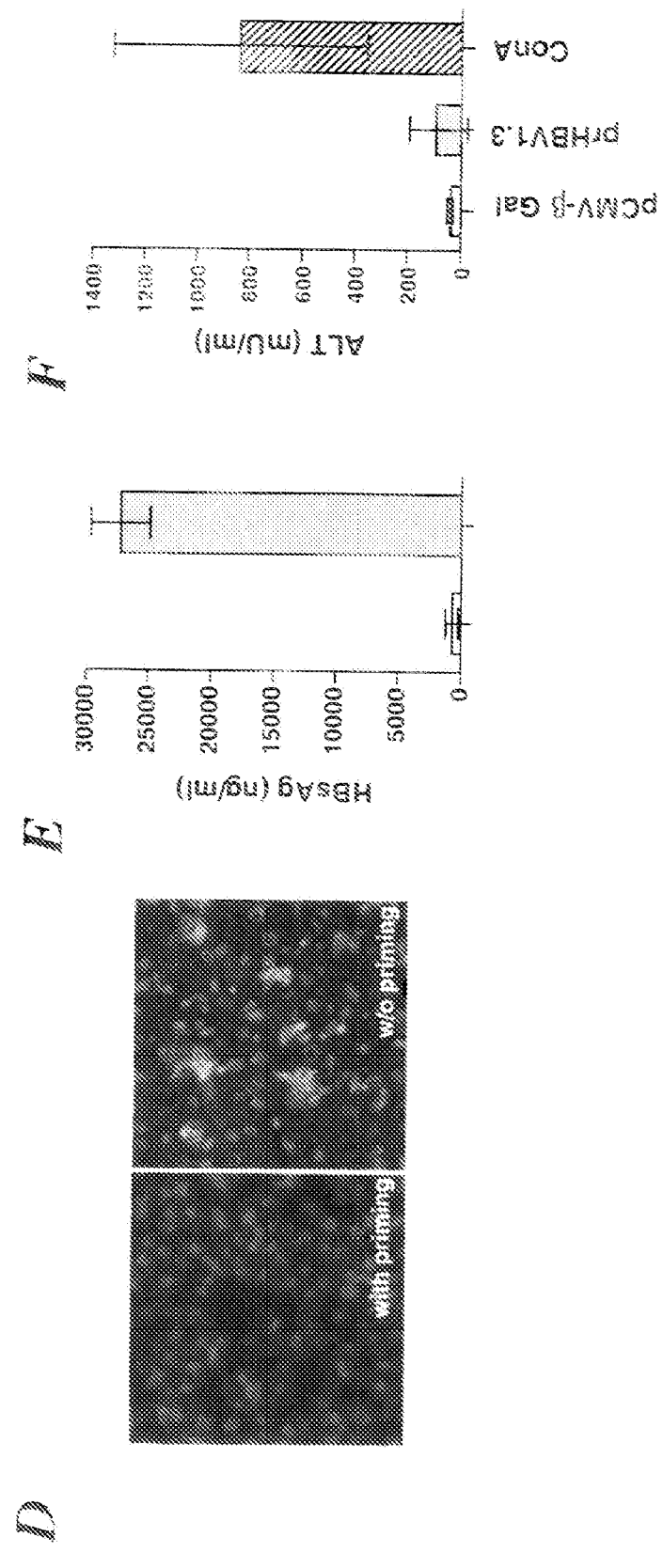
Figure 16 (2)

SEQUENCE LISTING

<160> NUMBER OF SEQ ID NOS: 22

<210> SEQ ID NO 1
<211> LENGTH: 9
<212> TYPE: PRT
<213> ORGANISM: Human immunodeficiency virus 1

<400> SEQUENCE: 1

Ser Leu Tyr Asn Thr Val Ala Thr Leu
1               5

```
<210> SEQ ID NO 2
<211> LENGTH: 8
<212> TYPE: PRT
<213> ORGANISM: Human immunodeficiency virus 1

<400> SEQUENCE: 2

Thr Leu Asn Ala Trp Val Lys Trp
1               5

<210> SEQ ID NO 3
<211> LENGTH: 10
<212> TYPE: PRT
<213> ORGANISM: Human immunodeficiency virus 1

<400> SEQUENCE: 3

Leu Leu Asp Thr Gly Ala Asp Asp Thr Val
1               5                   10

<210> SEQ ID NO 4
<211> LENGTH: 11
<212> TYPE: PRT
<213> ORGANISM: Human immunodeficiency virus 1

<400> SEQUENCE: 4

Val Leu Asp Val Gly Asp Ala Tyr Phe Ser Val
1               5                   10

<210> SEQ ID NO 5
<211> LENGTH: 9
<212> TYPE: PRT
<213> ORGANISM: Human immunodeficiency virus 1

<400> SEQUENCE: 5

Val Ile Tyr Gln Tyr Met Asp Asp Leu
1               5

<210> SEQ ID NO 6
<211> LENGTH: 9
<212> TYPE: PRT
<213> ORGANISM: Human immunodeficiency virus 1

<400> SEQUENCE: 6

Ile Leu Lys Glu Pro Val His Gly Val
1               5

<210> SEQ ID NO 7
<211> LENGTH: 9
<212> TYPE: PRT
<213> ORGANISM: Human immunodeficiency virus 1

<400> SEQUENCE: 7

Pro Leu Val Lys Leu Trp Tyr Gln Leu
1               5

<210> SEQ ID NO 8
<211> LENGTH: 11
<212> TYPE: PRT
<213> ORGANISM: Human immunodeficiency virus 1

<400> SEQUENCE: 8

Glu Ser Glu Leu Val Asn Gln Ile Ile Glu Gln
1               5                   10

<210> SEQ ID NO 9
<211> LENGTH: 10
```

```
<212> TYPE: PRT
<213> ORGANISM: Human immunodeficiency virus 1

<400> SEQUENCE: 9

Glu Leu Val Asn Gln Ile Ile Glu Gln Leu
1               5                   10

<210> SEQ ID NO 10
<211> LENGTH: 9
<212> TYPE: PRT
<213> ORGANISM: Human immunodeficiency virus 1

<400> SEQUENCE: 10

Leu Leu Trp Lys Gly Glu Gly Ala Val
1               5

<210> SEQ ID NO 11
<211> LENGTH: 9
<212> TYPE: PRT
<213> ORGANISM: Human immunodeficiency virus 1

<400> SEQUENCE: 11

Arg Leu Arg Asp Leu Leu Leu Ile Val
1               5

<210> SEQ ID NO 12
<211> LENGTH: 9
<212> TYPE: PRT
<213> ORGANISM: Human immunodeficiency virus 1

<400> SEQUENCE: 12

Ala Phe His His Val Ala Arg Glu Leu
1               5

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgaacatgg ag                                                            12

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtggagccct caggctcagg g                                                  21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggacaaacgg gcaacatacc                                                    20
```

<210> SEQ ID NO 16
<211> LENGTH: 7011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgca | atctaagcag | gctttcactt | tctcgccaac | 240 |
| ttacaaggcc | tttctgtgta | aacaatacct | gaacctttac | cccgttgccc | ggcaacggcc | 300 |
| aggtctgtgc | caagtgtttg | ctgacgcaac | ccccactggc | tggggcttgg | tcatgggcca | 360 |
| tcagcgcatg | cgtggaacct | tttcggctcc | tctgccgatc | catactgcgg | aactcctagc | 420 |
| cgcttgtttt | gctcgcagca | ggtctggagc | aaacattatc | gggactgata | actctgttgt | 480 |
| cctatcccgc | aaatatacat | cgtttccatg | gctgctaggc | tgtgctgcca | actggatcct | 540 |
| gcgcgggacg | tcctttgttt | acgtcccgtc | ggcgctgaat | cctgcggacg | acccttctcg | 600 |
| gggtcgcttg | ggactctctc | gtcccctcct | ccgtctgccg | ttccgaccga | ccacggggcg | 660 |
| cacctctctt | tacgcggact | ccccgtctgt | gccttctcat | ctgccggacc | gtgtgcactt | 720 |
| cgcttcacct | ctgcacgtcg | catggagacc | accgtgaacg | cccaccaaat | attgcccaag | 780 |
| gtcttacata | agaggactct | tggactctca | gcaatgtcaa | cgaccgacct | tgaggcatac | 840 |
| ttcaaagact | gtttgtttaa | agactgggag | gagttggggg | aggagattag | gttaaaggtc | 900 |
| tttgtactag | gaggctgtag | gcataaattg | gtctgcgcac | cagcaccatg | caactttttc | 960 |
| acctctgcct | aatcatctct | tgttcatgtc | ctactgttca | agcctccaag | ctgtgccttg | 1020 |
| ggtggctttg | gggcatggac | atcgaccctt | ataaagaatt | tggagctact | gtggagttac | 1080 |
| tctcgttttt | gccttctgac | ttctttcctt | cagtaagctt | cgactacaag | gacgacgacg | 1140 |
| acaagagcct | gttcaacacc | gtggccaccc | tgtacaccaa | gggcatcctg | ggcttcgtgt | 1200 |
| tcaccctgaa | gaacgccggc | ctgtgcaccc | tggtggccat | gctgggcccc | ggccccggca | 1260 |
| aggccaagtt | cgtggccgcc | tggaccctga | aggctgcagc | cgaacatgga | gcccctatcc | 1320 |
| tatcaacact | tccggagact | actgttgtta | gacgacgagg | caggtcccct | agaagaagaa | 1380 |
| ctccctcgcc | tcgcagacga | aggtctcaat | cgccgcgtcg | cagaagatct | caatctcggg | 1440 |
| aatctcaatg | ttagtattcc | ttggactcat | aaggtgggga | actttactgg | gctttattct | 1500 |
| tctactgtac | ctgtctttaa | tcctcattgg | aaaacaccat | cttttcctaa | tatacattta | 1560 |
| caccaagaca | ttatcaaaaa | atgtgaacag | tttgtaggcc | cactcacagt | taatgagaaa | 1620 |
| agaagattgc | aattgattat | gcctgccagg | ttttatccaa | aggttaccaa | atatttacca | 1680 |
| ttggataagg | gtattaaacc | ttattatcca | gaacatctag | ttaatcatta | cttccaaact | 1740 |
| agacactatt | tacacactct | atggaaggcg | ggtatattat | ataagagaga | aacaacacat | 1800 |
| agcgcctcat | tttgtgggtc | accatattct | tgggaacaag | atctacagca | tggggcagaa | 1860 |
| tctttccacc | agcaatcctc | tgggattctt | tcccgaccac | cagttggatc | cagccttcag | 1920 |
| agcaaacacc | gcaaatccag | attgggactt | caatcccaac | aaggacacct | ggccagacgc | 1980 |
| caacaaggta | ggagctggag | cattcgggct | gggtttcacc | ccaccgcacg | gaggcctttt | 2040 |
| ggggtggagc | cctcaggctc | aggcatact | acaaactttg | ccagcaaatc | cgcctcctgc | 2100 |

```
ctccaccaat cgccagtcag gaaggcagcc taccccgctg tctccacctt tgagaaacac    2160
tcatcctcag gccatgcagt ggaattccac aaccttccac caaactctgc aagatcccag    2220
agtgagaggc ctgtatttcc ctgctggtgg ctccagttca ggaacagtaa accctgttct    2280
gactactgcc tctcccttat cgtcaatctt ctcgaggatt ggggaccctg cgctgaacat    2340
ggagaacatc acatcaggat tcctaggacc ccttctcgtg ttacaggcgg ggttttcttt    2400
gttgacaaga atcctcacaa taccgcagag tctagactcg tggtggactt ctctcaattt    2460
tctaggggga actaccgtgt gtcttggcca aaattcgcag tccccaacct ccaatcactc    2520
accaacctct tgtcctccaa cttgtcctgg ttatcgctgg atgtgtctgc ggcgttttat    2580
catcttcctc ttcatcctgc tgctatgcct catcttcttg ttggttcttc tggactatca    2640
aggtatgttg cccgtttgtc ctctaattcc aggatcctca caaccagca cgggaccatg    2700 ccggacctgc atgactactg ctcaaggaac ctctatgtat ccctcctgtt gctgtaccaa    2760
accttcggac ggaaattgca cctgtattcc catcccatca tcctgggctt tcggaaaatt    2820
cctatgggag tgggcctcag cccgtttctc ctggctcagt ttactagtgc catttgttca    2880
gtggttcgta gggcttttccc ccactgtttg gctttcagtt atatggatga tgtggtattg    2940
ggggccaagt ctgtacagca tcttgagtcc cttttaccg ctgttaccaa ttttcttttg    3000
tctttgggta tacatttaaa ccctaacaaa acaaagagat ggggttactc tctaaatttt    3060
atgggttatg tcattggatg ttatgggtcc ttgccacaag aacacatcat acaaaaaatc    3120
aaagaatgtt ttagaaaact tcctattaac aggcctattg attggaaagt atgtcaacga    3180
attgtgggtc ttttgggttt tgctgcccct tttacacaat gtggttatcc tgcgttgatg    3240
cctttgtatg catgtattca atctaagcag gctttcactt tctcgccaac ttacaaggcc    3300
tttctgtgta acaatacct gaacctttac cccgttgccc ggcaacggcc aggtctgtgc    3360
caagtgtttg ctgacgcaac ccccactggc tggggcttgg tcatgggcca tcagcgcatg    3420
cgtggaacct tttcggctcc tctgccgatc catactgcgg aactcctagc cgcttgtttt    3480
gctcgcagca ggtctggagc aaacattatc gggactgata actctgttgt cctatcccgc    3540
aaatatacat cgtttccatg gctgctaggc tgtgctgcca actggatcct gcgcgggacg    3600
tcctttgttt acgtcccgtc ggcgctgaat cctgcggacg accttctcg gggtcgcttg    3660 ggactctctc gtccccttct ccgtctgccg ttccgaccga ccacggggcg cacctctctt    3720
tacgcggact cccgtctgt gccttctcat ctgccggacc gtgtgcactt cgcttcacct    3780
ctgcacgtcg catggagacc accgtgaacg cccaccaaat attgcccaag gtcttacata    3840
agaggactct tggactctca gcaatgtcaa cgaccgacct tgaggcatac ttcaaagact    3900
gtttgtttaa agactgggag gagttggggg aggagattag gttaaaggtc tttgtactag    3960
gaggctgtag gcataaattg gtctgcgcac cagcaccatg caacttttc acctctgcct    4020 aatcatctct tgttcatgtc ctactgttca agcctccaag ctgtgccttg ggtggctttg    4080
gggcatggac atcgaccctt ataaagaatt tggagctact gtggagttac tctcgttttt    4140
gccttctgac ttctttcctt cagtacgaga tccactagtt ctagagcggc cgccaccgcg    4200
gtggagctcc agcttttgtt cccttttagtg agggttaatt gcgcgcatgc ccgacggcga    4260
ggatctcgtc gtgacccatg gcgatgcctg cttgccgaat atcatggtgg aaaatggccg    4320
cttttctgga ttcatcgact gtggccggct gggtgtggcg gaccgctatc aggacatagc    4380
gttggctacc cgtgatattg ctgaagagct tggcggcgaa tgggctgacc gcttcctcgt    4440
gctttacggt atcgccgctc ccgattcgca gcgcatcgcc ttctatcgcc ttcttgacga    4500
```

```
gttcttctga gcgggactct ggggttcgaa atgaccgacc aagcgacgcc caacctgcca    4560
tcacgagatt tcgattccac cgccgccttc tatgaaaggt tgggcttcgg aatcgttttc    4620
cgggacgccg gctggatgat cctccagcgc ggggatctca tgctggagtt cttcgcccac    4680
cccaacttgt ttattgcagc ttataatggt tacaaataaa gcaatagcat cacaaatttc    4740
acaaataaag catttttttc actgcattct agttgtggtt tgtccaaact catcaatgta    4800
tcttatcatg tctgtatacc gtcgacctct agctagagct tggcgtaatc atggtcatag    4860
ctgtttcctg tgtgaaattg ttatccgctc acaattccac acaacatacg agccggaagc    4920
ataaagtgta aagcctgggg tgcctaatga gtgagctaac tcacattaat tgcgttgcgc    4980
tcactgcccg ctttccagtc gggaaacctg tcgtgccagc tgcattaatg aatcggccaa    5040
cgcgcgggga gaggcggttt gcgtattggg cgctcttccg cttcctcgct cactgactcg    5100
ctgcgctcgg tcgttcggct gcggcgagcg gtatcagctc actcaaaggc ggtaatacgg    5160
ttatccacag aatcagggga taacgcagga agaacatgt gagcaaaagg ccagcaaaag    5220
gccaggaacc gtaaaaaggc cgcgttgctg gcgtttttcc ataggctccg ccccccctgac   5280 gagcatcaca aaaatcgacg ctcaagtcag aggtggcgaa acccgacagg actataaaga    5340
taccaggcgt ttccccctgg aagctccctc gtgcgctctc ctgttccgac cctgccgctt    5400
accggatacc tgtccgcctt tctcccttcg ggaagcgtgg cgctttctca atgctcacgc    5460
tgtaggtatc tcagttcggt gtaggtcgtt cgctccaagc tgggctgtgt gcacgaaccc    5520
cccgttcagc ccgaccgctg cgccttatcc ggtaactatc gtcttgagtc aacccggta    5580 agacacgact tatcgccact ggcagcagcc actggtaaca ggattagcag agcgaggtat    5640
gtaggcggtg ctacagagtt cttgaagtgg tggcctaact acggctacac tagaaggaca    5700
gtatttggta tctgcgctct gctgaagcca gttaccttcg gaaaaagagt tggtagctct    5760
tgatccggca acaaaccac cgctggtagc ggtggttttt ttgtttgcaa gcagcagatt    5820
acgcgcagaa aaaaaggatc tcaagaagat cctttgatct tttctacggg gtctgacgct    5880
cagtggaacg aaaactcacg ttaagggatt ttggtcatga gattatcaaa aaggatcttc    5940
acctagatcc ttttaaatta aaaatgaagt tttaaatcaa tctaaagtat atatgagtaa    6000
acttggtctg acagttacca atgcttaatc agtgaggcac ctatctcagc gatctgtcta    6060
tttcgttcat ccatagttgc ctgactcccc gtcgtgtaga taactacgat acgggagggc    6120
ttaccatctg gccccagtgc tgcaatgata ccgcgagacc cacgctcacc ggctccagat    6180
ttatcagcaa taaaccagcc agccggaagg gccgagcgca gaagtggtcc tgcaacttta    6240
tccgcctcca tccagtctat taattgttgc cgggaagcta gagtaagtag ttcgccagtt    6300
aatagtttgc gcaacgttgt tgccattgct acaggcatcg tggtgtcacg ctcgtcgttt    6360
ggtatggctt cattcagctc cggttcccaa cgatcaaggc gagttacatg atcccccatg    6420
ttgtgcaaaa aagcggttag ctccttcggt cctccgatcg ttgtcagaag taagttggcc    6480
gcagtgttat cactcatggt tatggcagca ctgcataatt ctcttactgt catgccatcc    6540
gtaagatgct tttctgtgac tggtgagtac tcaaccaagt cattctgaga atagtgtatg    6600
cggcgaccga gttgctcttg cccggcgtca atacgggata ataccgcgcc acatagcaga    6660
actttaaaag tgctcatcat tggaaaacgt tcttcggggc gaaaactctc aaggatctta    6720
ccgctgttga gatccagttc gatgtaaccc actcgtgcac ccaactgatc ttcagcatct    6780
tttactttca ccagcgtttc tgggtgagca aaaacaggaa ggcaaaatgc cgcaaaaaag    6840
ggaataaggg cgacacggaa atgttgaata ctcatactct tcctttttca atattattga    6900
```

```
agcatttatc agggttattg tctcatgagc ggatacatat ttgaatgtat ttagaaaaat    6960
aaacaaatag gggttccgcg cacatttccc cgaaaagtgc cacctgacgt c            7011
```

<210> SEQ ID NO 17
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Ile Asp Pro Tyr Lys Glu Phe Gly Ala Thr Val Glu Leu Leu
1               5                   10                  15

Ser Phe Leu Pro Ser Asp Phe Pro Ser Val Ser Phe Asp Tyr Lys
                20                  25                  30

Asp Asp Asp Asp Lys Ser Leu Phe Asn Thr Val Ala Thr Leu Tyr Thr
            35                  40                  45

Lys Gly Ile Leu Gly Phe Val Phe Thr Leu Lys Asn Ala Gly Leu Cys
    50                  55                  60

Thr Leu Val Ala Met Leu Gly Pro Gly Pro Lys Ala Lys Phe Val
65                  70                  75                  80

Ala Ala Trp Thr Leu Lys Ala Ala Glu His Gly Ala Pro Ile Leu
                85                  90                  95

Ser Thr Leu Pro Glu Thr Thr Val Val Arg Arg Arg Gly Arg Ser Pro
            100                 105                 110

Arg Arg Arg Thr Pro Ser Pro Arg Arg Arg Ser Gln Ser Pro Arg
        115                 120                 125

Arg Arg Arg Ser Gln Ser Arg Glu Ser Gln Cys
    130                 135

<210> SEQ ID NO 18
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Tyr Lys Asp Asp Asp Asp Lys Ser Leu Phe Asn Thr Val Ala Thr
1               5                   10                  15

Leu Tyr Thr Lys Gly Ile Leu Gly Phe Val Phe Thr Leu Lys Asn Ala
                20                  25                  30

Gly Leu Cys Thr Leu Val Ala Met Leu Gly Pro Gly Pro Lys Ala
            35                  40                  45

Lys Phe Val Ala Ala Trp Thr Leu Lys Ala Ala Ala
    50                  55                  60

<210> SEQ ID NO 19
<211> LENGTH: 63
<212> TYPE: PRT
<213> ORGANISM: Hepatitis B virus

<400> SEQUENCE: 19

Asp Tyr Lys Asp Asp Asp Asp Lys Glu Leu Arg Ser Leu Tyr Asn Thr
1               5                   10                  15

Val Ala Thr Leu Tyr Thr Lys Gly Ile Leu Gly Phe Val Phe Thr Leu
                20                  25                  30

| Lys | Asn | Ala | Gly | Leu | Cys | Thr | Leu | Val | Ala | Met | Leu | Gly | Pro | Gly | Pro |
|---|---|---|---|---|---|---|---|---|---|---|---|---|---|---|---|
| | | | 35 | | | | 40 | | | | 45 | | | | |

| Gly | Lys | Ala | Lys | Phe | Val | Ala | Ala | Trp | Thr | Leu | Lys | Ala | Ala | Ala |
|---|---|---|---|---|---|---|---|---|---|---|---|---|---|---|
| 50 | | | | | 55 | | | | | 60 | | | | |

<210> SEQ ID NO 20
<211> LENGTH: 7020
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgca atctaagcag gctttcactt tctcgccaac    240
ttacaaggcc tttctgtgta acaatacct gaacctttac cccgttgccc ggcaacggcc    300
aggtctgtgc caagtgtttg ctgacgcaac ccccactggc tggggcttgg tcatgggcca    360
tcagcgcatg cgtggaacct tttcggctcc tctgccgatc catactgcgg aactcctagc    420
cgcttgtttt gctcgcagca ggtctggagc aaacattatc gggactgata actctgttgt    480
cctatcccgc aaatatacat cgtttccatg gctgctaggc tgtgctgcca actggatcct    540
gcgcgggacg tcctttgttt acgtcccgtc ggcgctgaat cctgcggacg acccttctcg    600
gggtcgcttg ggactctctc gtccccttct ccgtctgccg ttccgaccga ccacggggcg    660
cacctctctt tacgcggact ccccgtctgt gccttctcat ctgccggacc gtgtgcactt    720
cgcttcacct ctgcacgtcg catggagacc accgtgaacg cccaccaaat attgcccaag    780
gtcttacata agaggactct tggactctca gcaatgtcaa cgaccgacct tgaggcatac    840
ttcaaagact gtttgtttaa agactgggag gagttggggg aggagattag gttaaaggtc    900
tttgtactag gaggctgtag gcataaattg gtctgcgcac cagcaccatg caactttttc    960
acctctgcct aatcatctct tgttcatgtc ctactgttca agcctccaag ctgtgccttg   1020
ggtggctttg gggcatggac atcgacccctt ataagaatt tggagctact gtggagttac   1080
tctcgttttt gccttctgac ttctttcctt cagtaagctt cgactacaag gacgacgacg   1140
acaaggaact aagaagcctg tacaacaccg tggccaccct gtacaccaag ggcatcctgg   1200
gcttcgtgtt caccctgaag aacgccggcc tgtgcaccct ggtggccatg ctgggccccg   1260
gcccccggcaa ggccaagttc gtggccgcct ggaccctgaa ggctgcagcc gaacatggag   1320
cccctatcct atcaacactt ccggagacta ctgttgttag acgacgaggc aggtcccta    1380
gaagaagaac tccctcgcct cgcagacgaa ggtctcaatc gccgcgtcgc agaagatctc    1440
aatctcggga atctcaatgt tagtattcct tggactcata aggtggggaa ctttactggg    1500
ctttattctt ctactgtacc tgtctttaat cctcattgga aaacaccatc ttttcctaat    1560
atacatttac accaagacat tatcaaaaaa tgtgaacagt tgtaggccc actcacagtt    1620
aatgagaaaa gaagattgca attgattatg cctgccaggt tttatccaaa ggttaccaaa    1680
tatttaccat tggataaggg tattaaacct tattatccag aacatctagt taatcattac    1740
ttccaaacta gacactattt acacactcta tggaaggcgg gtatattata agagagaa    1800
acaacacata gcgcctcatt ttgtgggtca ccatattctt gggaacaaga tctacagcat    1860
ggggcagaat cttccacca gcaatcctct gggattcttt ccgaccacc agttggatcc    1920
```

```
agccttcaga gcaaacaccg caaatccaga ttgggacttc aatcccaaca aggacacctg    1980
gccagacgcc aacaaggtag gagctggagc attcgggctg ggtttcaccc caccgcacgg    2040
aggccttttg gggtggagcc ctcaggctca gggcatacta caaactttgc cagcaaatcc    2100
gcctcctgcc tccaccaatc gccagtcagg aaggcagcct accccgctgt ctccacettt    2160 gagaaacact catcctcagg ccatgcagtg gaattccaca accttccacc aaactctgca    2220
agatcccaga gtgagaggcc tgtatttccc tgctggtggc tccagttcag gaacagtaaa    2280
ccctgttctg actactgcct ctcccttatc gtcaatcttc tcgaggattg ggaccctgc    2340 gctgaacatg gagaacatca catcaggatt cctaggaccc cttctcgtgt tacaggcggg    2400
gttttctctg ttgacaagaa tcctcacaat accgcagagt ctagactcgt ggtggacttc    2460
tctcaatttt ctaggggaa ctaccgtgtg tcttggccaa aattcgcagt ccccaacctc    2520
caatcactca ccaacctctt gtcctccaac ttgtcctggt tatcgctgga gtgtctgcg    2580 gcgttttatc atcttcctct tcatcctgct gctatgcctc atcttcttgt tggttcttct    2640
ggactatcaa ggtatgttgc ccgtttgtcc tctaattcca ggatcctcaa caaccagcac    2700
gggaccatgc cggacctgca tgactactgc tcaaggaacc tctatgtatc cctcctgttg    2760
ctgtaccaaa ccttcggacg gaaattgcac ctgtattccc atcccatcat cctgggcttt    2820
cggaaaattc ctatgggagt gggcctcagc ccgtttctcc tggctcagtt tactagtgcc    2880
atttgttcag tggttcgtag ggcttttcccc cactgtttgg ctttcagtta tatggatgat    2940
gtggtattgg gggccaagtc tgtacagcat cttgagtccc tttttaccgc tgttaccaat    3000 tttctttgt ctttgggtat acatttaaac cctaacaaaa caaagagatg gggttactct    3060
ctaaatttta tggggttatgt cattggatgt tatgggtcct tgccacaaga acacatcata    3120
caaaaaatca aagaatgttt tagaaaactt cctattaaca ggcctattga ttggaaagta    3180
tgtcaacgaa ttgtgggtct ttttgggtttt gctgccccctt ttacacaatg tggttatcct    3240
gcgttgatgc ctttgtatgc atgtattcaa tctaagcagg ctttcactttt ctcgccaact    3300 tacaaggcct ttctgtgtaa acaatacctg aacctttacc ccgttgcccg gcaacggcca    3360
ggtctgtgcc aagtgtttgc tgacgcaacc cccactggct ggggcttggt catgggccat    3420
cagcgcatgc gtggaacctt ttcggctcct ctgccgatcc atactgcgga actcctagcc    3480
gcttgttttg ctcgcagcag gtctggagca aacattatcg ggactgataa ctctgttgtc    3540
ctatcccgca aatatacatc gtttccatgg ctgctaggct gtgctgccaa ctggatcctg    3600
cgcgggacgt cctttgtta cgtcccgtcg gcgctgaatc ctgcggacga cccttctcgg    3660
ggtcgcttgg gactctctcg tccccttctc cgtctgccgt tccgaccgac cacggggcgc    3720
acctctcttt acgcggactc cccgtctgtg ccttctcatc tgccggaccg tgtgcacttc    3780
gcttcacctc tgcacgtcgc atggagacca ccgtgaacgc ccaccaaata ttgcccaagg    3840
tcttacataa gaggactctt ggactctcag caatgtcaac gaccgacctt gaggcatact    3900
tcaaagactg tttgtttaaa gactgggagg agttggggga ggagattagg ttaaaggtct    3960
ttgtactagg aggctgtagg cataaattgg tctgcgcacc agcaccatgc aacttttca    4020 cctctgccta atcatctctt gttcatgtcc tactgttcaa gcctccaagc tgtgccttgg    4080
gtggctttgg ggcatggaca tcgaccctta taaagaattt ggagctactg tggagttact    4140
ctcgtttttg ccttctgact tctttccttc agtacgagat ccactagttc tagagcggcc    4200
gccaccgcgt tggagctcca gcttttgttc cctttagtga gggttaattg cgcgcatgcc    4260
cgacggcgag gatctcgtcg tgacccatgg cgatgcctgc ttgccgaata tcatggtgga    4320
```

```
aaatggccgc ttttctggat tcatcgactg tggccggctg ggtgtggcgg accgctatca   4380
ggacatagcg ttggctaccc gtgatattgc tgaagagctt ggcggcgaat gggctgaccg   4440
cttcctcgtg ctttacggta tcgccgctcc cgattcgcag cgcatcgcct tctatcgcct   4500
tcttgacgag ttcttctgag cgggactctg gggttcgaaa tgaccgacca agcgacgccc   4560
aacctgccat cacgagattt cgattccacc gccgccttct atgaaaggtt gggcttcgga   4620
atcgttttcc gggacgccgg ctggatgatc ctccagcgcg gggatctcat gctggagttc   4680
ttcgcccacc ccaacttgtt tattgcagct tataatggtt acaaataaag caatagcatc   4740
acaaatttca caaataaagc atttttttca ctgcattcta gttgtggttt gtccaaactc   4800
atcaatgtat cttatcatgt ctgtataccg tcgacctcta gctagagctt ggcgtaatca   4860
tggtcatagc tgtttcctgt gtgaaattgt tatccgctca caattccaca acatacga    4920 gccggaagca taaagtgtaa agcctggggt gcctaatgag tgagctaact cacattaatt   4980
gcgttgcgct cactgcccgc tttccagtcg ggaaacctgt cgtgccagct gcattaatga   5040
atcggccaac gcgcggggag aggcggtttg cgtattgggc gctcttccgc ttcctcgctc   5100
actgactcgc tgcgctcggt cgttcggctg cggcgagcgg tatcagctca ctcaaaggcg   5160
gtaatacggt tatccacaga atcaggggat aacgcaggaa agaacatgtg agcaaaaggc   5220
cagcaaaagg ccaggaaccg taaaaaggcc gcgttgctgg cgtttttcca taggctccgc   5280 cccccctgacg agcatcacaa aaatcgacgc tcaagtcaga ggtggcgaaa cccgacagga   5340
ctataaagat accaggcgtt tcccctggaa gctccctcg tgcgctctcc tgttccgacc   5400
ctgccgctta ccggatacct gtccgccttt ctcccttcgg aagcgtggc gctttctcaa   5460 tgctcacgct gtaggtatct cagttcggtg taggtcgttc gctccaagct gggctgtgtg   5520
cacgaacccc ccgttcagcc cgaccgctgc gccttatccg gtaactatcg tcttgagtcc   5580
aacccggtaa gacacgactt atcgccactg gcagcagcca ctggtaacag gattagcaga   5640
gcgaggtatg taggcggtgc tacagagttc ttgaagtggt ggcctaacta cggctacact   5700
agaaggacag tatttggtat ctgcgctctg ctgaagccag ttaccttcgg aaaaagagtt   5760
ggtagctctt gatccggcaa acaaaccacc gctggtagcg tggtttttt tgtttgcaag   5820 cagcagatta cgcgcagaaa aaaaggatct caagaagatc ctttgatctt ttctacgggg   5880
tctgacgctc agtggaacga aaactcacgt taagggattt tggtcatgag attatcaaaa   5940
aggatcttca cctagatcct tttaaattaa aaatgaagtt ttaaatcaat ctaaagtata   6000
tatgagtaaa cttggtctga cagttaccaa tgcttaatca gtgaggcacc tatctcagcg   6060
atctgtctat ttcgttcatc catagttgcc tgactcccg tcgtgtagat aactacgata   6120
cgggagggct taccatctgg ccccagtgct gcaatgatac gcgagaccc acgctcaccg   6180 gctccagatt tatcagcaat aaaccagcca gccggaaggg ccgagcgcag aagtggtcct   6240
gcaactttat ccgcctccat ccagtctatt aattgttgcc gggaagctag agtaagtagt   6300
tcgccagtta atagtttgcg caacgttgtt gccattgcta caggcatcgt ggtgtcacgc   6360
tcgtcgtttg gtatggcttc attcagctcc ggttcccaac gatcaaggcg agttacatga   6420
tcccccatgt tgtgcaaaaa agcggttagc tccttcggtc ctccgatcgt tgtcagaagt   6480
aagttggccg cagtgttatc actcatggtt atggcagcac tgcataattc tcttactgtc   6540
atgccatccg taagatgctt ttctgtgact ggtgagtact caaccaagtc attctgagaa   6600
tagtgtatgc ggcgaccgag ttgctcttgc ccggcgtcaa tacgggataa taccgcgcca   6660
catagcagaa ctttaaaagt gctcatcatt ggaaaacgtt cttcggggcg aaaactctca   6720
```

```
aggatcttac cgctgttgag atccagttcg atgtaaccca ctcgtgcacc caactgatct      6780
tcagcatctt ttactttcac cagcgtttct gggtgagcaa aaacaggaag gcaaaatgcc      6840
gcaaaaaagg gaataagggc gacacggaaa tgttgaatac tcatactctt ccttttcaa      6900 tattattgaa gcatttatca gggttattgt ctcatgagcg gatacatatt tgaatgtatt      6960
tagaaaaata aacaaatagg ggttccgcgc acatttcccc gaaaagtgcc acctgacgtc      7020
```

<210> SEQ ID NO 21
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Ser Phe Asp Tyr Lys
            20                  25                  30

Asp Asp Asp Asp Lys Glu Leu Arg Ser Leu Tyr Asn Thr Val Ala Thr
        35                  40                  45

Leu Tyr Thr Lys Gly Ile Leu Gly Phe Val Phe Thr Leu Lys Asn Ala
    50                  55                  60

Gly Leu Cys Thr Leu Val Ala Met Leu Gly Pro Gly Pro Lys Ala
65                  70                  75                  80

Lys Phe Val Ala Ala Trp Thr Leu Lys Ala Ala Ala Glu His Gly Ala
                85                  90                  95

Pro Ile Leu Ser Thr Leu Pro Glu Thr Thr Val Val Arg Arg Arg Gly
            100                 105                 110

Arg Ser Pro Arg Arg Arg Thr Pro Ser Pro Arg Arg Arg Ser Gln
        115                 120                 125

Ser Pro Arg Arg Arg Arg Ser Gln Ser Arg Glu Ser Gln Cys
    130                 135                 140
```

<210> SEQ ID NO 22
<211> LENGTH: 3182
<212> TYPE: DNA
<213> ORGANISM: Hepatitis B virus

<400> SEQUENCE: 22

```
aattccactg catggcctga ggatgagtgt ttctcaaagg tggagacagc ggggtaggct       60
gccttcctga ctggcgattg gtggaggcag gaggcggatt tgctggcaaa gtttgtagta      120
tgccctgagc ctgagggctc caccccaaaa ggcctccgtg cggtggggtg aaacccagcc      180
cgaatgctcc agctcctacc tgttggcgt ctggccaggt gtccttgttg ggattgaagt      240
cccaatctgg atttgcggtg tttgctctga aggctggatc caactggtgg tcggaaaga      300 atcccagagg attgctggtg gaaagattct gccccatgct gtagatcttg ttcccaagaa      360
tatggtgacc cacaaaatga ggcgctatgt gttgtttctc tcttatataa atacccgcc      420 ttccatagag tgtgtaaata gtgtctagtt tggaagtaat gattaactag atgttctgga      480
taataaggtt taatacccct atccaatggt aaatatttgg taacctttgg ataaaacctg      540
gcaggcataa tcaattgcaa tcttcttttc tcattaactg tgagtgggcc tacaaactgt      600 tcacatttt tgataatgtc ttggtgtaaa tgtatattag gaaagatgg tgttttccaa      660 tgaggattaa agacaggtac agtagaagaa taaagcccag taaagttccc caccttatga      720
```

```
gtccaaggaa tactaacatt gagattcccg agattgagat cttctgcgac gcggcgattg      780
agaccttcgt ctgcgaggcg agggagttct tcttctaggg gacctgcctc gtcgtctaac      840
aacagtagtc tccggaagtg ttgataggat aggggcattt ggtggtctat aagctggagg      900
agtgcgaatc cacactccga aagacaccaa atactctata actgtttctc ttccaaaagt      960
gagacaagaa atgtgaaacc acaagagttg cctgaacttt aggcccatat tagtgttgac     1020
ataactgact actaggtctc tagacgctgg atcttccaaa ttaacaccca cccaggtagc     1080
tagagtcatt agttcccccc agcaaagaat tgcttgcctg agtgcagtat ggtgaggtga     1140
acaatgctca ggagactcta aggcttcccg atacagagct gaggcggtat ctagaagatc     1200
tcgtactgaa ggaaagaagt cagaaggcaa aaacgagagt aactccacag tagctccaaa     1260
ttctttataa gggtcgatgt ccatgcccca aagccaccca aggcacagct tggaggcttg     1320
aacagtagga catgaacaag atgattag gcagaggtga aaaagttgca tggtgctggt      1380
gcgcagacca atttatgcct acagcctcct agtacaaaga cctttaacct aatctcctcc     1440
cccaactcct cccagtcttt aaacaaacag tctttgaagt atgcctcaag gtcggtcgtt     1500
gacattgctg agagtccaag agtcctctta tgtaagacct tgggcaatat ttggtgggcg     1560
ttcacggtgg tctccatgcg acgtgcagag gtgaagcgaa gtgcacacgg tccggcagat     1620
gagaaggcac agacggggag tccgcgtaaa gagaggtgcg ccccgtggtc ggtcggaacg     1680
gcagacggag aaggggacga gagagtccca agcgaccccg agaagggtcg tccgcaggat     1740
tcagcgccga cgggacgtaa acaaaggacg tcccgcgcag gatccagttg gcagcacagc     1800
ctagcagcca tggaaacgat gtatatttgc gggataggac aacagagtta tcagtcccga     1860
taatgtttgc tccagacctg ctgcgagcaa acaagcggc taggagttcc gcagtatgga      1920
tcggcagagg agccgaaaag gttccacgca tgcgctgatg gcccatgacc aagccccagc     1980
cagtgggggt tgcgtcagca aacacttggc acagacctgg ccgttgccgg gcaacggggt     2040
aaaggttcag gtattgttta cacagaaagg ccttgtaagt tggcgagaaa gtgaaagcct     2100
gcttagattg aatacatgca tacaaaggca tcaacgcagg ataaccacat tgtgtaaaag     2160
gggcagcaaa acccaaaaga cccacaattc gttgacatac tttccaatca ataggcctgt     2220
taataggaag ttttctaaaa cattctttga tttttttgtat gatgtgttct tgtggcaagg     2280
acccataaca tccaatgaca taaccccataa aatttagaga gtaaccccat ctctttgttt     2340
tgttagggtt taaatgtata cccaaagaca aagaaaatt ggtaacagcg gtaaaaaggg      2400
actcaagatg ctgtacagac ttggccccca ataccacatc atccatataa ctgaaagcca     2460
aacagtgggg gaaagcccta cgaaccactg aacaaatggc actagtaaac tgagccagga     2520
gaaacgggct gaggcccact cccataggaa ttttccgaaa gcccaggatg atgggatggg     2580
aatacaggtg caatttccgt ccgaaggttt ggtacagcaa caggagggat acatagaggt     2640
tccttgagca gtagtcatgc aggtccggca tggtcccgtg ctggttgttg aggatcctgg     2700
aattagagga caaacgggca acataccttg atagtccaga agaaccaaca agaagatgag     2760
gcatagcagc aggatgaaga ggaagatgat aaaacgccgc agacacatcc agcgataacc     2820
aggacaagtt ggaggacaag aggttggtga gtgattggag gttggggact gcgaattttg     2880
gccaagacac acggtagttc cccctagaaa attgagagaa gtccaccacg agtctagact     2940
ctgcggtatt gtgaggattc ttgtcaacaa gaaaacccc gcctgtaaca cgagaagggg      3000
tcctaggaat cctgatgtga tgttctccat gttcagcgca gggtcccaa tcctcgagaa      3060 gattgacgat aagggagagg cagtagtcag aacagggttt actgttcctg aactggagcc     3120
```

-continued

```
accagcaggg aaatacaggc ctctcactct gggatcttgc agagtttggt ggaaggttgt   3180
gg                                                                  3182
```

POLYNUCLEOTIDES ALLOWING THE EXPRESSION AND SECRETION OF RECOMBINANT PSEUDO-VIRUS CONTAINING FOREIGN EPITOPES, THEIR PRODUCTION, AND USE

RELATED APPLICATIONS

This is a continuation of application Ser. No. 12/209,749, filed Sep. 12, 2008, which is based on applications 60/960,091, filed Sep. 14, 2007; 61/136,125, filed Aug. 13, 2008; and 61/136,154, filed Aug. 14, 2008, all of which are incorporated by reference in their entireties.

FIELD OF THE INVENTION

This invention relates to polynucleotides for the expression of a recombinant, replication defective virus involved in a persistent infection, and to a recombinant, replication competent pseudo-virus, comprising the recombinant replication defective virus, and to the production of the viruses in host cells. The recombinant, replication defective virus and the replication competent pseudo-virus can contain a foreign epitope or epitopes, such as foreign amino acid residues of a pathogen. The replication defective virus and the replication competent pseudo-virus are particularly useful in immunogenic compositions and as therapeutic vaccines. This invention also relates to T cell responses to viral infection and to recombinant viruses that deliver foreign antigenic epitopes to the liver and induce epitope-specific immune responses.

BACKGROUND OF THE INVENTION

An effective vaccine against hepatitis B virus (HBV) infection has been available for more than two decades, but 400 million people—more than 5% of the world's population—are chronically infected with HBV. More than 1 million people die each year from HBV-related liver cirrhosis and hepatocellular carcinoma. (Ganem, D., Prince, A. M. (2004) Hepatitis B virus infection—natural history and clinical consequences, *N Engl J Med* 350:1118-29.)

HBV is mainly not directly cytopathic. The immune response to viral antigens is thought to be responsible for both liver disease and viral clearance following HBV infection. (Ganem et al., 2004.) Immune responses with virus-specific $CD8^+$ cytotoxic T lymphocytes (CTLs) and $CD4^+$ T-helper (Th) cells play key effector and regulatory roles in both liver pathogenesis and viral clearance. HBV acute infection in immunocompetent adults usually results in a transient self-limited liver disease followed by viral clearance, and is characterized by vigorous polyclonal CTLs and type 1-Th responses specific for a number of epitopes within HBV viral proteins.

Patients with acute viral infection, who successfully clear the virus, display a multispecific polyclonal cytotoxic T-lymphocyte (CTL) response specific for a number of epitopes within the core, polymerase, and envelope proteins. Viral specific, e.g., HBV-specific Th cells are also activated. Multispecific Th1-like responses have been detected in patients successfully clearing HBV after acute infection. (Chisari et al. (1995) Hepatitis B virus immunopathogenesis, *Annu Rev Immunol* 13:29-60.)

The HBV-specific T-cell response is weak or undetectable in patients who develop chronic infection and the mechanisms responsible for T cell hypo-responsiveness or tolerance in chronic infection are not completely understood. In chronically infected patients, the peripheral $CD8^+$ T cell response is undetectable or weak and the $CD4^+$ T cell response is much less vigorous than in patients who clear the infection.

Although functional effector T cells are initially generated during the early stages of infection, they gradually lose function during the course of a chronic infection by upregulating the programmed death 1 (PD-1) inhibitory receptor. (Chisari, et al., 1995.) Accordingly, in chronic patients who spontaneously clear hepatitis B surface antigen (HBsAg) and develop neutralizing anti-HBs antibodies, HBV-specific T-cell responses have been detected in the blood just before seroconversion. It has also been shown that effective therapeutic reduction of HBV viral load resulted in a transient restoration of HBV-specific $CD4^+$ and $CD8^+$ T-cell responses in the blood from patients with chronic hepatitis B.

The mechanisms responsible for T cell hypo-responsiveness and exhaustion during HBV persistent infection are still not completely understood. (Rehermann, B., Nascimbeni M. (2005) Immunology of hepatitis B virus and hepatitis C virus infection, *Nat Rev Immunol* 5:215-29.) Exhausted T cell responses observed during persistent viral infection reflect a balance between effector functions required to eliminate the pathogen and the potential of T cells to cause immunopathology. Impaired dendritic cell functions and the presence of $CD4^+CD25^+$ regulatory T cells also contribute to the viral persistence. Moreover, the liver particularly biases the intrahepatic T cell response towards tolerance or anergy.

Active immunotherapy based on specific viral-epitopes and hepatitis vaccine injection provide promising approaches in inducing efficient cellular immune responses. A previous study of a phase I clinical trial suggested that HBV DNA vaccination could specifically restore T-cell responsiveness in chronic HBV carriers. However, the activation of HBV-specific T-cells appeared to be transient and was followed by a progressive decline along the DNA injections. (Mancini-Bourgine, M., Fontaine, H., Scott-Algara, D., Pol, S., Brechot, C., Michel, M. L. (2004) Induction or expansion of T-cell responses by a hepatitis B DNA vaccine administered to chronic HBV carriers, *Hepatology* 40:874-82.) Bypassing the potential tolerance of T cells to HBV antigens, therefore, turns out to be a most crucial point in immunotherapy.

Collectively this suggests that, to treat chronic hepatitis, e.g., HBV, infection, the intrahepatic T cell responses should be switched from a state of exhaustion or anergy to a state in which the effector T cells are fully efficient. (Bertoletti, A., Gehring, A. J. (2006) The immune response during hepatitis B virus infection, *J Gen Virol* 87:1439-49; Rehermann et al., 2005.)

Accordingly, there exists a need in the art for new therapies for the treatment of chronic hepatitis infection, for example, hepatitis B infection. These therapies should also be generally useful in the treatment of other viral persistent infections. The therapies should also be specific for the cells infected with the virus involved in the persistent infection. For example, in the case of a hepatitis viral infection, the therapies should be specific for hepatitis virus infected cells, especially human hepatocytes. (Rehermann, et al., 2005.)

SUMMARY OF THE INVENTION

This invention aids in fulfilling these needs in the art. To achieve these results, this invention provides a recombinant, replication defective virus that co-maintains in vivo with wild type virus in cells infected with said virus, and that immunologically contributes, after complementation, to virus clearance by expressing foreign antigenic epitopes in virus infected cells. The invention provides a pseudo-virus to achieve these results. The recombinant defective virus of the invention comprises a genome defective for the expression of a protein essential for virus replication. Examples of such proteins are structural proteins and more particularly, capsid proteins.

The invention also provides a novel vaccine strategy modeled on the use of hepatitis virus as a vector to deliver foreign antigenic epitopes into the liver. Presentation of these epitopes by liver cells would, in turn, attract efficient (i.e., non-exhausted) T cell responses to the target tissue, for example, the liver, and contribute to viral clearance.

In one embodiment, the recombinant, replication defective virus is hepatitis virus that co-maintains in vivo with wild type hepatitis virus in hepatitis virus-infected hepatocytes, and that immunologically contributes, after complementation, to hepatitis virus clearance by expressing foreign antigenic epitopes in hepatitis virus-infected hepatocytes. The invention provides a hepatitis pseudo-virus to achieve these results.

More particularly, the invention involves the design of polynucleotides and expression vectors for cloning and expressing foreign peptides or polypeptides, such as Flu polyepitopes, in the pseudo-virus. In one embodiment, the polynucleotides and expression vectors are designed for cloning and expressing foreign peptides or polypeptides, such as Flu polyepitopes, in the hepatitis pseudo-virus. Polynucleotides and expression vectors comprising these polynucleotides have been designed, all preserving recombinant hepatitis pseudo-virus formation.

In one embodiment, this invention provides a recombinant replication defective hepatitis virus comprising a hepatitis virus genome defective for the expression of hepatitis virus capsid protein (HBc). The virus contains a nucleotide sequence of up to about 195 nucleotides encoding at least one immuno-dominant epitope of a pathogen. The nucleotide sequence is located between nucleotide residue 1981 and nucleotide residue 2308 of the HBV ayw3 genome (numbering starts from the EcoRI site of the HBV genome, NCBI Accession No. V01460 (SEQ ID NO:22)). Hepatitis B is a preferred virus for use in practicing the invention.

A vertebrate cell, transfected by the recombinant, replication defective virus of the invention is also provided. In one embodiment, the vertebrate cell is a hepatocyte cell and the virus is hepatitis virus. In one embodiment, the recombinant virus can be produced by co-transfection of a hepatocytic cell line such as Huh 7 (11) or Hep G2 (12) by one of the two constructs prHBV1.3-III or -IV with a plasmid encoding wild type capsid (pCMV-core or pMAS-core) or by transfection with a plasmid such as prHBV1.3/HB, which carries 1.3 copies of the rHBV genome and an additional expression cassette for HBV wild type core protein. The hepatocyte cell can further comprise a nucleotide sequence encoding HBc for complementation of the recombinant, replication defective, hepatitis virus to form the hepatitis pseudo-virus.

This invention thus provides a replication competent pseudo-virus comprising the recombinant, replication defective virus, complemented by the capsid protein of the virus, wherein the pseudo-virus replicates in vitro in human cells. In one embodiment, the replication competent pseudo-virus is a hepatitis pseudo-virus comprising the recombinant, replication defective hepatitis virus complemented by HBc, wherein the pseudo-virus replicates in vitro in human hepatocytes.

Further, this invention provides a vertebrate cell, expressing the pseudo-virus. In one embodiment, the vertebrate cell is a hepatocyte cell expressing the hepatitis pseudo-virus.

In addition, this invention provides a method of forming a replication competent pseudo-virus, wherein the method comprises culturing the infected cells of the invention under conditions for expression of the nucleotide sequence encoding the capsid protein of the virus and complementation of the recombinant, replication defective virus to form the pseudo-virus, which can optionally be secreted from the host cell into extracellular space. In one embodiment, the method can be used to form a replication competent hepatitis pseudo-virus by culturing the infected hepatocyte cells of the invention under conditions for expression of the nucleotide sequence encoding HBc and complementation of the recombinant, replication defective hepatitis virus to form the hepatitis pseudo-virus, which can optionally be secreted from the host cell into the extracellular space.

A polynucleotide hybridizing under stringent conditions to the recombinant, replication defective virus or its complement is also provided. In one embodiment, the polynucleotide hybridizes under stringent conditions to the recombinant, replication defective hepatitis virus or its complement.

A cloning and/or expression vector comprising the recombinant, replication defective virus is further provided. In one embodiment, the cloning and/or expression vector comprises the recombinant, replication defective hepatitis virus.

Polypeptides encoded by the recombinant, replication defective virus and by the replication competent pseudo-virus are also provided. In one embodiment, the polypeptides are encoded by the recombinant, replication defective hepatitis virus and by the replication competent hepatitis pseudo-virus.

Further, this invention provides a eukaryotic host cell comprising a vector of the invention. In one embodiment, the vector in the eukaryotic host cell comprises a eukaryotic promoter sequence operably linked to a nucleotide sequence for expression of hepatitis pseudo-virus. Optionally, the vector can comprise a nucleotide sequence encoding a fusion protein comprising a foreign polypeptide and a viral protein, wherein the eukaryotic host cell produces pseudo-virus comprising the fusion protein. In one embodiment, the fusion protein comprises a hepatitis protein and the eukaryotic host cell produces hepatitis pseudo-virus comprising the fusion protein.

More particularly, in certain embodiments, this invention relates to a vector derived from the HBV genome. The HBV genome is modified in order to express foreign antigenic epitope(s) fused within the N-terminal part of the HBV capsid protein yielding a recombinant HBV virus that will co-maintain in the liver of HBV-infected individuals through wild type capsid complementation. The HBV genome can be further modified to allow the expression and presentation of foreign epitope(s) at the surface of hepatocytes after infection with this recombinant HBV virus. The foreign antigenic epitope(s) can be derived from common pathogens that are presented in association of MHC class 1 molecules and serve as targets of the host $CD8^+$ T-cell immune response. The replication of the recombinant HBV vector in already HBV-infected hepatocytes can thereby immunologically contribute to HBV clearance by expressing foreign antigenic epitope(s) in HBV-infected hepatocytes.

Only virus-infected cells that allow replication of the recombinant virus vector of the invention are the targets of the immune response. In one embodiment, the virus-infected cells are hepatitis virus-infected hepatocytes that allow replication of the recombinant hepatitis virus vector of the invention. The recombinant, replication defective virus delivers foreign antigenic epitope(s) (for instance, polyepitopes) via the replication competent pseudo-virus of the invention in the cells of a vertebrate, and subsequently elicits strong (poly) epitope-specific immune responses. In one embodiment, the recombinant, replication defective virus is a recombinant, replication defective hepatitis virus and the vertebrate cells are hepatocytes. Hepatitis virus is cleared through cytolytic or non-cytolytic mechanisms.

The pseudo-virus of the invention results in the induction of robust immune responses and the enhancement of the activation state of sequence-specific CD4+ and CD8+ T lymphocytes so that the pseudo-virus can be employed in therapeutic applications. In one embodiment, the pseudo-virus of the invention is a hepatitis pseudo-virus.

The prHBV1.3 DNA may be used as a DNA vaccine for therapeutic intervention in chronically HBV-infected patients. This construct expresses the three HBV envelope proteins, the polymerase, and the HBx protein. The vector is non-replicative when administered as DNA through a systemic route. The pCMV-rHBe construct encodes a secreted form of HBeAg carrying foreign epitopes. It induces T cell responses specific for the foreign epitope and can be used as a vector for DNA immunization against pathogens harboring those epitopes.

Accordingly, the invention provides a composition comprising the replication defective virus of the invention and a vaccine comprising said composition. The vaccines of the invention may be administered to a patient persistently infected with a virus in order to stimulate a T cell response against cells infected with the virus. Thus, the invention also contemplates the use of the recombinant replication defective viruses of the invention for the preparation of a medicament for treating a patient persistently infected with the wild type virus. The invention also contemplates a method for targeting the expression of an epitope in a cell infected with a virus by providing to the cell the recombinant replication defective virus of the invention.

The invention provides antibodies to the chimeric antigenic fusion proteins produced by the pseudoviruses of the invention.

The invention also provides a mouse, for example, an HLA-A2/DR1 or an HbsAg/HLA-A2 double transgenic mouse, comprising a plasmid described herein. The plasmid may have entered the cells of the mouse using any method known in the art for producing transgenic animals. In an embodiment, the animal is injected intramuscularly or hydrodynamically, e.g., through a tail vein.

In an embodiment, the animal comprises prHBV-1.3, e.g., prHBV-1.3-III or prHBV-1.3-IV. In an embodiment, the transgenic animal comprises a plasmid comprising a polynucleotide sequence encoding rHBe_III, rHBe_IV, polytope III, or polytope IV.

In an embodiment, the percentage of CD8+ T cells of the transgenic animal increases in response to infection with a pseudo-virus of the invention. In an embodiment, the transgenic animal mounts an epitope-specific T-cell response to a pseudo-virus of the invention. In an embodiment, a rHBV is expressed in liver cells, with an encoded foreign antigen processed into polypeptides for immune recognition.

The invention provides a method of vaccinating an animal chronically infected with a pathogenic virus by providing a recombinant replication-competent pseudo-virus comprising the recombinant, replication defective virus, complemented by the capsid protein of the virus. In an embodiment, the animal is a mammal, e.g., a human. In an embodiment, the plasmid is any of the plasmids of the invention, as described in greater detail herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

This invention will be described with reference to the drawings in which.

(A) HBV DNA was PCR amplified.

(B) depicts the production of HBsAg carrying particles in the supernatant from these cells.

(C) depicts LHBs-virion rescue. This is also depicted in FIG. 12D.

Figure 4:
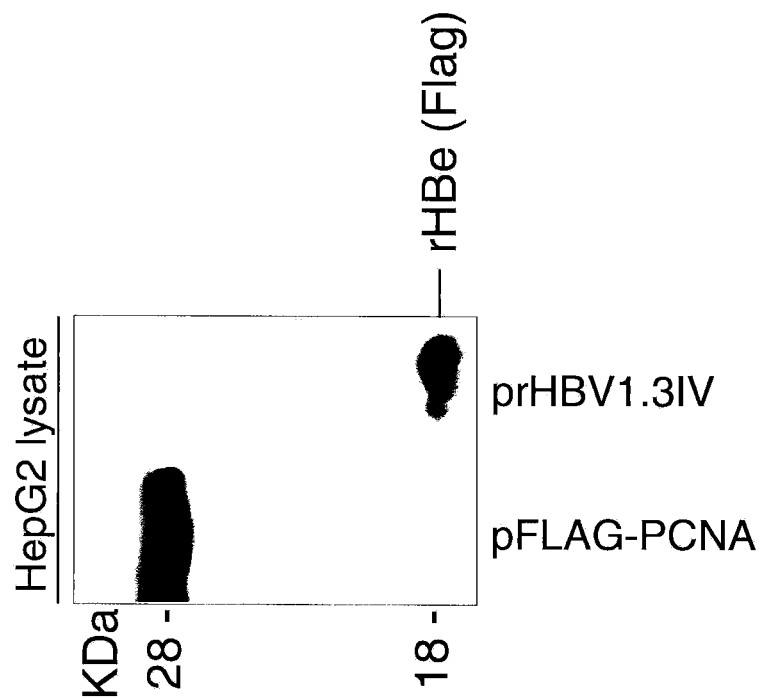

FIG. 4 shows the detection by Western blot of the recombinant antigen rHBe after transient transfection in HepG2 cell line (ATCC number HB-8065).

Figure 5:
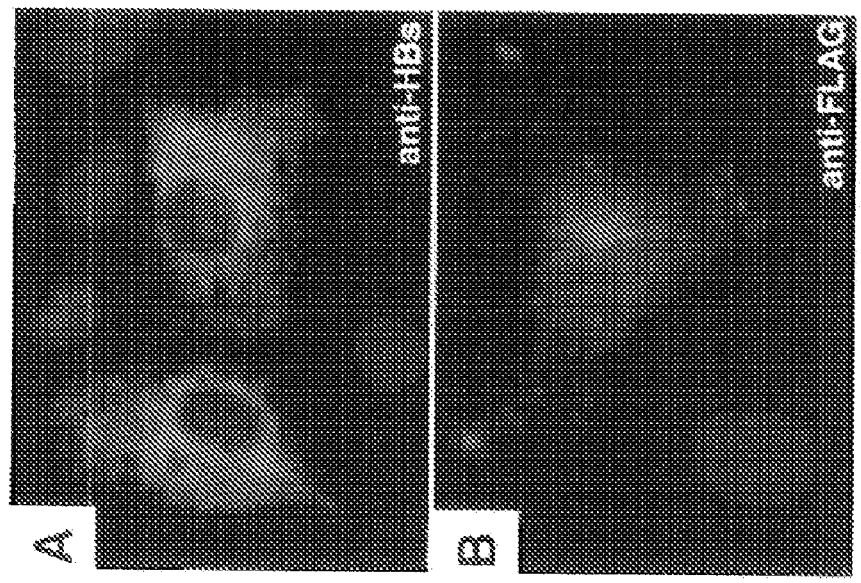

FIG. 5 shows the detection by immunofluorescence staining with antibodies of the recombinant antigen rHBe after transient transfection in the HepG2 cell line. This is also shown in FIG. 12B.

Figure 6:
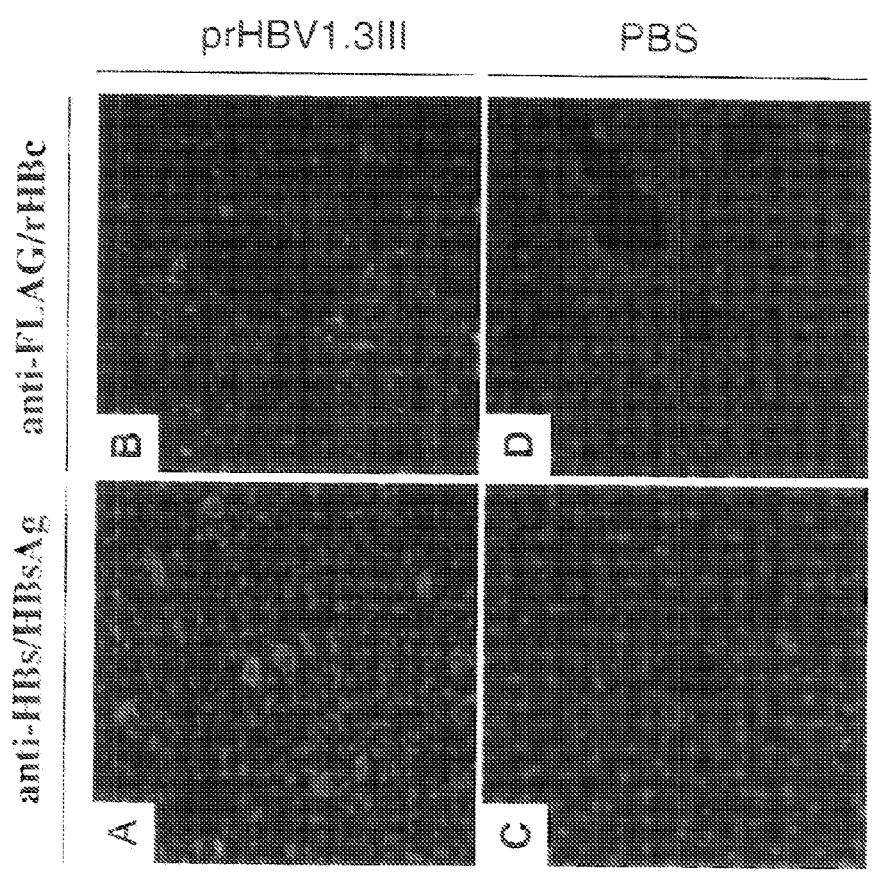

FIG. 6 shows immunostaining of the foreign recombinant antigen in liver sections after hydrodynamic injection of prHBV1.3-III into mice (ATCC number HB-8065). This is also shown in FIG. 12C.

Figure 7:
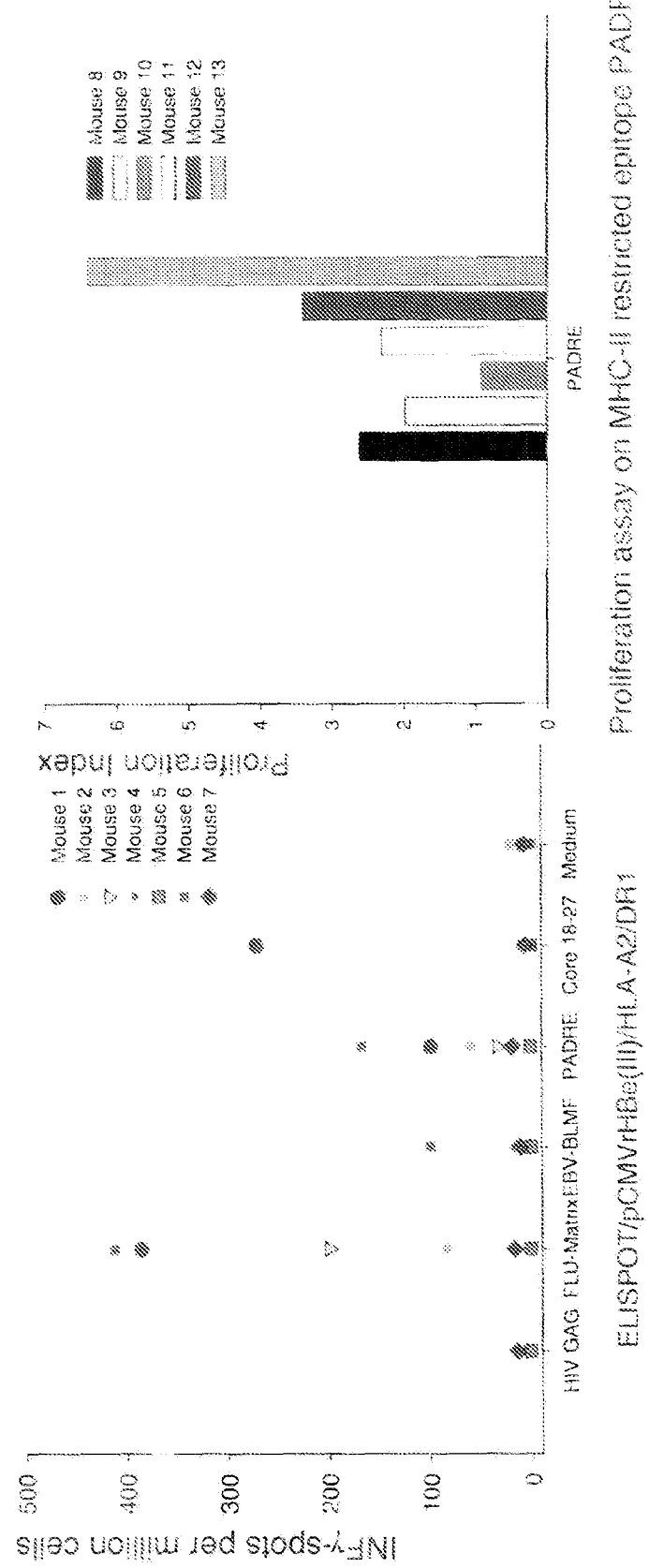

FIG. 7 shows cellular responses to the polyepitope in the rHBV genome of HLA-A2/DR1 Tg mice, detected by ELISPOT assay (left panel) and by a proliferation assay (right panel; this is also shown in FIG. 14C).

Figure 8:
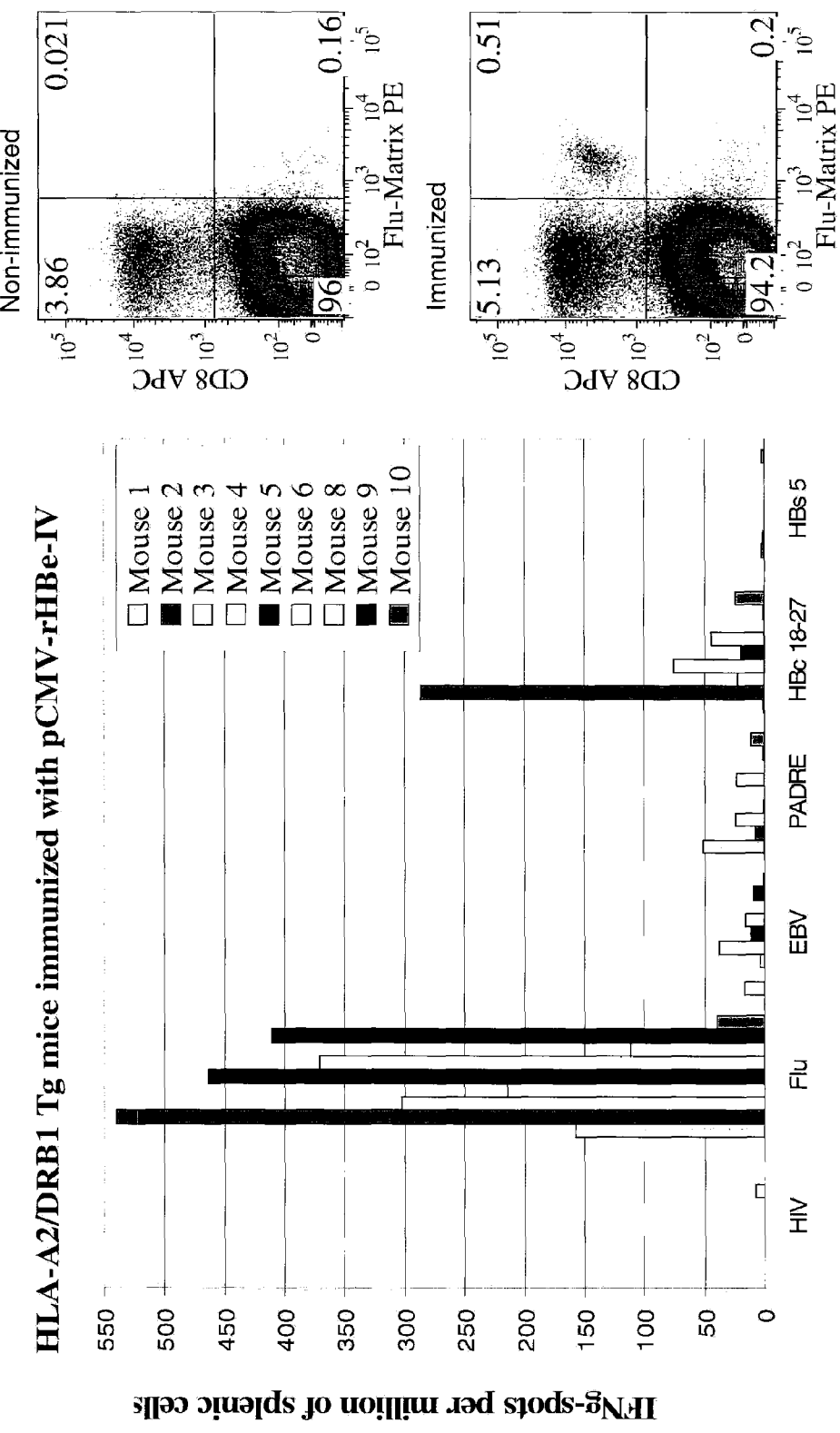

FIG. 8 shows the immune response of HLA-A2/DRB1 Tg mice immunized with pCMV-rHBe-IV. The left panel shows the immunodominant response to an epitope derived from influenza matrix protein. This is also shown in FIG. 14A. The right panel shows the detection in spleen cells of Flu-specific CD8+ T cells labeled with HLA-A2 tetramers carrying the Flu epitope in HLA-A2/DRB1 non-immunized (upper right) or immunized mice (lower right). This is also shown in FIG. 14B.

Figure 9:
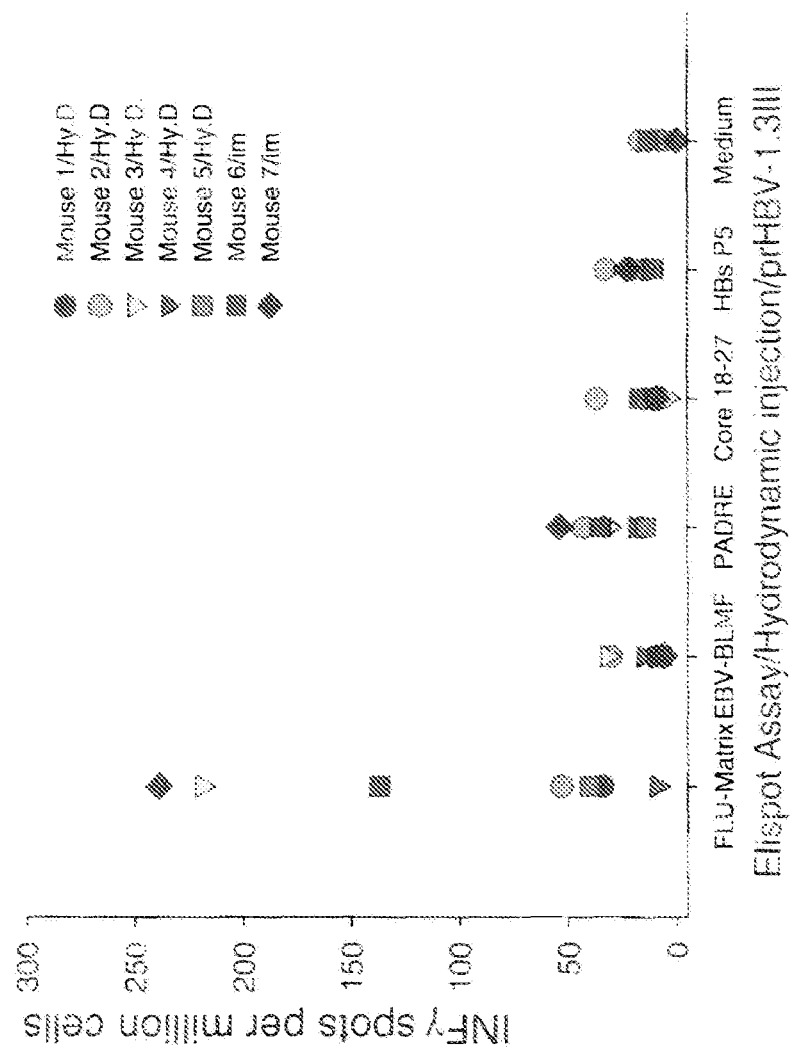

FIG. 9 shows the T cell response after hydrodynamic injection of prHBV-1.3III through the tail vein of the mouse (ELISPOT assay).

Figure 10:
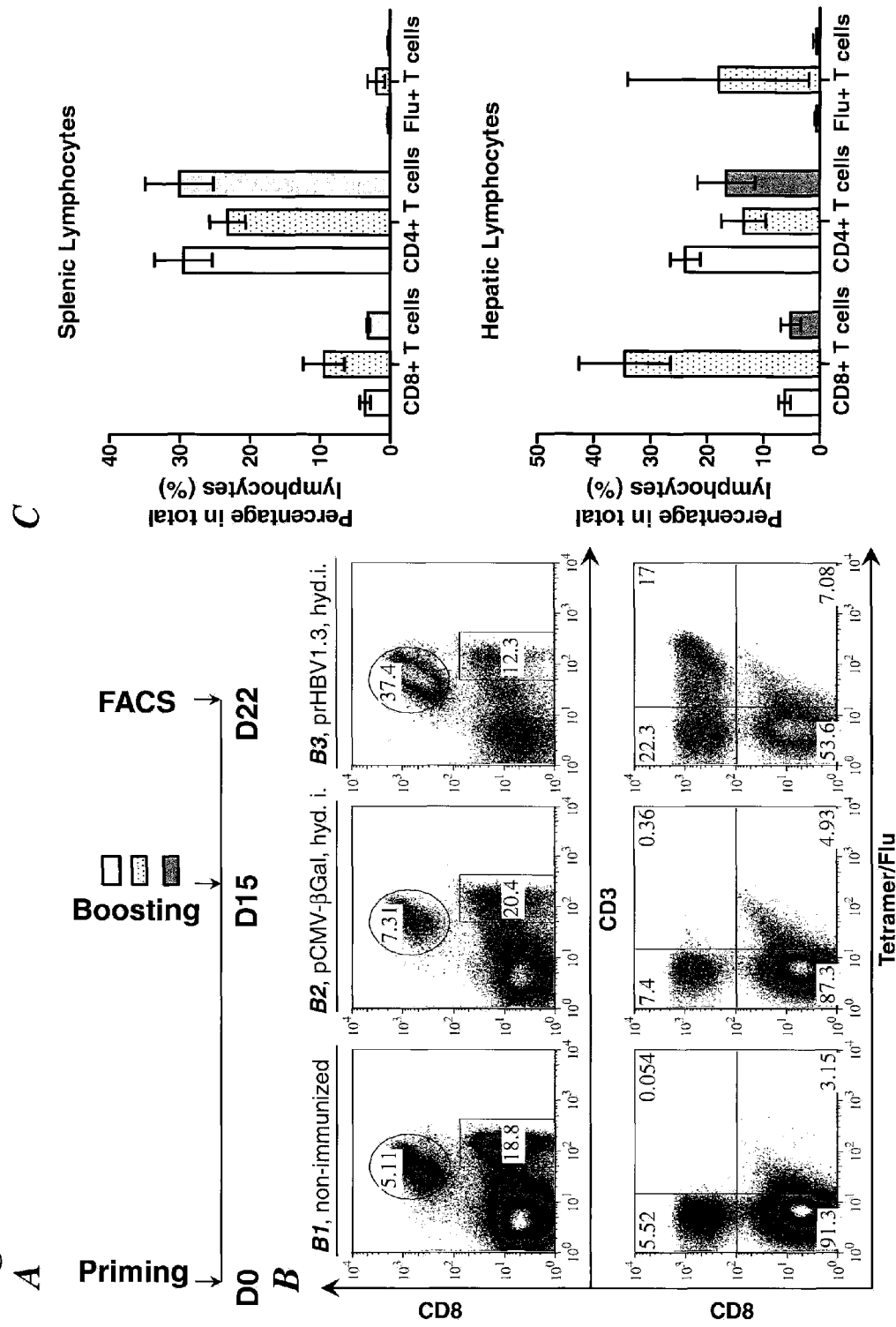

FIG. 10 shows the T-cell responses to a polyepitope in vivo and the localization of Flu-specific T cells in the liver of mice after hydrodynamic injection of prHBV1.3. This is also shown in FIG. 15.

(A) Immunization time-line; prHBV1.3 (dotted square), pCMV-βGal (control plasmid, empty square), pCMV-rHBe (grey square).

(B) Fluorescence Activated Cell Sorting (FACS) analysis of liver infiltrating lymphocytes; non-injected mice (panel B1), mice receiving pCMV-βGal (panel B2), mice receiving prHBV1.3 (panel B3); lower panels show Flu-specific T cells staining for each treatment.

(C) Localization of T cells and Flu-specific T cells in spleen (upper panel) and liver (lower panel); mice receiving hydrodynamic injection of prHBV1.3 (dotted bars), mice receiving pCMV-βGal (empty bars), mice receiving pCMV-rHBe (grey bars).

Figure 11:
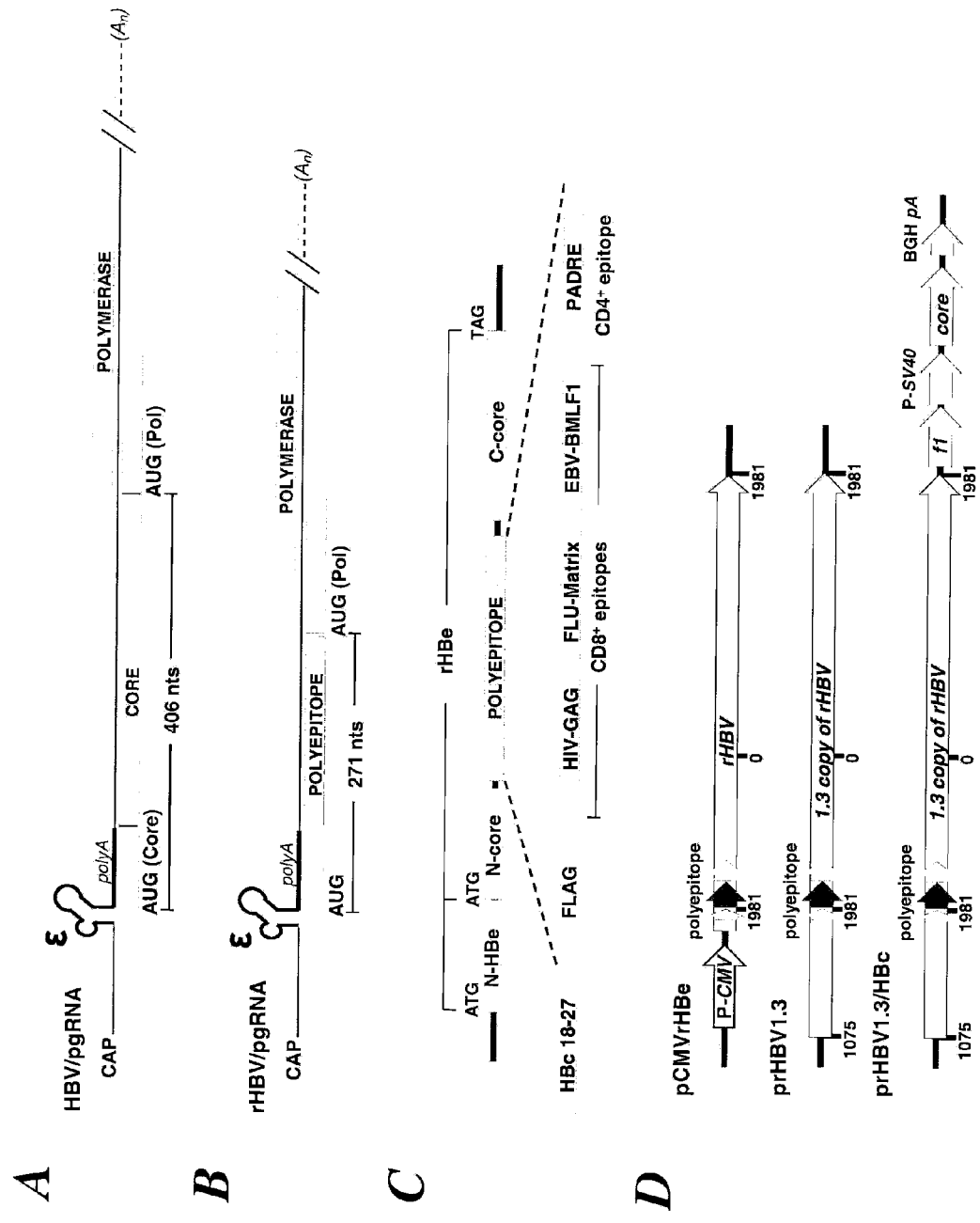

FIG. 11 shows a schematic representation of rHBV constructs and plasmids.

(A) HBV pregenomic RNA (HBV/pgRNA) is represented by a thin blue line with a capping site (cap), encapsidation (ε), and polyadenylation ($A_n$) signals indicated. The distance between AUG codons of the core and polymerase (pol) open reading frames is 406 nucleotides (nts).

(B) rHBV pregenomic RNA is shown; a short DNA sequence (in blue) encoding the foreign antigenic polyepitope was inserted in-frame within the core open reading frame, allowing the expression of a chimeric protein (rHBc).

(C) A schematic representation of the rHBc-encoding domain shows two in-frame ATG codons for the expression of HBe antigen and for core protein, respectively. A polyepitope comprising a B cell epitope (FLAG) used as a detection marker; three HLA-A2 restricted CD8 T-cell epitopes derived respectively from HIV Gag, influenza matrix, and EBV BMLF-1 proteins; and a universal CD4⁻ T cell epitope PADRE. The polyepitope sequences were inserted in-frame within the amino terminal portion of the core gene.

(D) A schematic representation of plasmids is shown. The pCMVrHBc plasmid allows expression of rHBc as well as the rHBV genome under the control of CMV early gene promoter (P-CMV). The prHBV1.3 plasmid carries 1.3 copies of the rHBV genome. The prHBV1.3/HBc plasmid carries, in addition to the 1.3 copies of rHBV genome, a cassette for the expression of wild type HBV core gene, under the control of an SV40 early gene promoter (P-SV40), and uses one or more bovine growth hormone gene-derived polyadenylation signal (BGH pA). Positions of core ORFs with the inserted polyepitope-encoding sequence is indicated by arrows. Nucleotide positions are indicated according to the sequence of the HBV genotype D ayw subtype. Position 0 corresponds to the EcoR1 site and position 1981 corresponds to the 3'-end of the polyadenylation signal for mRNA in the HBV genome.

Figure 12:
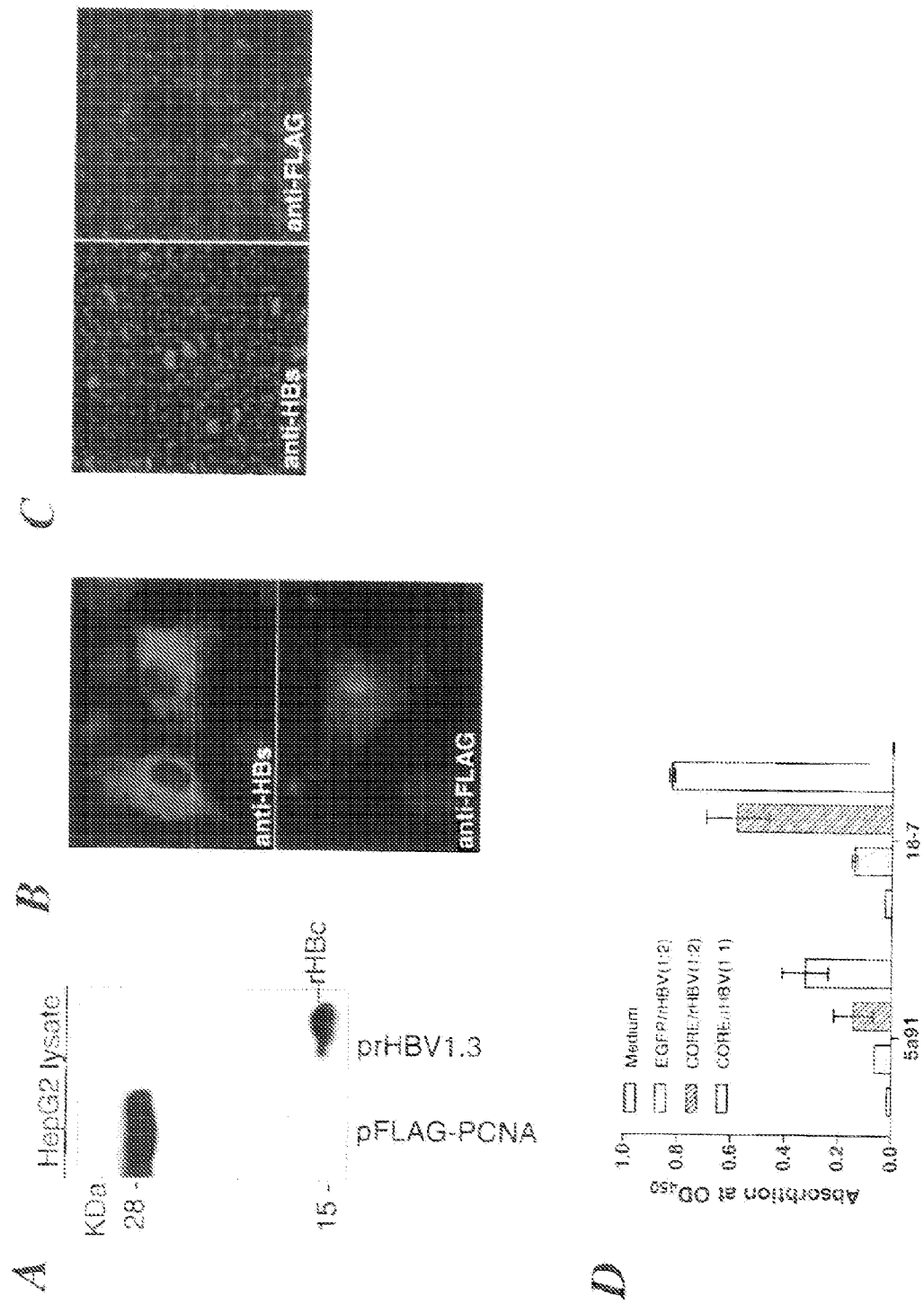

FIG. 12 shows the expression of rHBV and chimeric antigenic protein.

(A) Western blot analysis of cell lysate obtained after transfection of the HepG2 cell line (ATCC number HB-8065) with pFLAG-PCNA or prHBV1.3 plasmids. The molecular weights of proliferating cell nuclear antigen (PCNA) fused with Flag (lane 1; control) and rHBc (lane 2) are estimated according to molecular weight markers (kilodaltons (KDa)).

(B) Immunofluorescence staining of HepG2 cells transfected with prHBV1.3 plasmid using anti-HBs (upper panel) or anti-FLAG antibodies (lower panel). DAPI stained nuclei are in blue.

(C) Antibody labeling (anti-HBs, left panel and anti-FLAG, right panel) and immunofluorescence staining on liver sections taken from mice (ATCC number HB-8065) four days following hydrodynamic injection of prHBV1.3.

(D) Quantification of HBsAg particles containing HBV-L protein by sandwich ELISA. PreS1-specific monoclonal antibodies (5a91 and 18-7) were used as capture antibodies to detect L protein in culture supernatants of Huh-7 cells transfected with two different ratios of prHBV1.3 (rHBV) and pMAS-C(CORE) plasmids or with a control plasmid pIRES-EGFP (EGFP). Results are expressed as optical densities (OD) at 450 nm, by ELISA.

Figure 13:
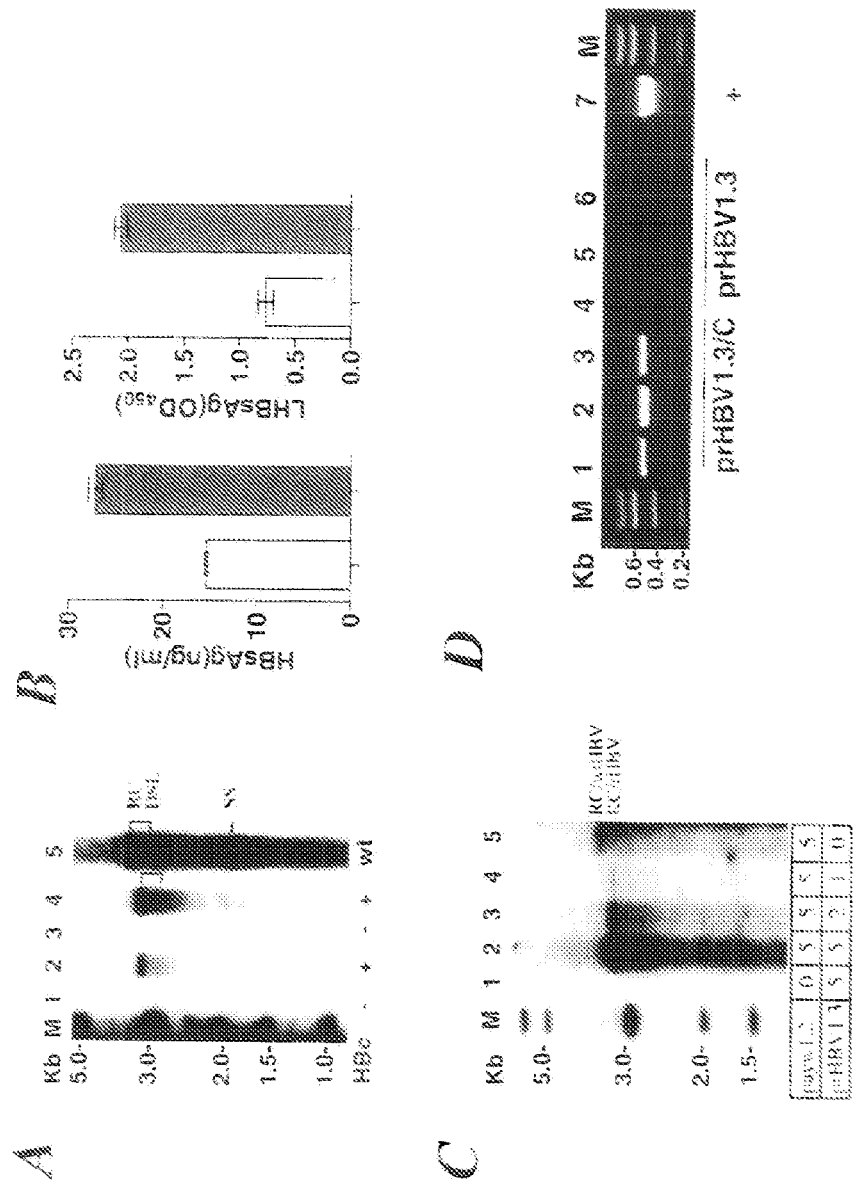

FIG. 13 shows the encapsidation rHBV genome by wild type core protein.

(A) Viral DNA detected by Southern blot assay with an HBV-specific probe in the cell culture supernatants of Huh 7 cells transfected with two different concentrations of prHBV1.3 (lanes 1, 3) or prHBV1.3/HBc plasmids (lanes 2, 4). Wild type HBV DNA was extracted from the HepAD38 cell line as a control (lane 5). Bands corresponding to relaxed circular (RC), double-stranded linear (DSL) and single-stranded (SS) HBV DNA are indicated. M: molecular weight markers (Kb). HBc+ indicates expression of capsid protein by the vector used in transfection experiments.

(B) ELISA assay results comparing HbsAg (left) and LHBsAg (right) production in culture medium (from day 3-5) of Huh 7 cells transfected with either prHBV1.3 (empty columns) or prHBV1.3/HBc (grey columns). HBsAg (ng/ml) was quantified by Monolisa detection kit (Bio-Rad, Hercules, Calif.). LHBsAg production was expressed as optical densities (OD) at 450 nm.

(C) Southern blot assay of the viral DNA in Huh 7 cells 3 days after cotransfection with payw 1.2 and prHBV 1.3. The concentrations of each are shown in the table below the blot.

(D) Detection of viral DNA by PCR in sera of C57/BL6 mice four days after hydrodynamic injection of prHBV1.3 with either pMAS-C (lanes 1-3) or pCMV-βGal (lanes 4-6). pFC80 plasmid was used as a positive control (lane 7).

Figure 14:
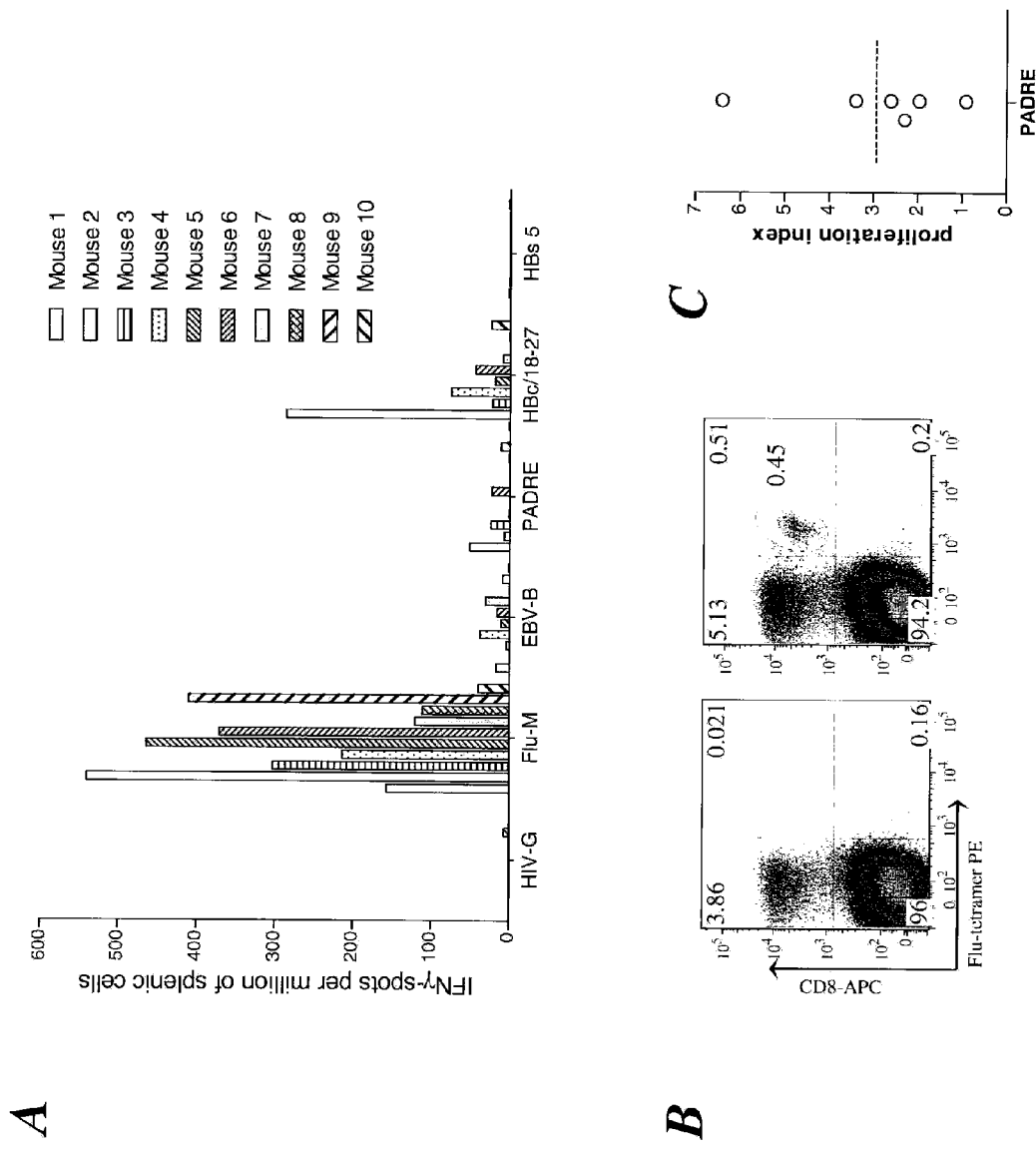

FIG. 14 shows polyepitope-specific T-cell responses in mice injected with pCMV-rHBe.

(A) ELIspot assay performed on splenocytes from ten HLA-A2/DR1 transgenic mice taken 15 days after one intramuscular injection of pCMV-rHBe. Each bar represents the number of IFN-γ-secreting T cells per million splenocytes for each individual mouse. Peptides used to stimulate splenocytes ex vivo are derived from HIV gag (HIV-G), Influenza matrix (Flu-M), EBV-BMLF1 (EBV-B), HBV capsid (HBc/18-27), and HBV envelope (HBs 5) proteins. PADRE is a promiscuous HLA-class II-binding peptide.

(B) FACS analysis of Flu-specific T cells from a non-immunized mouse (left panel) and from a representative HLA-A2/DR1 transgenic mouse (right panel) taken 15 days after one intramuscular injection of pCMV-rHBe. Spleen cells were stained with an APC-labeled anti-CD8 antibody and a HLA-A2-pentamer carrying the Flu peptide. Flu-specific T cells represent around 10% of CD8 T cells from the spleen (red circle).

(C) Proliferative response of splenocytes from pCMV-rHBc-immunized HLA-A2/DR1 transgenic mice following in vitro stimulation with PADRE peptide. Responses are expressed as the proliferation index. The dotted line corresponds to the mean value of the stimulation index. SI>2 is considered positive.

FIG. 15 shows T cell responses in the liver and spleen of HLA-A2/DR1 transgenic mice, following hydrodynamic injection of rHBV.

(A) The protocol for active immunization includes priming of T cell responses at day 0 (D0) by intramuscular injection of pCMV-rHBc. At day 15 (D15), mice were injected via the hydrodynamic route with either prHBV1.3 or control pCMV-βGal plasmid. Lymphocytes from spleen and liver were collected at day 22 (D22) for FACS analysis.

(B) FACS analysis of intrahepatic lymphocytes stained with anti-CD3-PerCP and anti-CD8-APC antibodies (upper panels), and with PE-labeled Flu-specific tetramer and APC-labeled anti-CD8 (lower panels). Lymphocytes were prepared from non-immunized mice (B1, left panels), mice receiving pCMVrHBc priming/pCMVβGal hydrodynamic injection (B2, middle panels), and mice receiving pCMVrHBc priming/prHBV1.3 hydrodynamic injection (B3, right panels). The percentages of CD8⁺ (circle) and CD4⁺ (square) T cells among the splenocytes are indicated.

(C) Analysis of intrahepatic lymphocytes from three groups of mice. The first group received pCMVrHBc priming/pCMVβGal hydrodynamic injection (empty bars, n=5); the second group received pCMVrHBc priming/prHBV1.3 hydrodynamic injection (dotted bars, n=6); the third group were injected twice with pCMVrHBc via the intramuscular route (grey bars, n=3). Results are given as the mean±SEM percentage of CD8+, CD4+ and Flu-specific T cells in the total lymphocyte population.

(D) Analysis of the intrasplenic lymphocytes from the mice described in FIG. 15C.

FIG. 16 shows an analysis of liver-infiltrating lymphocytes.

(A) Histological analysis of liver sections taken four days after hydrodynamic injection. Hematoxylin/eosin staining of liver sections from a representative HLA-A2/DR1 mouse receiving pCMVrHBc priming/pCMVβGal hydrodynamic injection (left panel, 100×); and from a representative mouse receiving pCMVrHBc priming/prHBV1.3 hydrodynamic injection (middle panel, 100×). The right panel shows an area from the middle panel at a magnification of 200×. Cell clusters of inflammatory foci are indicated with frames. Arrows indicate cells undergoing degeneration.

(B) Phenotype of intrahepatic lymphocytes taken from a representative mouse after pCMVrHBc priming/prHBV1.3 hydrodynamic injection. CD8+ T cells were gated for analysis of Flu+ or Flu negative cells following Flu-pentamer labeling (left panel). Quantification of CD69+ and CD62L+ cells was done on pentamer positive (middle panel) and pentamer negative (right panel) CD8 T cells.

(C) Functional profile of CD3+ CD8+ intrahepatic T cells. Cells were analyzed for CD107, a surface marker, intracellular INFγ, and TNFα, following ex vivo stimulation with poly-epitope-derived peptides (mix of three) (lower panel) or without stimulation (upper panel).

(D) Immunostaining of HBsAg on liver sections taken four days after prHBV1.3 hydrodynamic injection from mice that were either primed by pCMVrHBc intramuscular injection (left panel) or unprimed (right panel) before hydrodynamic injection of prHBV1.3.

(E) Mean level of HBsAg (ng/ml) in the sera of the mice of FIG. 16D with priming (empty columns) or without priming (grey columns), before hydrodynamic injection of prHBV1.3.

(F) Mean level of transaminase (ALT mU/ml) in the sera of the mice following pCMV-rHBc priming/prHBV1.3 hydrodynamic injection (grey column, n=11), and of mice with pCMV-rHBc primin/pCMV-βGal hydrodynamic injection (empty column, n=4). Concanavalin A (ConA) injection was used as a positive control for ALT increase.

Figure 17:
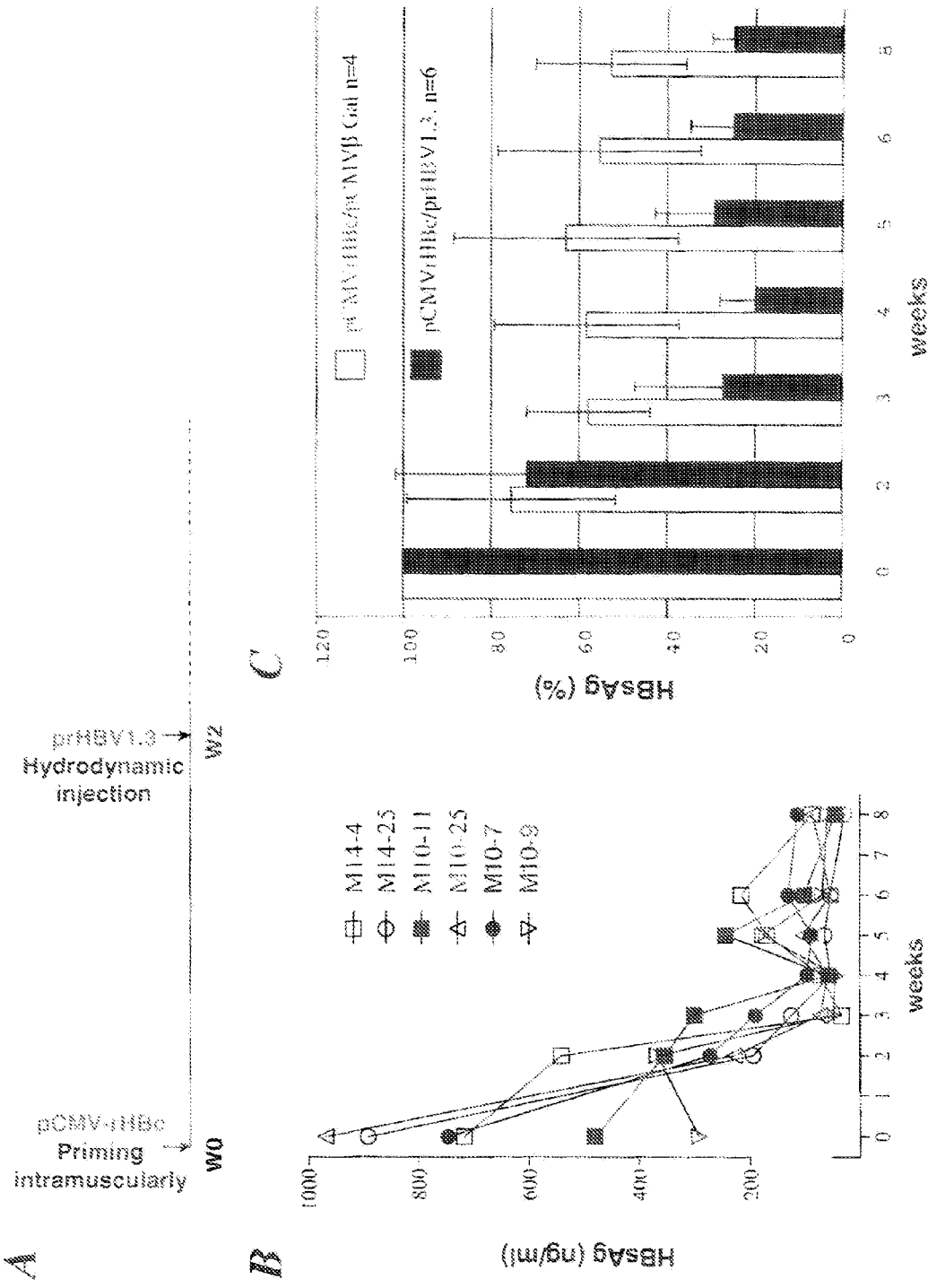

FIG. 17 shows the control of HBsAg expression in HBsAg/HLA-A2 transgenic mice.

(A) Protocol for active immunization in HBsAg/HLA-A2 transgenic mice.

(B) Decrease in HBsAg in the sera of individual HBsAg/HLA-A2 transgenic mice after priming by intramuscular injection of pCMV-rHBc at week 0 (W0), followed by prHBV1.3 hydrodynamic injection two weeks later (W2). Mice were bled weekly and HBsAg (ng/ml) was quantified using a commercial ELISA.

(C) The percentage of HBsAg decrease over eight weeks in the sera of mice receiving prHBV1.3 (filled bars) or pCMV-βGal (empty bars). HBsAg concentration at week 0 was set at 100% and the results are expressed as mean±SEM.

DETAILED DESCRIPTION OF THE INVENTION

Hepadnaviruses are small, enveloped hepatotropic DNA viruses. The prototype member of this family is the human hepatitis B virus (HBV). The hepadnaviral genome consists of a partially double-stranded, relaxed circular DNA, which has a compact organization employing widely overlapping open reading frames and regulatory sequences. HBV genome is precisely-organized by various cis- or trans-elements that are overlapping each other.

By investigation of the viral genome, it was found that it might accommodate a piece of foreign sequence in the N-terminal part of the capsid-coding region to create a pseudo-virus that would maintain in hepatocytes, while the interrupted protein would be complemented in trans by wild type HBV during natural infection. (Gunther, S., Piwon, N., Jung, A., Iwanska, A., Schmitz, H., Will, H. (2000) Enhanced replication contributes to enrichment of hepatitis B virus with a deletion in the core gene, *Virology* 273:286-99.) Thus, recombinant HBV would act as a targeting vector with liver-tropism for gene delivery (see FIG. 1).

Thus, this invention provides a vector derived from the hepatitis virus genome. The hepatitis virus genome was modified in order to express foreign epitopes fused within the N-terminal part of the hepatitis virus capsid protein. The resulting virus is replication defective. This recombinant, replication defective, hepatitis virus co-maintains in the liver of hepatitis virus-infected individuals through wild type capsid complementation. Infection with this recombinant virus leads to expression and presentation of foreign epitopes at the surface of hepatocytes. These epitopes presented in association with MHC molecules are the target of the host T-cell immune response. Therefore, only hepatitis virus-infected hepatocytes that allow replication of the recombinant hepatitis virus vector will be the target of the immune response and cured. The invention exploits the pre-existing immunity against foreign epitopes, for example from common pathogens, such as Flu. Hepatitis virus is cleared through cytolytic or non-cytolytic mechanisms.

In patients, viral clearance can be quantified by measuring HBV DNA in sera using commercially available kits. Clearance in the liver can be quantified by measuring DNA in biopsy. Sero-conversion from HBeAg, which is a marker of viral replication, to anti-HBe antibodies can be used as a marker for viral elimination. Elimination of HBsAg from the sera and seroconversion to anti-HBs antibodies indicates the complete elimination of the virus.

This invention also provides a recombinant, replication competent hepatitis pseudo-virus based on the replication defective hepatitis virus of the invention. The pseudo-virus comprises the recombinant, replication defective, hepatitis virus of the invention complemented by HBc, wherein the pseudo-virus replicates in vitro in human hepatocytes.

More particularly, this invention provides a recombinant, replication defective, hepatitis virus comprising a hepatitis virus genome defective for the expression of hepatitis virus capsid protein (HBc), wherein the virus contains a nucleotide sequence of up to about 195 nucleotides encoding at least one immuno-dominant epitope of a pathogen, wherein the nucleotide sequence is located between nucleotide residue 1981 and nucleotide residue 2308 of the HBV ayw3 genome (numbering starts from the fourth nucleotide in the EcoRI site of the HBV genome, NCBI Accession No. V01460 (SEQ ID NO:22)). This virus is referred to herein as "the recombinant, replication defective, hepatitis virus" of the invention.

The recombinant, replication defective, hepatitis virus of the invention is complemented in the infected cell by expression of HBc by the hepatitis virus infecting cell. The genome of the replication incompetent virus is completely enclosed within the capsid produced by the wild hepatitis virus infecting the cell. The complemented virus is referred to herein as "the hepatitis pseudo-virus."

This invention thus provides polynucleotides and expression vectors for the production of proteins, which assemble into pseudo-virus, and which are efficiently produced in host cells. It is thus possible to make self-assembling, recombinant, pseudo-virus with residues of a foreign peptide. This provides efficient monovalent, bivalent, and multivalent immunogenic compositions and therapeutic vaccines.

While the replication defective hepatitis virus and the hepatitis-pseudo-virus of the invention will be described in detail with reference to HBV, it will be understood that this invention is applicable to other hepatitis viruses, including Hepatitis A Virus (HAV) (Picornavirus); Hepatitis Delta Virus (HDV) (Deltavirus); Hepatitis C Virus (HCV) (Flavivirus); and Hepatitis E Virus (HV). Thus, as used herein, the term "hepatitis" includes hepatitis B and other hepatitis viruses. Hepatitis B is the preferred virus for use in practicing this invention. More generally, the invention is applicable to other viruses.

In practicing the invention using other hepatotrophic viruses, such as HCV, and more generally all viruses involved in persistent infection, the viral genome can be examined to identify an appropriate site for the insertion of foreign epitopes. For example, due to overlapping open reading frames encoding the structural and non-structural viral proteins of HBV, the only gene that can be targeted for epitope insertion is the nucleocapsid-encoding gene. However, other RNA or DNA viruses have different tolerances for genomic insertions. In addition, different viruses infect different tissues that can be targeted and destroyed by the induced T cell responses, without damaging other non-infected tissues.

The term "peptide" is generally understood in the art to refer to a small amino acid molecule, whereas the term "polypeptide" is generally understood to refer to a larger amino acid molecule. Both peptides and polypeptides are within the scope of this invention. Thus, for example, the foreign sequences can be either a peptide or a polypeptide. The terms are used interchangeably herein.

In one aspect, the invention provides hepatitis pseudo-viruses comprising epitope-bearing portions of foreign peptide(s) or polypeptide(s). As used herein, the terms foreign peptides and polypeptides or epitopes means a peptide or polypeptide or an epitope not found in wild-type hepatitis virus.

The epitopes are immunogenic or antigenic epitopes of the foreign peptides or polypeptides. An "immunogenic epitope" is defined as a part of a protein that elicits a humoral or cellular response in vivo when the whole polypeptide, or fragment thereof, is the immunogen. A region of a polypeptide to which an antibody can bind is defined as an "antigenic determinant" or "antigenic epitope." The antigenic epitope can also elicit a humoral or cellular response in vivo when employed in the hepatitis pseudo-virus. Thus, included in the present invention are hepatitis pseudo-viruses containing both immunogenic epitopes and antigenic epitopes, or either one of them. Foreign peptides or polypeptides comprising immunogenic or antigenic epitopes are at least 8 amino acids residues in length for epitopes binding to MHC class I molecules, and at least 12 amino acids in length for epitopes binding to MHC class II molecules (cellular response). B cell (humoral response) epitopes are at least four amino acids in length.

In some embodiments, the foreign peptide or polypeptide can contain from about 8 to about 140 amino acid residues, preferably from about 20 to about 140 amino acid residues, especially from about 60 to about 140 amino acid residues. In the case of HBV, it can contain up to about 68 amino acids. In one embodiment, in the case of HBV, the foreign peptide or polypeptide contains 68 amino acids. In another embodiment, it contains about 65 amino acids. Flanking residues on either the N-terminal, C-terminal, or both N- and C-terminal ends may be added to the foreign peptide or polypeptide to generate the hepatitis pseudo-viruses.

The foreign peptide or polypeptide can also be derived from any number of foreign proteins. The foreign peptide or polypeptide can be derived from any protein of any plant, animal, bacterial, viral, or parasitic organism.

In one embodiment, the foreign peptide or polypeptide can be derived from a polypeptide of a pathogen. The term "pathogen" as used herein, means a specific causative agent of disease, and may include, for example, any bacteria, virus, or parasite.

The term "disease" as used herein, means an interruption, cessation, or disorder of body function, system, or organ. Typical diseases include infectious diseases. For example, the foreign peptide or polypeptide can be from the immunogenic proteins of an RNA virus, such as HIV-1, HIV-2, SIV, HCV, Ebola virus, Marburg virus, HTLV-I, and HTLV-II. Specific examples are the structural or NS1 proteins of Dengue virus; the G1, G2, or N proteins of Hantaan virus; the HA proteins of Influenza A virus; the Env proteins of Friend murine leukemia virus; the Env proteins of HTLV-1 virus; the preM, E, NS1, or NS2A proteins of Japanese encephalitis virus; the N or G proteins of Lassa virus; the G or NP proteins of lymphocytic choriomeningitis virus; the HA or F proteins of measles virus; the F or HN proteins of parainfluenza 3 virus; the F or HN proteins of parainfluenza SV5 virus; the G proteins of Rabies virus; the F or G proteins of respiratory syncytial virus; the HA or F proteins of Rinderpest; or the G proteins of vesicular stomatitis virus. These are just some of the possibilities and do not represent an exhaustive or restricted list.

The foreign peptide or polypeptide can also be derived from the immunogenic proteins of a DNA virus, such as gp89 of cytomegalovirus; gp340 of Epstein-Barr; gp13 or 14 of equine herpesvirus; gB of herpes simplex 1; gD of Herpes simplex 1; gD of herpes simplex 2; or gp50 of pseudorabies. Once again, these are just some of the possibilities and do not represent an exhaustive or restricted list.

Further, the foreign peptide or polypeptide can be derived from the immunogenic proteins of bacteria, such as Streptococci A M6 antigens, or tumor antigens, such as human melanoma p97, rat Neu oncogene p185, human epithelial tumor ETA, or human papilloma virus antigens. Again, these do not comprise an exhaustive or restricted list.

In an embodiment of this invention, the foreign peptide or polypeptide is derived from a human immunodeficiency virus. Following are HIV-1 epitopes that can be employed in designing the foreign peptide or polypeptide.

| GAG | P17 (77-85) | SLYNTVATL (S9L) | (SEQ ID NO: 1) |
|---|---|---|---|
| | P24 (19-27) | TLNAWVKW (T9V) | (SEQ ID NO: 2) |
| POL | (79-88) | LLDTGADDTV (L10V) | (SEQ ID NO: 3) |
| | (263-273) | VLDVGDAYFSV (V11V) | (SEQ ID NO: 4) |
| | (334-342) | VIYQYMDDL (V9L) | (SEQ ID NO: 5) |
| | (464-472) | ILKEPVHGV (I9V) | (SEQ ID NO: 6) |
| | (576-584) | PLVKLWYQL (P9L) | (SEQ ID NO: 7) |
| | (669-679) | ESELVNQIIEQ (E11Q) | (SEQ ID NO: 8) |
| | (671-680) | ELVNQIIEQL (E10) | (SEQ ID NO: 9) |
| | (956-964) | LLWKGEGAV (L9V) | (SEQ ID NO: 10) |
| ENV | Gp41 (260-268) | RLRDLLLIV (R9V) | (SEQ ID NO: 11) |
| NEF | (188-196) | AFHHVAREL (A9L) | (SEQ ID NO: 12) |

Numbering is based on the amino acid sequence of the HIV-1 WEAU clone 1.60 (Genbank accession no. U21135).

The WEAU sequence may not be always identical to that of the reactive peptide and simply indicates its location in the viral proteins.

The foreign peptide or polypeptide can comprise one epitope or a multiplicity of epitopes linked to each other. In addition, it will be understood that the hepatitis pseudo-virus of the invention can contain multiple epitopes of one or more origins, such as epitopes from different immunogenic proteins of the same pathogen. It will also be understood that the hepatitis pseudo-virus can contain one or more epitopes from different origins, such as epitopes from different pathogens. In addition, mixtures of hepatitis pseudo-viruses having different epitopes in different particles are contemplated by this invention.

The proteins containing the foreign sequence can be exposed on the surface of cells infected with the wild-type virus. The resulting exposed epitopes provide excellent configurational mimics of the epitopes as they exist, for example, in pathogens, such as other infectious viruses. For these reasons, the virus-infected cells are suitable for exploitation as carriers for foreign peptides or polypeptides, such as protective determinants of etiologic agents, via the replication defective, hepatitis virus and the resulting hepatitis pseudo-virus of the invention.

Recombinant expression vectors containing a nucleic acid encoding proteins of the pseudo-viruses of the invention can be prepared using well known methods. The expression vectors include the sequence encoding the foreign peptide or polypeptide operably linked to suitable transcriptional or translational regulatory nucleotide sequences, such as those derived from a mammalian, viral, or insect gene. A transcriptional or translational regulatory nucleotide sequence is operably linked if the nucleotide sequence controls the transcription or translation of another coding DNA sequence. Examples of regulatory sequences include transcriptional promoters, operators, or enhancers, an mRNA ribosomal binding site, tissue specific promoters and post-transcriptional regulatory elements (PRE), and appropriate sequences that control transcription and translation initiation or termination. The ability to replicate in the desired host cells, usually conferred by an origin of replication, and a selection gene by which transformants are identified, may additionally be incorporated into the expression vector.

Among eukaryotic vectors for use in the preparation of vectors of the invention are pWLNEO, pSV2CAT, pOG44, pXT1, and pSG available from Stratagene (La Jolla, Calif.); and pSVK3, pBPV, pMSG, and pSVL available from Pharmacia (Piscataway, N.J.). Other suitable vectors will be readily apparent to the skilled artisan.

Among vectors for use in the preparation of vector of the invention, non-integrative eucaryotic vectors are not only useful, but integrative/transformant vectors (i.e. vectors that integrate a part of their nucleic acid material in the genome of the eukaryotic host cell) can also be employed. Typical of these vectors are lentiviral vector Trips, adenovirus, and yeast integrative vectors.

In a preferred embodiment, the expression vectors of the invention include at least one selectable marker. Such markers include, for example, dihydrofolate reductase, G418, ampicilin or neomycin resistance for eukaryotic cell culture.

Any strong promoter known to those skilled in the art can be used for driving expression. Suitable promoters include adenoviral promoters, such as the adenoviral major late promoter; heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the β-actin promoter; and human growth hormone promoters. The promoter also can be a native promoter from a hepatitis virus, such as HBV.

In vivo delivery of the recombinant viruses of the invention requires production of viral stocks. In the case of hepatitis virus, this can be achieved by using a hepatocytic cell line expressing wild type hepatic virus capsid. A method for the production of viral stocks is described in Gunther S. et al., Virology, 273:286-99 (2000).

Suitable host cells for expression of pseudo-virus include higher eukaryotic cells. For example, in the case of hepatitis virus, differentiated hepatocytes are required for HBV, HCV, and HDV replication. Appropriate cloning and expression vectors for use with plant, fungal, yeast, and mammalian cellular hosts are described, for example, in Pouwels et al. *Cloning Vectors: A Laboratory Manual*, Elsevier, N.Y., (1985). Representative examples of appropriate hosts include, but are not limited to, fungal cells, such as yeast cells; insect cells, such as *Drosophila* S2 and *Spodoptera* Sf9 cells; animal cells, such as CHO, COS, 293, and Bowes melanoma cells; and plant cells. Appropriate culture mediums and conditions for the above-described host cells are known in the art.

Introduction of the vector of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986).

In another aspect, the invention is directed to an in vitro method for producing pseudo virus, comprising culturing in vitro, in a suitable culture medium, a cell incorporating an expression vector of the invention and collecting in the culture medium pseudo-virus produced by these cells.

Therefore, the invention is also concerned with cells, such as recombinant eucaryotic cells, infected, transformed, or transfected by a polynucleotide or vector of the invention for expressing the pseudo-virus. Methods for producing such cells and methods for using these cells in the production of recombinant viruses are well known in the art. The pseudo-virus can be recovered and purified from recombinant cell cultures by well-known methods, including ammonium sulfate precipitation, anion or cation exchange chromatography, phosphocellulose chromatography, hydrophobic interaction chromatography, affinity chromatography, hydroxyapatite chromatography, and lectin or heparin chromatography.

While this invention relates to hepatitis pseudo-virus carrying one or more (poly)epitopes of foreign peptides or polypeptides, this invention contemplates the use of (poly) epitopes that have been optimized for incorporation in hepatitis pseudo-virus. The (poly)epitope nucleic and amino acid sequences can be modified in view of increasing the overall hydrophilicity of the (poly)epitope and ensuring a modified processing of epitopes. Epitopes in a polyepitope can be permutated in order to obtain the best hydrophilic profile. Hydrophilic spacers can be added to counterbalance the generally hydrophobic epitopes.

The polypeptides or polynucleotides of this invention can be in isolated or purified form. The terms "isolated" or "purified", as used in the context of this specification to define purity, means that the protein, polypeptide, or polynucleotide is substantially free of other proteins of natural or endogenous origin and contains less than about 1% by mass of protein or polynucleotide, of other contaminants residual of production processes.

In practicing the method of the invention, the replication defective virus is administered to a host using one of the modes of administration commonly employed for administering drugs to humans and other animals. Thus, for example, the replication defective virus can be administered to the host by the oral route or parenterally, such as by intravenous or intramuscular injection. Other modes of administration can also be employed, such as intrasplenic, intrahepatic, perfusion, intradermal, and mucosal routes. Preferably, the replication defective virus of the invention is administered according to the natural route of infection of the virus. For purposes of injection, the replication defective virus as described above can be prepared in the form of solutions, suspensions, or emulsions in vehicles conventionally employed for this purpose.

Accordingly, the invention contemplates compositions comprising the recombinant replication defective virus of the invention in combination with a pharmaceutically acceptable carrier. The invention also contemplates a vaccine comprising such compositions. The vaccines of the invention may be administered to a patient persistently infected with a virus in order to stimulate a T cell response against cells infected with the virus. Thus, the invention also contemplates the use of the recombinant replication defective viruses of the invention for the preparation of a medicament for treating a patient persistently infected with the wild type virus. The invention also contemplates a method for targeting the expression of an epitope in a cell infected with a virus by providing to the cell the recombinant replication defective virus of the invention.

It will be understood that the replication defective viruses of the invention can be used in combination with other microorganism antigens, antibodies, or mitogens or other prophylactic or therapeutic substances. For example, mixtures of different parasite antigens, antibodies, or mitogens or mixtures of different viral or bacterial antigens, antibodies, or mitogens can be employed in the method of the invention. Similarly, mixtures of different replication defective viruses can be employed in the same composition. The replication defective viruses can also be combined with other vaccinating agents, such as immunodominant, immunopathological, and immunoprotective epitope-based vaccines, or inactivated attenuated or subunit vaccines.

The replication defective viruses of the invention are employed in an effective amount sufficient to provide an adequate concentration to clear virus in infected cells. The amount of the replication defective hepatitis viruses thus depends upon absorption, distribution, and clearance by the host. Of course, the effectiveness of the replication defective hepatitis viruses is dose related. The dosage of the replication defective viruses should be sufficient to produce a minimal detectable effect, but the dosage preferably should be less than the dose that activates a non-specific polyclonal lymphocyte response.

The dosage of the replication defective viruses of the invention administered to the host can be varied over wide limits. The viruses can be administered in the minimum quantity, which is therapeutically effective, and the dosage can be increased as desired up the maximum dosage tolerated by the patient. The replication defective viruses can be administered as a relatively high amount, followed by lower maintenance dose, or the viruses can be administered in uniform dosages.

The dosage and the frequency of administration will vary with the replication defective viruses employed in the method of the invention. The amount administered to a human can vary from about 50 ng per Kg of body weight to about 1 μg per Kg of body weight, preferably about 100 ng per Kg of body weight to about 500 ng per Kg of body weight. For chimpanzee infection, $2 \times 10^7$ to $5 \times 10^7$ HBV genome equivalents (which corresponds to about 35-90 pg DNA) are required (Guidotti L. G., et al., *Science*, 284:825-29 (1999)) This corresponds to 0.7 to 1.8 pg/Kg of body weight. Optimum amounts can be determined with a minimum of experimentation using conventional dose-response analytical techniques or by scaling up from studies based on animal models of disease.

The term "about" as used herein in describing dosage ranges means an amount that has the same effect as the numerically stated amount as indicated by clearance of chronic viral infection in the host to which the replication defective viruses are administered, with an absence or reduction in the host of determinants of pathogenicity, including an absence or reduction in persistence of the infectious virus in vivo, and/or the absence of pathogenesis and clinical disease, or diminished severity thereof, as compared to individuals not treated by the method of the invention.

The dose of the replication defective viruses of the invention is specified in relation to an adult of average size. Thus, it will be understood that the dosage can be adjusted by 20-25% for patients with a lighter or heavier build. Similarly, the dosage for a child can be adjusted using well known dosage calculation formulas.

The replication defective viruses of the invention can be used in therapy in the form of pills, tablets, lozenges, troches, capsules, suppositories, injectable in ingestible solutions, and the like in the treatment of hepatitis infection in humans and susceptible non-human primates and other vertebrate animals and mammals.

Appropriate pharmaceutically acceptable carriers, diluents, and adjuvants can be combined with the replication defective viruses described herein in order to prepare the pharmaceutical compositions for use in the treatment of pathological conditions in animals. The pharmaceutical compositions of this invention contain the replication defective viruses together with a solid or liquid pharmaceutically acceptable nontoxic carrier. Such pharmaceutical carriers can be sterile liquids, such as water and oils, including those of petroleum, animal, vegetable, or synthetic origin. Examples of suitable liquids are peanut oil, soybean oil, mineral oil, sesame oil, and the like. Water is a preferred carrier when the pharmaceutical composition is administered intravenously. Physiological solutions can also be employed as liquid carriers, particularly for injectable solutions.

Suitable pharmaceutical excipients include starch, glucose, lactose, sucrose, gelatin, malt, rice, flour, chalk, silica gel, magnesium carbonate, magnesium stearate, sodium stearate, glycerol monstearate, talc, sodium chloride, dried skim milk, glycerol, propylene glycol, water, ethanol, and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. The pharmaceutical compositions contain an effective therapeutic amount of the replication defective virus of the invention together with a suitable amount of carrier so as to provide the form for proper administration to the host.

The ability of the replication defective viruses of the invention to induce protection in a host can be enhanced by emulsification with an adjuvant, incorporation in a liposome, coupling to a suitable carrier, or by combinations of these techniques. For example, the replication defective viruses of the invention can be administered with a conventional adjuvant, such as aluminum phosphate and aluminum hydroxide gel. Similarly, the replication defective viruses can be bound to lipid membranes or incorporated in lipid membranes to form liposomes. The use of nonpyrogenic lipids free of nucleic acids and other extraneous matter can be employed for this purpose.

The host or patient can be an animal susceptible to infection by a virus, and is preferably a mammal. More preferably, the mammal is selected from the group consisting of a human, a dog, a cat, a bovine, a pig, and a horse. In an especially preferred embodiment, the mammal is a human.

Another aspect of the invention includes administering nucleic acids encoding the replication defective virus of the invention with or without carrier molecules to an individual. Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids encoding replication defective virus of the invention, naked or encapsulated, directly to tissues and cells, especially muscle cells or keratinocytes, without the need for production of encoded proteins prior to administration. The technology is based on the ability of these nucleic acids to be taken up by cells of the recipient organism and expressed to produce a replication defective virus to which the recipient's immune system responds. Such nucleic acid vaccine technology includes, but is not limited to, delivery of expression vectors encoding a replication defective virus of the invention. Although the technology is termed "vaccine," it is equally applicable to immunogenic compositions that do not result in a completely curative response. Such partial-protection-inducing compositions and methods are encompassed within the present invention.

The present invention also encompasses delivery of replication defective virus as part of larger or more complex compositions. Included among these delivery systems are viruses, virus-like particles, or bacteria containing the nucleic acids encoding the replication defective virus of the invention. Also, complexes of the invention's nucleic acids and carrier molecules with cell permeabilizing compounds, such as liposomes, are included within the scope of the invention. Other compounds, such as molecular vectors (EP 696,191, Samain et al.) and delivery systems for nucleic acid vaccines are known to the skilled artisan and exemplified in, for example, WO 93 06223 and WO 90 11092, U.S. Pat. No. 5,580,859, and U.S. Pat. No. 5,589,466 (Vical patents), which are incorporated by reference herein, and can be made and used without undue or excessive experimentation.

During the replication cycle, HBV pregenomic RNA serves as the mRNA template for translation of the viral core and polymerase proteins. It is encapsidated together with the viral polymerase into a nucleocapsid consisting of around 200 subunits of the core protein. The viral envelope is densely packed with the large (L), middle (M) and predominantly small (S) viral envelope proteins. In addition to envelope proteins, the virus encodes a regulatory protein (X), all translated from subgenomic RNAs.

HBV infects only human and chimpanzees. As alternative animal models, the invention provides HBV- or HBsAg transgenic mice, which replicate or express HBV genes in the liver. Expression of the transgene from birth tolerizes dHBV-specific T cells responses in these animals.

The invention provides that hydrodynamic injection of rHBV to mimic gene expression in mouse livers circumvents the tolerization of dHBV-specific T cells response.

The invention also provides that, in HLA-transgenic mice, priming with a DNA vector encoding foreign HLA-A2 restricted epitopes activates T cell responses that subsequently localize to the liver of mice following hydrodynamic injection of recombinant HBV (rHBV). Since rHBV is expected to replicate only in hepatocytes bearing the wild type HBV and sharing the same mechanism in the viral cycle, the strong immune responses elicited by the foreign polyepitope dominates over the exhausted T cell responses present during natural HBV persistent infection.

A key question in the development of immunotherapeutic strategies against hepatitis B chronic infection is whether HBV-specific T cells can be functionally restored using vaccination or other immunomodulatory approaches. It is also important to assess whether vaccine or otherwise activated T cells can enter the liver and eliminate HBV-infected cells. In the current study, we used HBV as an immunotherapy vector to deliver a modified core protein fused with foreign immunogenic epitopes in liver cells. Following gene expression of this modified virus, functional epitope-specific T cells were attracted to liver in which they were able to control HBV gene expression in hepatocytes.

An ideal vector for gene therapy can target abnormal cells without harming healthy neighboring cells. The invention provides an artificial rHBV, with the core gene interrupted by insertion of a short sequence encoding immunodominant epitopes derived from common viruses. This modified virus was not competent for replication except in hepatocytes providing wild type viral capsids in trans. rHBV is, therefore, not expected to maintain in healthy hepatocytes, but only in cells from patients with chronic HBV replication. Once the natural HBV infection is eliminated, the rHBV pseudo-viral life is subsequently interrupted.

The 3.2-Kb HBV genome is highly compacted, with overlapping open reading frames (ORF) for structural genes and various regulatory elements. It is technically difficult to engineer this virus, mainly because of space limitation. The present invention provides that the foreign sequence in rHBV was inserted in a region located between polyadenylation signal for HBV mRNA and the start of the polymerase reading frame. No obvious cis-acting element has been found in this region that may participate to viral replication. However, a potential internal site for ribosome entry has been described. Thus, translation of the polymerase is a small probability event, with a mechanism of ribosome shunting along the messenger RNA. HBV polymerase functions in cis to find the epsilon signal in pgRNA and to initiate the viral replication. Therefore, the size of foreign insertion should be compatible with the translation of HBV polymerase. Interestingly, the rHBV in our study is similar to a naturally occurring HBV variant (ΔC-144), identified by Will H et al during fulminant hepatitis. This variant could produce 2- to 4.5-fold more progeny DNA than wild-type HBV when sufficiently complemented with wild-type core protein (Gunther, S., Piwon, N., Jung, A., Iwanska, A., Schmitz, H., Will, H. (2000) Enhanced replication contributes to enrichment of hepatitis B virus with a deletion in the core gene, *Virology* 273:286-99.) In addition, rHBV has a short viral genome that favors pgRNA packaging. It is thus expected that rHBV could dominate the cccDNA pool in the cell nucleus, leading to the inhibition of wild type HBV replication.

Increasing evidence suggests that the host immune response plays a critical role in determining the various outcomes of HBV infection. In particular, HBV-specific CD8 T-cell responses are believed to be of considerable importance in viral control and immune-mediated disease. However, during chronic infection, these responses are generally weak and narrowly focused. Virus-specific T cells from chronic patients rapidly become exhausted. T cell dysfunction has been attributed to high levels of persisting viral antigens. But in chronic patients immune responses to other pathogens remain intact. We therefore thought to design a novel therapeutic approach based on activation of non-HBV specific T cells that were further redirected to liver following rHBV injection.

In summary, this invention provides a new approach to the design of a virus with a defective replication cycle, which can be rescued by wild type virus co-infection, and which expresses foreign antigenic epitopes that contribute to the elimination of virus infected cells and then to viral clearance. The vector of the invention, by expression of epitopes derived from common pathogens, by-passes existing tolerance of virus specific T cell responses. The vector will only replicate in virus infected cells.

In a particular embodiment, this invention provides a new approach to the design of a hepatitis virus with a defective replication cycle, which can be rescued by wild type hepatitis virus co-infection, and which expresses foreign antigenic epitopes that contribute to the elimination of hepatitis virus infected hepatocytes and then to viral clearance. The vector of the invention, by expression of epitopes derived from common pathogens, by-passes existing tolerance of hepatitis virus specific T cell responses. The vector will only replicate in hepatitis virus infected hepatocytes.

According to this invention, the foreign antigenic polyepitope can break or help to break the hepatitis immune tolerance. The induced T cell responses can silence, specifically or nonspecifically, hepatitis genes through non-cytolytic mechanisms. The recombinant hepatitis virus carrying the polyepitope can be tested for replication in hepatocytes of UPA-SCID mice reconstituted with human liver cells.

*E. coli* strains carrying the following plasmids were deposited at the Collection Nationale de Cultures de Microorganismes (C.N.C.M.), 25, rue du Docteur Roux, F-75724 Paris, Cedex 15, France, and assigned the following Accession Nos.:

| Plasmid | Accession No. |
|---|---|
| prHVB1.3-IV | CNCM I-3833 |
| pCMVrHBe-IV | CNCM I-3834 |
| prHVB1.3-III | CNCM I-3832 |
| pCMVrHBc | CNCM I-4077 |
| prHBV1.3 | CNCM I-4078 |
| prHBV1.3/HBc | CNCM I-4079 |

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges including either or both of the upper and lower limits of the range, unless specifically excluded from the stated range.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (for example, amounts, temperatures, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In Vitro Assay for Recombinant HBV (rHBV) Replication

A polyepitope sequence was inserted into a 1.3 copy of HBV genome in the N-terminal part of the original capsid-encoding fragment to create the recombinant HBV (prHBV-1.3 and its derivatives-III or -IV, see FIG. 2). Co-transfection of prHBV1.3-III with the plasmid expressing capsid gene under a CMV promoter (pMAScore) to a liver cell line was carried out to initiate a replicating cycle mimicking the wild HBV replication in vitro (detection of cccDNA genome and other intermediate forms by Southern blot assay). Results are presented in FIG. 3A (detection of HBV genome in secreted viral particles by PCR).

The human hepatocytic cell line Huh7 (Nakabayashi, H., Taketa, K., MIyano, K., Yamane, T., Sato, J. (1982) Growth of human hepatoma cell lines with differentiated functions in chemically defined medium, *Cancer Res* 42(9):3858-63) was transfected with prHBV1.3-III with or without pMAS-core, with pMAS-core alone, or with pFC80 (positive control, plasmid containing two HBV genomes in tandem). Supernatants were collected and viral particles were precipitated using PEG 8000. After a DNase treatment to remove the residual plasmid DNA, particles were lysed and HBV genome was PCR amplified (PCR primers on N part of core gene and middle of HBs-encoding gene). Alternatively, the primers may be on any part of the HBV genome, more particularly, before the S gene. The results are shown in FIG. 3A. The expected fragment is detected only after cotransfection of prHBV1.3 and pMAS-core, but not after transfection of either pMAS-core or prHBV1.3 alone.

Figure 1:
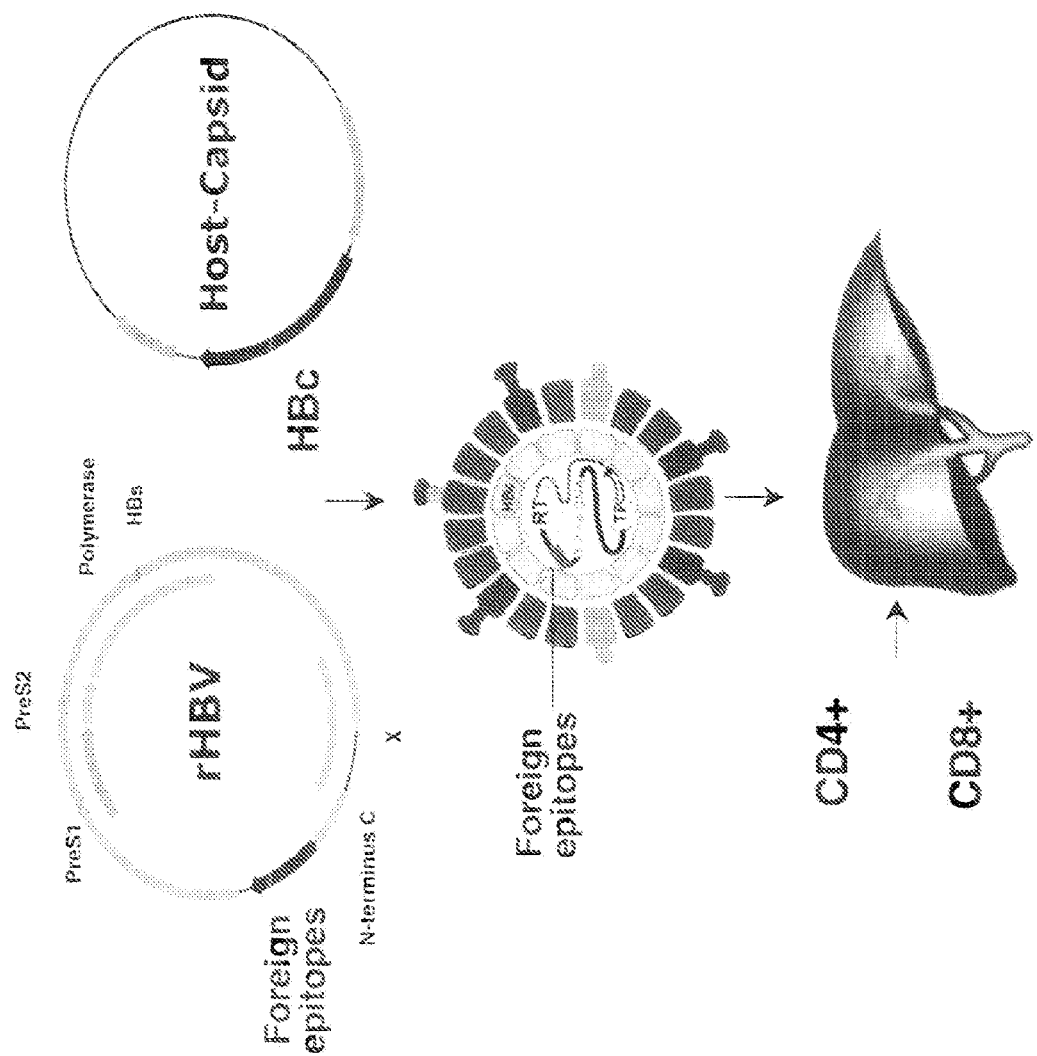
FIG. 1 is a schematic diagram of a recombinant vector designated rHBV complemented by a plasmid expressing HBc to form a pseudo-virus of the invention containing foreign epitopes, which can stimulate CD4+ and CD8+ responses to hepatocytes infected by the pseudo-virus.
Figure 2:
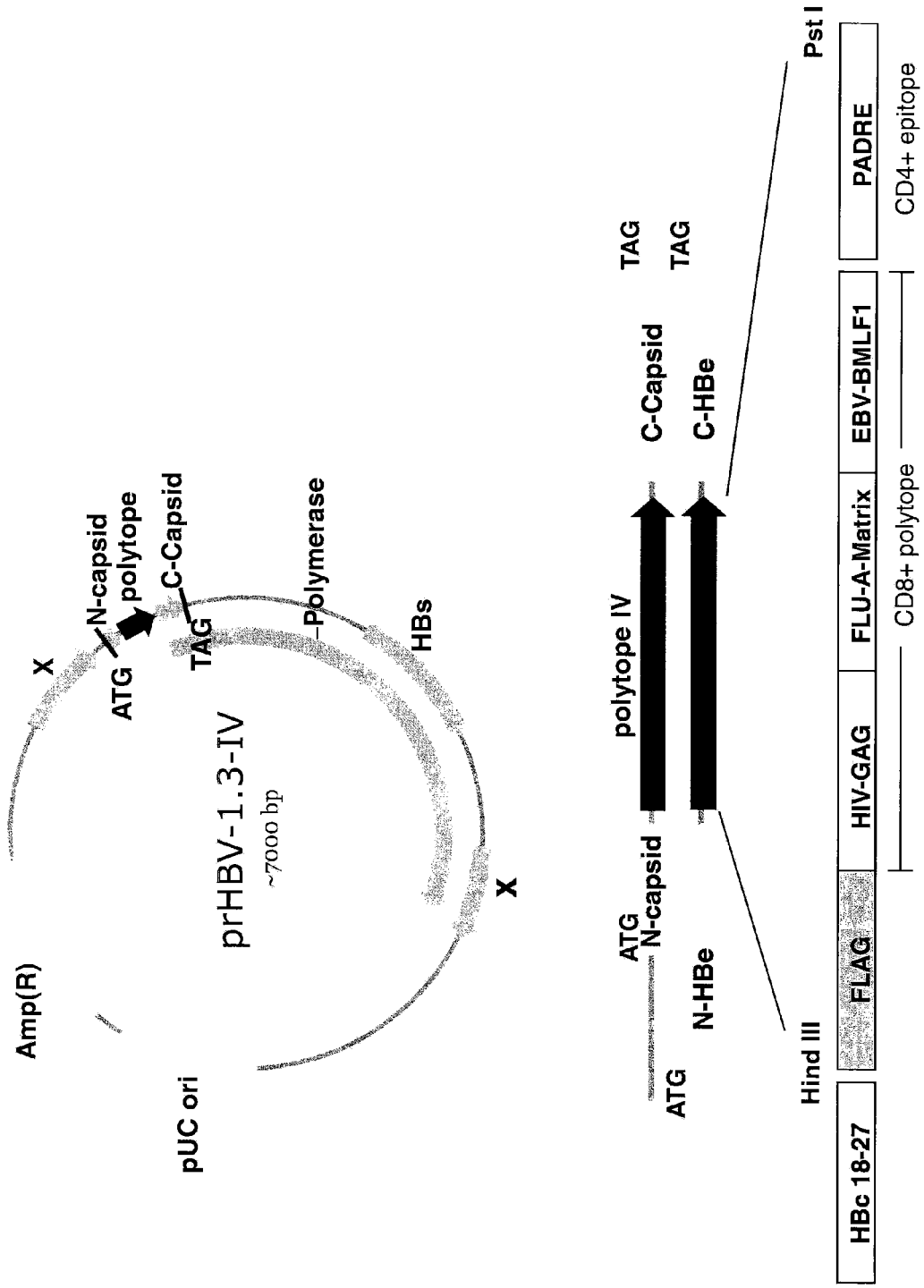
FIG. 2 depicts a construct designated prHBV-1.3-IV containing a polytope (polyepitope), as well as the construct designated polytope IV.
Figure 3:
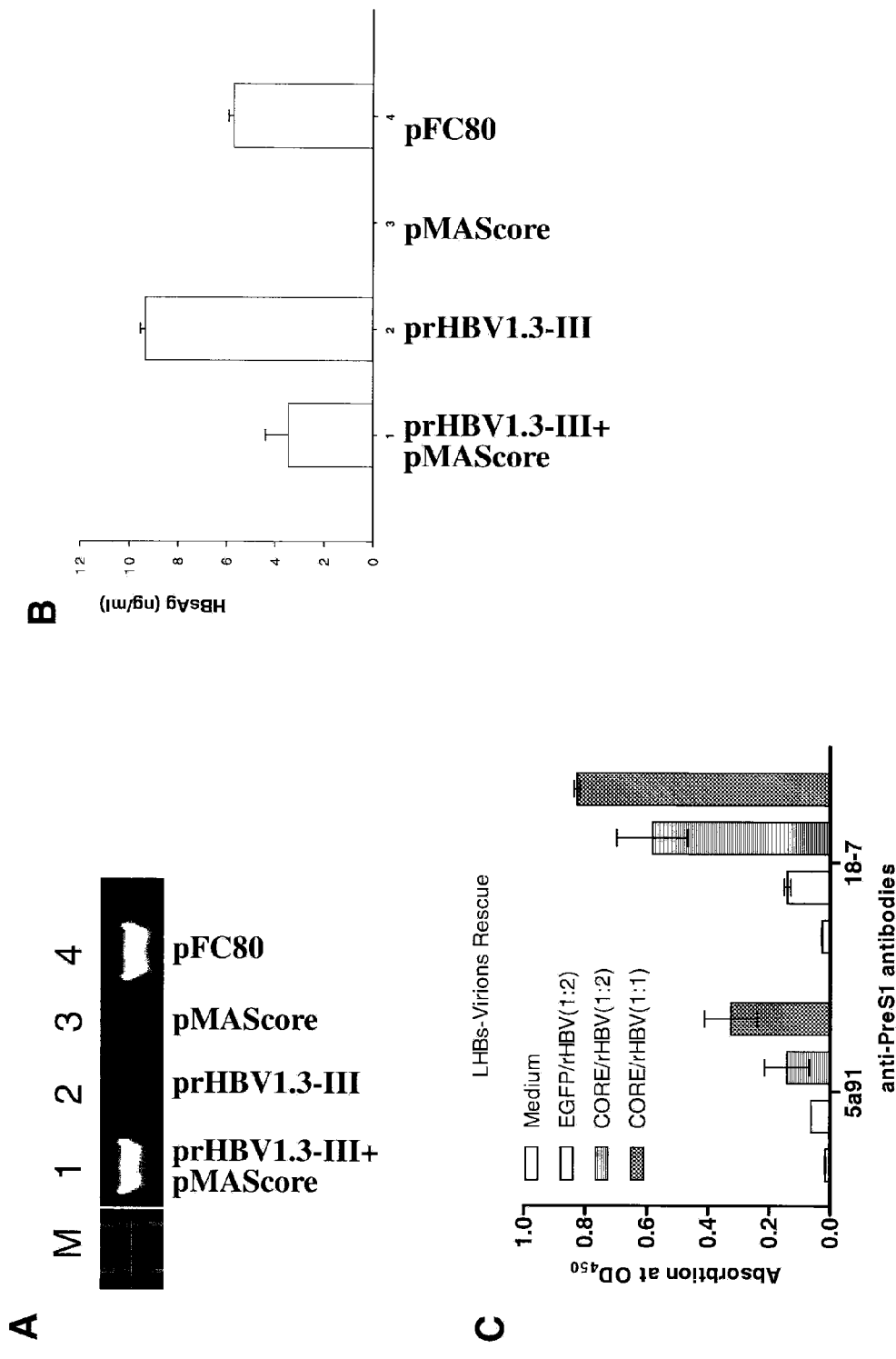
FIG. 3 depicts the rescue of rHBV DNA from a human hepatocytic cell line co-transfected with prHBV 1.3-III and a plasmid expressing the capsid (PMAS core).

Hepatitis B surface antigen (HBsAg) was also detected in supernatant from cells cotransfected with prHBV1.3 and pMAS-core or transfected with pFC80, but not after transfection of pMAScore alone (see FIG. 3B).

To assess LHBs-virion rescue, two different ratios for co-transfection (1:1 and 1:2) and a control plasmid not expressing core but EGFP were used. After co-transfection of the prHBV1.3-III and pMAScore plasmids to the hepatocytic Huh 7 cell line, supernatants of transfected cells were collected. Viral particles containing the large HBV envelope protein (LHBs) were quantified by a specific ELISA using two monoclonal antibodies specific for the large HBV envelope protein (MoAb 5a91 and MoAb 18-7) as capture antibodies and a labeled anti-HBs MoAb for detection. Results are shown in FIG. 3C. This experiment shows that expression of core is required for efficient secretion of particles containing the LHBs in a dose-dependent way. LHBs is known to be localized on the surface of 42 nm HBV Dane particles.

Example 2

In Vivo Assay for rHBV Infection

An investigation is made to determine whether the in vitro produced rHBV virion could be infectious in vivo. Since there is no small animal model, a UPA transgenic mouse with transplanted human liver tissue can be useful. (Morosan, S., et al. (2006) Liver-stage development of *Plasmodium falciparum*, in a humanized mouse model, *J Infect Dis* 193:996-1004.) For infection, a small stock of infectious rHBV is required. This will be obtained by first creating a stable HepG2 (ATCC number HB-8065) cell line expressing the rHBV genome constitutively and second by transducing this cell line with a lentiviral vector expressing the HBV core gene.

Example 3

Creation of a String of Immunodominant Epitopes

Based on the knowledge of HBV molecular biology, the space to accommodate a foreign sequence in HBV genome is limited to more or less 195 nucleotides. Due to this space limitation, a short sequence encoding foreign immuno-dominant epitopes (polyepitope) is introduced into the recombinant HBV genome in order to induce a robust immune response. Regarding the polyepitope, it is arranged with 3 $CD8^+$ T-cell epitopes combined with a promiscuous $CD4^+$ T-cell epitope (PADRE), which could universally accommodate several prevalent MHC class II molecules. For the $CD8^+$ T-cell response, considering the clinical relevance, three well known HLA-A2-restricted epitopes derived from common human viruses (HIV gag, Influenza matrix, EBV BML-F1) are chosen. Additionally, a short B-cell epitope (FLAG) is introduced into the foreign sequence as a convenient detection marker for molecular biology assays (see FIGS. 2 and 6). A HLA-A2-restricted capsid-derived epitope (core 18-27) is present in the N-terminal part of the capsid protein.

Example 4

Assessing Polyepitope Expression In Vitro

The precore-core region of HBV encodes the hepatitis core antigen (HBcAg) that self assembles to form viral capsids, and a secreted polypeptide, the hepatitis e antigen (HBeAg). These two proteins are derived by alternative initiation of translation at two in frame codons (see FIG. 2). The 16 Kd HBe protein is derived by proteolytic cleavage from a precursor protein initiated at the first initiation codon. To assess expression of the polyepitope by the recombinant HBV, the hepatoma cell line HepG2 was transfected with prHBV1.3-IV and three days later cell lysate was collected for immunoblot analysis. Detection of recombinant rHBe protein using anti-Flag monoclonal antibody is shown in FIG. 4.

Expression of the polyepitope carried by the recombinant virus was also detected after transfection of Huh7 cells with prHBV1.3 in immunofluorescence assays using anti-FLAG MoAb (see FIG. 5, panel B). Expression of HBsAg was also detected on the Huh7 cells using anti-HBs MoAb (FIG. 5, panel A). Localization of intracellular HBsAg was homogeneously dispersed in the cytoplasm, whereas the tagged recombinant HBc antigen localized in the perinuclear area with some polarization.

Example 5

Assessing Polyepitope Expression In Vivo

Expression of the polyepitope carried by the recombinant virus was also assessed after hydrodynamic injection of mice with prHBV1.3-III DNA. (Yang, P. L., et al., (2002) Hydrodynamic injection of viral DNA: a mouse model of acute hepatitis B virus infection, *Proc Natl Acad Sci USA* 99:13825-30; Pajot, A., et al. (2004) A mouse model of human adaptive immune functions: HLA-A2.1/HLA-DR1-transgenic H-2 class I/class II-knockout mice, *Eur J Immunol* 34(11):3060-9.)

Three days after injection of prHBV1.3-III DNA, the liver was collected and histochemical analysis was performed on liver sections. HBsAg expression was observed in liver cells using anti-HBs MoAb for detection (FIGS. 6A, 6C). The recombinant HBeAg carrying the foreign epitopes was detected using an anti-FLAG MoAb (FIGS. 6B, 6D). Control mice received a hydrodynamic injection of PBS.

Example 6

Assessing T-Cell Response to Polyepitope In Vivo

To evaluate the T-cell response against the foreign polyepitope, a plasmid with the polyepitope driven by CMV promoter (pCMV-rHBe) was tested by intramuscular DNA immunization (two injections) in HLA-A2/DRB1*01 transgenic mice (Pajot et al., 2004). Specific T cell responses against the foreign epitopes were analyzed by proliferation and ELISPOT assays one week after the second injection in mice. The CD4 T-cell epitope PADRE activated IFN-γ-secreting cells (FIG. 7, left panel) and was able to induce proliferation of lymphocytes from immunized mice (FIG. 7, right panel).

The Flu matrix-derived epitope was the most frequently recognized among the $CD8^+$ epitopes present in the polyepitope (4/6 responder mice). T cell responses to EBV and core-derived epitopes were found in only one mouse. The immunodominant response to the Flu-derived epitope probably resulted from competition between peptides for fixation to the HLA-A2 molecule. This was confirmed in a second experiment with 8/10 immunized mice having T cell responses to the Flu-derived epitope and only 3/10 to the HBc 18-27-derived HLA-A2 epitope (FIG. 8, left panel). Nevertheless the Gag- and EBV-derived epitopes activated T cells were detectable after one week in vitro stimulation of splenocytes with the corresponding peptides before IFN-γ ELISPOT assays.

T cell responses to the Flu matrix epitope was also quantified using a HLA-A2-tetramer carrying the Flu epitope in splenocytes from DNA-immunized mice (two injections of pCMV-rHBe). Flu-specific T cells represent around 10% of CD8+ T cells from the spleen (FIG. 8, right panel).

The immune response to the polyepitope expressed by the recombinant virus was also assessed after one hydrodynamic injection of prHBV1.3-III into HLA-A2/-DRB1*01 transgenic mice. IFN-γ ELISPOT assays were performed on splenocytes taken 16 days after hydrodynamic injection. T cells specific for the Flu matrix epitope were detected in 4 out of 5 mice (FIG. 9). In this experiment, 2 mice were immunized by intramuscular injection with prHBV1.3-III as control (mouse 6 and 7). Intravenous injection of recombinant HBV is less immunogenic than intramuscular injection. This could be related to the route of injection and to the expression of antigens in the liver, which is known to be a tolerogenic organ.

Example 7

Assessing T-Cell Response to Polyepitope In Vivo and Localization of Flu-Specific T-Cells Groups of HLA-A2/DRB1*01 mice (Pajot et al., 2004) were immunized intramuscularly with the plasmid pCMV-rHBe to prime T cell responses specific for foreign epitopes. Fifteen days after the priming, mice were injected by the hydrodynamic route with either prHBV1.3 or pCMV-βGal (control plasmid), or by intramuscular injection of pCMV-rHBe. FIG. 10A presents a graphical depiction of the immunization time-line.

Liver infiltrating lymphocytes were prepared and stained with anti-CD8, anti-CD3 antibodies and with Flu-tetramers for FACS analysis. Non-immunized control mice were used as a control. Quantification of CD8 T cells was performed after staining with anti-CD8, anti-CD3 antibodies. CD3+, CD8− cells were considered as CD4+ T cells. FACS analysis showed that the number of CD8+ T cells infiltrating liver was much higher in mice receiving prHBV1.3 (FIG. 10B, panel B3, 37.4%) compared to those receiving pCMV-βGal (FIG. 10B, panel B2, 7.31%) and non-injected mice (FIG. 10B, panel B1, 5.11%). Flu-specific T cells staining is shown on the lower panels for non-immunized mice, for mice receiving pCMV-βGal or for mice receiving prHBV1.3 by hydrodynamic injection. For mice receiving prHBV1.3, 17% of T cells are Flu-specific. These cells represent 42% of CD8+ T cells. A comparable analysis was performed on spleen-derived lymphocytes.

T cells and Flu-specific T cells were localized in spleen and liver. Results are shown in FIG. 10C. A strong increase of the % of CD8+ T cells infiltrating liver and to a lesser extent in spleen was shown after hydrodynamic injection of prHBV1.3, compared to mice receiving pCMV-βGal or pCMV-rHBe. In contrast, the percentage of CD4 T cells in spleen or liver is comparable for the three groups of mice. In the liver, the majority of the lymphocyte population consists of Flu-specific CD8+ T cells, as detected by tetramer-staining. These experiments indicate that after hydrodynamic injection of prHBV1.3, the Flu-specific T lymphocytes re-localize from the spleen to the liver.

Example 8

Construction of rHBV Genome Bearing a Foreign Polyepitope prHBV1.3 was constructed in the HBV ayw3 genotype background (Accession No. V01460, GenBank). The invention provides a plasmid of pCMV-Pol bearing a full length of polymerase gene and all the downstream viral elements in the HBV genome. Sequence adjacent to the start codon of the polymerase gene was modified as, 5'CCGAACATGGAG (SEQ ID NO: 13), consistent with the Kozak rule. Additionally, two restriction enzyme sites (Hind III and Pst I) were arranged prior to an ATG start codon, in order to adopt a 180 nucleotide fragment coding for the foreign polyepitope (synthesized by Genscript Corp., Piscataway, N.J.), that resulted in a new plasmid named pCMV-F-Pol. The embedded foreign sequence (F) shares the same reading frame with the remaining HBV core fragments (FIG. 11).

To generate 1.3 copies of the rHBV genome, a DNA fragment covering nt1075 to nt1981 of the HBV genome was PCR amplified, and took the place of the CMV promoter in the parental plasmid by digestion with Nru I and Hind III. pCMV-rHBc encodes the recombinant foreign antigen (rHBc) driven by CMV promoter. pMAS-C comprises the HBV core gene, under a CMV promoter. The plasmid prHBV1.3HBc has an additional expression cassette of HBV core protein. Briefly, a SV40 early promoter sequence (from pcDNA3, Invitrogen) was PCR amplified and inserted downstream of the rHBV genome in prHBV1.3, being separated by an f1 origin. The HBV core gene, together with a BGH polyA processing site, was further subcloned under the SV40 early promoter (FIG. 11D). Plasmids were purified using Qiagen DNA purification columns (Endofree Plasmid Kit™; Qiagen, Hilden, Germany).

PCR amplification was performed by extracting viral DNA from mice sera with QIAamp DNA Blood Kit™ (Qiagen). The extracted DNA was treated with Pvu II digestion, to linearize the residual prHBV1.3 DNA contaminant plasmid. DNA bands covering an area of 2.5-3.5 kb in the gel after electrophoresis were purified as a template for PCR amplification, with the specific primers (3042F, 5' GTGGAGCCCT-CAGGCTCAGGG (SEQ ID NO: 14); 459R, 5'GGA-CAAACGGGCAACATACC (SEQ ID NO: 15)).

rHBV was constructed to share most of its features with the wild type HBV genome (FIG. 11A, B), with the exception of a 325-bp fragment within the HBV core gene, which was removed and substituted for by an in-frame 190-bp foreign sequence encoding a string of immunodominant T cell epitopes (FIG. 11C). As a result of the deletion, the open reading frame of the polymerase gene was shifted forward by 135 bp, bringing the ATG of the pol ORF much closer to the 5' CAP in the HBV pregenomic RNA (FIG. 11A, B). The ATG starting signal of the polymerase gene was optimized according to Kozak's rules, in order to facilitate ribosome entry for the translation.

The foreign polyepitope was engineered with three immunodominant CD8+ T-cell epitopes combined with a promiscuous CD4+ T-cell epitope (PADRE) which could universally match up most of prevalent MHC class II molecules. Considering the clinical relevance, three well-known HLA-A2-restricted epitopes derived from common human viruses (HIV gag, Influenza matrix, EBV BML-F1) were chosen, in order to elicit a vigorous immune response in vivo. In this construct, the well known HBc18-27 HLA-A2 restricted epitope present in the amino-terminal part of the core gene was preserved. Additionally, a short B-cell epitope (FLAG) was introduced at the N-terminal part of the foreign sequence as a convenient detection marker (FIG. 11C). The core gene of HBV encodes two types of protein, the pre-core/HBeAg and the core proteins, which are translated from two distinct messenger RNA species. Two in-frame start codons are used for the translation of the two types of proteins. The core protein is the major constituent of the nucleocapsid, which carries HBcAg. HBeAg is a secreted protein produced by post-translational modifications of a precursor protein initiated at the first ATG of the core ORF. Therefore, a chimeric antigenic protein referred to as rHBc could be generated, with the foreign polyepitope fused in frame with the truncated HBe/capsid proteins (FIG. 11C).

prHBV1.3/HBc is a plasmid with two expression cassettes, one for rHBV genome expression and the other for expression of the capsid protein (FIG. 11D). The plasmid prHBV1.3 bears 1.3 copies of the rHBV genome only. Both plasmids were used for replication assays in vitro and in vivo. In pCMVrHBc, the expression of the rHBc is driven by the CMV early gene promoter. A polyadenylation signal for mRNA is provided by HBV sequences (FIG. 11D). This plasmid was among those used to immunize mice.

Example 9

Expression of the Recombinant Protein Carrying the Polyepitope

The expression of the chimeric rHBc protein was first studied in a cell culture system. The human hepatoma cell lines HepG2 and Huh 7 were maintained in Dulbecco's Modified Eagle's Medium (DMEM) supplemented with 10% fetal calf serum (FCS). Polyethylenimine (PEI) was purchased from Sigma-Aldrich (St. Louis, Mo.), and used for transient transfection assays. Cell culture supernatant was harvested at day four post PEI transfection and used to prepare rHBV viral DNA.

The immunofluorescence experiments were performed on HepG2 cells three days after DNA transfection, using published methods. Briefly, cells were fixed with 4% paraformaldehyde in phosphate buffered saline (PBS). Cells or tissue sections were incubated with anti-Flag mAb (1084; 1:100; Sigma-Aldrich) or anti-HBs mAb (3E7; 1:100; Dako, Glostrup, Denmark) at 4° C. overnight. After extensive washing, the bound primary antibody was detected by Alexa 488-labeled rabbit anti-mouse immunoglobulin G (Molecular Probes, Carlsbad, Calif.).

Histological staining was performed on freshly prepared mouse liver, frozen in isopentane pre-cooled in liquid nitrogen, and embedded in OCT compound in cryomolds. Five micron thick cryostat sections were mounted on superfrost plus slides and stored at −80° C. Before staining, slides were fixed in ice-cold acetone for 5-10 minutes. Liver sections were stained with hematoxylin and eosin, or immunostained with FITC labeled anti-HBs antibody (1:50; ab32914, Abcam, Cambridge, Mass.). After extensive washing with PBST and PBS, the liver sections were mounted with an anti-fade reagent containing DAPI.

After transient transfection of prHBV1.3 plasmid into hepatocyte-derived HepG2 cell line, a recombinant protein with the expected size (15 kD) was detected by Western blot in cell lysates using anti-FLAG antibody (FIG. 12A). The rHBc protein was also detected by antibody staining and immunoflorescence in the cytoplasm of HepG2 transfected cells, using anti-Flag antibody (FIG. 12B, lower panel). Expression of HBV envelope proteins in cells transfected with the rHBV was detected using an antibody against HBsAg, which is the major antigenic determinant of the envelope (FIG. 12B, upper panel). Interestingly, labeling of intracellular HBsAg was homogeneously dispersed in the cytoplasm, whereas the rHBe localized in the perinuclear area, with polarization. In addition, HBsAg particles carrying the HBV large envelope protein (L) were also detected by ELISA in cell culture supernatant after prHBV1.3 transfection (see below and FIG. 12D).

Example 10

Rescue of rHBV Particles and Replication by In Trans Encapsidation rHBV is a defective HBV virus owing to the disrupted core gene. However, it replicates and maintains in hepatocytes with the help of a wild type HBV capsid produced in trans in infected hepatocytes. The invention provides replicative forms of rHBV viral DNA in cell culture supernatant, e.g., from the Huh-7 hepatic cell line, after transfection of prHBV1.3/HBc plasmid encoding both rHBV genome and capsid protein but not after transfection of prHBV1.3.

Viral DNA associated with rHBV virions was extracted from the cell culture supernatants of HepG2- or Huh 7-transfected cells. Briefly, the virus particles in the medium were precipitated by incubation with 10% PEG 8000 overnight on ice. After centrifugation at 11,000 rpm for 30 minutes, the pellets were suspended in buffer (100 mM Tris/HCl (pH 8.0)), and further treated with DNase I (Invitrogen, Carlsbad, Calif.) in the presence of 10 mM $MgCl_2$. After proteinase K digestion (1 mg/ml), the viral DNA was precipitated using ethanol and glycogen as carrier. A Southern blot assay was performed by methods known in the art, with a $^{32}P$ labeled probe specific to the HBV genome.

Following DNA extraction and HBV-specific probe hybridization in Southern blot assays, the viral DNA was detected, in both its typical relaxed circular (RC) and double stranded linear (DSL) forms (FIG. 13A), indicating normal packaging and maturation of rHBV nucleocapsid. In addition, the core-rescued rHBV exhibited a more efficient viral cycle than wild type HBV. Upon co-transfection with pwtHBV, the replicative intermediates of rHBV were expressed at significantly greater levels than the wild type replicative forms, indicating the rescue, packaging, and maturation of rHBV virions in the presence of wild type capsid protein (FIG. 13C).

Hydrodynamic injection technology (Liu, F., (1999) *Gene Therapy*) was used to introduce the rHBV genome into mouse liver. Four days after hydrodynamic injection of prHBV1.3 through the tail vein, both recombinant antigenic protein (rHBc) and HBV envelope proteins were detected in mouse liver by immunoflorescence staining of liver sections with anti-FLAG and anti-HBs antibodies respectively (FIG. 12C). Taken together, these experiments suggest that HBV envelope proteins and rHBc protein carrying the polyepitope are expressed after in vitro or in vivo transfection of the plasmid bearing 1.3 copies of rHBV genome.

In addition, recombinant rHBV virions were detected in the sera of mice receiving both prHBV1.3 and pMAS-C by hydrodynamic injection, using specific PCR amplification at day four after the injection. In contrast, in the absence of pMAS-C, injection of prHBV1.3 alone or with co-injection of a plasmid encoding beta-galactosidase (pCMV-βGal), no viral DNA was detected (FIG. 13D). Therefore, the rHBV genome can be complemented in trans by capsid proteins in vitro and in vivo giving rise to complete viral particles containing replicative forms of viral DNA.

The large envelope protein (L) is known to be localized on the surface of 42 nm HBV complete viral particles and on the filamentous sub-viral particles present in the sera of HBV-infected individuals. To demonstrate that complete viral particles can be produced from the rHBV genome, cotransfection experiments of prHBV1.3 and a plasmid encoding the core protein (pMAS-C) in Huh-7 cell line were performed. Cotransfection with the core-encoding plasmid resulted in an increase in the production of L protein-carrying particles in cell culture supernatant, compared with transfection of prHBV1.3 alone or cotransfection with pIRES-GFP as control. The increase in L protein production was dose-dependent as shown in a specific ELISA using two different monoclonal antibodies recognizing the amino-terminal part of L protein (FIG. 13B).

Example 11

Activation of Polyepitope-Specific T-Cell Responses

IFN-γ producing splenocytes were quantified by ex vivo Elispot assays after stimulation with peptide, as known in the art. Briefly, 96-well nitrocellulose HA plates (Millipore, Bedford, Mass.) were coated by incubation overnight at 4° C. with capture antibody against IFN-γ (551216; BD Pharmingen, San Diego, Calif.). Freshly isolated splenocytes ($10^6$/well) were incubated with individual peptide at a concentration of 1 μg/ml in supplemented α-MEM medium for 24 hours. Spots were developed by a secondary biotin-conjugated antibody (554410; BD Pharmingen, San Diego, Calif.) and alkaline phosphatase conjugated streptavidin (Roche, Basel, Switzerland). A Zeiss Elispot automatic counter was used to score the number of spots. The response was considered positive if the median number of spot-forming cells (SFC) in triplicate wells was at least twice that in control wells containing medium alone.

For the proliferation assay, splenocytes ($10^6$ cells/well) were incubated with 20 μg/ml of peptide for three days in supplemented HL1 serum-free medium (Biowhitaker, Walkersville, Md.). (Pajot et al., 2004.) Cells were pulsed for the final 16 h with 1 μCi of ($^3$H)-thymidine per well. The incorporated radioactivity was measured on a micro-β counter.

To evaluate T-cell responses against the foreign polyepitope, a DNA plasmid encoding rHBc (pCMV-rHBc, as described in Example 1) was used to immunize HLA-A2/DR1 transgenic mice. (Pajot et al., 2004.) Two weeks after intramuscular injection, nine of the ten mice tested mounted epitope-specific T cell responses, as detected using ex vivo IFNγ-ELISPOT assays (FIG. 14A).

The Flu matrix-derived epitope is obviously the most frequently recognized and most powerful among the three foreign CD8$^+$ T cell epitopes (9 out of 10 responder mice). Flu-specific T cell response even dominated over the response to the well-described capsid-derived HBc18-27 HLA-A2 epitope that is present in the N-terminal part of the protein. The immunodominant response to the Flu-derived epitope probably resulted from competition between peptides for fixation to the HLA-A2 molecule. Nevertheless, Gag- and EBV-specific T cells were detectable after one week in vitro stimulation of splenocytes with individual peptides. T cell responses to the Flu matrix epitope were also quantified using a HLA-A2-pentamer (ProImmune, Oxford, UK) carrying the Flu peptide to label splenocytes from DNA-immunized mice. Accordingly, Flu-specific T cells represent around 10% of CD8$^+$ T cells from the spleen (FIG. 14B, right panel).

Mice receiving pCMV-rHBe injection also developed T helper responses against the MHC class II-restricted epitope PADRE, as demonstrated by both I IFNγ-ELISPOT assay (FIG. 14A) and specific proliferation observed in five out of six immunized mice, upon stimulation of splenocytes with PADRE peptide (FIG. 14C).

Example 12

Retargeting Polyepitope-Specific T cell Responses to Liver

Mice were perfused with 20 ml PBS via ventricle route. The liver was smashed with a syringe plunger in a 100 μm cell strainer (100 μm Nylon, BD, Franklin Lakes, N.J.). Cell pellets were resuspended in 15 ml of 40% Purcell (Sigma, St. Louis, Mo.) and centrifuged at 2000 rpm for 20 minutes, to remove the hepatocyte clumps. The intrahepatic lymphocytes in the pellets were further purified through a Ficoll gradient centrifugation as for the separation of mouse splenocytes. Freshly isolated lymphocytes were stained by PerCP-labeled anti-CD3, APC-labeled anti-CD8 antibodies, or by PE-labeled HLA class I tetramer conjugated with Flu peptide.

For FACS analysis, at least 10000 events gated among the population of interest were analyzed on a FACSCalibur cytometer using CellQuest program (BD Biosciences, Franklin Lakes, N.J.). To demonstrate that rHBV co-maintains with wild type HBV virus in liver, and in the absence of a mouse model of HBV infection and replication, the invention provides a protocol of rHBV-based active immunotherapy in HLA-A2/DR1 transgenic mice (FIG. 15A).

HLA-A2/DR1 mice were immunized by intramuscular injection of plasmid pCMV-rHBc at day 0 to prime polyepitope-specific T cell responses in periphery. Two weeks later, prHBV1.3 was injected via a hydrodynamic route to bypass hepatocyte infection and mimic HBV replication in liver. (Yang, P., Althage, L. A., Chung, J., Chisari, F. V. (2002) Hydrodynamic injection of viral DNA: a mouse model of acute hepatitis B virus infection, Proc Natl Acad Sci USA 99:13825-30.) Thus, rHBV can be expressed in liver cells with the encoded foreign antigen being processed into peptides and presented in situ providing, in turn, intrahepatic targets for a CD8$^+$ T cell response. pCMV-βGal was used as a control plasmid for hydrodynamic injection.

Following priming and hydrodynamic injection of prHBV1.3, mice mounted a vigorous intrahepatic T-cell response, with a large number of CD8$^+$ T lymphocytes infiltrating the liver. CD8$^+$ T lymphocytes accumulated in the mouse livers, as detected by FACS analysis of liver-infiltrating lymphocytes taken at days 3, 4, and 7. At day 7, the percentage of liver-infiltrating CD8$^+$ T cells represented up to 37.4% of total lymphocytes in mice receiving prHBV1.3, compared to mice receiving pCMV-βGal (7.31%) and to non immunized mice (5.11%) (FIG. 15B). 17% of the T cells, representing 42% of the total liver-infiltrating lymphocytes, in the mice that received prHBV1.3 were Flu-specific. In comparison, only 0.36% of the Flu-specific CD8$^+$ T cells primed by intramuscular injection were present in the liver seven days after pCMV-βGal hydrodynamic injection.

FIGS. 15C and 15D demonstrate the relative distribution of CD8$^+$ and CD4$^+$ T cells in the livers and spleens from groups of primed mice receiving either prHBV1.3 or pCMV-βGal by hydrodynamic injection, or receiving two intramuscular injections of pCMV-rHBc. A strong increase in the percentage of CD8$^+$ T cells was observed in the liver and, to a lesser extent, in the spleens of mice after hydrodynamic injection of prHBV1.3, compared to mice receiving pCMV-βGal and to mice receiving pCMV-rHBc only.

Remarkably, a large increase in the percentage of Flu-specific CD8$^+$ T cells was observed in the livers of mice receiving prHBV1.3. Following immunization, Flu-specific CD8$^+$ T cells comprised a very high percentage of hepatic lymphocytes, compared to the percentage of splenic lymphocytes ($p=0.0002$). In contrast, the percentages of CD4$^+$ T cells in the spleen and the liver were not significantly different in the three groups of mice. In the presence of the vigorous CD8+ T cell response, the CD4+ T cell reservoir was relatively reduced in the liver, but not in the spleen. These experiments demonstrate that the majority of Flu-specific peripheral CD8+ T lymphocytes relocalized to the liver following rHBV-based active immunization.

The increase in the percentage of total lymphocytes derived after immunization reached statistical significance in both the liver and the spleen. As shown in FIG. 15C, the percentage of CD8+ lymphocytes observed in the livers of mice receiving pCMVrHBe priming followed by prHBV1.3 hydrodynamic injection was significantly higher than in the livers of mice receiving pCMVrHBe priming followed by pCMVβGal hydrodynamic injection (p=0.0001), and significantly higher than mice injected twice with pCMVrHBe via the intramuscular route (p=0.0009).

A similar increase in the percentage of CD8+ lymphocytes observed in the spleens of mice receiving pCMVrHBe priming followed by prHBV1.3 hydrodynamic injection was significantly higher than in the spleens of mice receiving pCMVrHBe priming followed by pCMVβGal hydrodynamic injection (p=0.0011), and significantly higher than mice injected twice with pCMVrHBe via the intramuscular route (p=0.0114).

Example 13

Non-Cytolytic Control of HBV Gene Expression in Liver Mediated by Polyepitope-Specific T Cells CD8+ T cells are the major population in hepatic infiltrates on day seven after hydrodynamic injection, as described above. Further analysis of the liver infiltrates was performed by histochemical analysis of liver sections taken four days after prHBV1.3 injection (FIG. 16A). A remarkable infiltration of inflammatory cells was observed in the liver, and was predominantly centered into clusters of various sizes, suggesting that they developed quickly to form inflammatory foci. The presence of these infiltrates was dependant on priming peripheral T cell responses, as few cell clusters were found in liver sections taken from mice receiving hydrodynamic injection of prHBV1.3 without previous priming. Little or no clustered infiltrates were observed in mice receiving pCMV-rHBe priming followed by pCMV-βGal hydrodynamic injection (FIG. 16A).

Flu-specific T cells were further phenotyped as CD44+, CD62L$^{low}$, and CD69$^{high}$ (FIG. 16B), corresponding to activated or effector memory T cells undergoing an in vivo expansion. Upon an ex vivo stimulation by Flu peptide, these cells, freshly isolated from liver, produced mostly INFγ but also produced TNFα, detected by intracellular staining (FIG. 16C). Around 58% of CD8+ T cells were positive for surface staining with CD107a, a marker of cellular degranulation (FIG. 16C). Taken together, these data demonstrate that the liver infiltrating cells were predominantly functional CD8+ effector T cells.

Knowing that HBV gene expression in liver is susceptible to a non-lytic control by IFN-γ-secreting T cells following antigen recognition, we monitored the expression of rHBV expression in the liver and sera of mice. Four days after prHBV1.3 hydrodynamic injection intrahepatic expression of HBsAg was undetectable in mice receiving pCMV-rHBe priming (FIG. 16D, left panel) compared to mice receiving prHBV1.3 only (FIG. 16D, right panel). Accordingly a 100 fold decrease in HBsAg was observed in sera of mice in which T cells were primed before prHBV1.3 injection (FIG. 16E). In contrast, in the absence of peripherally primed T cells, mice exhibited a strong HBsAg expression after prHBV1.3 hydrodynamic injection. HbsAg expression was demonstrated by immunofluorescence staining of liver sections (FIG. 16D, right panel) and HbsAg measurement in sera using a commercial detection kit (Monolisa HBsAg ULTRA, Bio-Rad) (FIG. 16E, left panel). Taken together these experiments demonstrate a rapid non-cytolytic control of rHBV gene expression by polyepitope-activated CD8+ T cells.

These infiltrating T cells can hypothetically be responsible for liver injury. However, no significant increase in the injury marker ALT was observed in the sera of mice receiving prHBV1.3 via hydrodynamic injection, as compared to those receiving pCMV-βgal as a control, four days following prHBV1.3 hydrodynamic injection (FIG. 16F). At day four post hydrodynamic injection, the mean serum alanine transferase (ALT) level was 94.18±30.33 mU/ml in the 11 mice receiving rHBV-based immunization. In comparison, the serum ATL levels remained normal in mice receiving pCMV-rHBc priming followed by pCMV-βGal hydrodynamic injection (mean=38.00±5.35), while a striking increase was observed in the sera of mice with Concanavalin A-induced acute hepatitis (FIG. 16F). (Zhu, R., et al. (2007) The Pro-Th1 cytokine IL-12 enhances IL-4 production by invariant NKT cells: relevance for T cell-mediated hepatitis, J Immunol 178: 5435-42.) It therefore suggests that, in the presence of the peripherally built-up T cell response, expression of rHBV rapidly attracted T cell response in liver without raising a major liver injury.

Example 14

Active Immunotherapy in HBsAg Transgenic Mice

The invention further demonstrates organ-specific viral targeting and expression of the pseudo-viruses of the invention, using a transgenic mouse lineage expressing HBV envelope proteins in liver and secreting HBsAg in sera. This lineage was previously back-crossed with HLA-A2 transgenic mice and is devoid of murine MHC class 1 molecules. The HLA-A2/DR1 (HLA-A02.01/DR1-transgenic, H-2 class I/class II KO) and HBsAg/HLA-A2 transgenic mice used in this study were bred in the animal facilities of Institut Pasteur. (Pajot et al., 2004.)

The HBsAg/HLA-A2 double transgenic lineage (H-2 class I KO) is endowed with HLA-A2 background and produces HBsAg in mouse liver following transgene expression. Intramuscular DNA immunization was carried out by injecting 100 µg of plasmid DNA into regenerating (i.e. cardiotoxin-treated) tibialis anterior muscles. For hydrodynamic injection, female mice around 12-15 weeks old were used. Briefly, 25 µg of plasmid DNA was injected through the tail vein in a volume of PBS equivalent to 8% of the mouse's body weight. The total volume was delivered within five seconds. Mice were bled and sera assayed for HBsAg by specific ELISA at indicated times. All experiments involving mice were performed according to European guidelines.

Following priming and hydrodynamic injection, mice were bled weekly to monitor HBsAg concentration in sera. A decrease in HBsAg in sera was first observed two weeks after priming and was followed by a second sharp decrease in all mice examined one to two weeks after prHBV1.3 hydrodynamic injection (FIG. 17B). The decrease after priming corresponds to the influx of polypeptide specific T cells from the circulation to the liver. The decrease in HBsAg reached up to 90%, compared to the starting level in some of the mice tested (FIG. 17B). In contrast, in mice receiving pCMV-βGal as control, no significant HBsAg decrease was observed following hydrodynamic injection (FIG. 17C).

Clearance of HBsAg was not complete, and antigen level fluctuated around 25% of basal level during a two-month follow up. HbsAg clearance was strong and long-lasting, however, when compared to the pCMV-βGal control animals eight weeks after immunization (p<0.0001).

We have previously shown that HBV mRNA in the liver is susceptible to down regulation by INF-γ secreted by HBsAg-specific vaccine-activated T cells. (Mancini-Bourgine et al., 2004.) Mice with HBsAg/HLA-A2 backgrounds transgenic for HbsAg also display an antiviral response to rHBV-based active immunization.

The clearance of HBsAg demonstrated by the methods of the invention is likely to be related to the non-HBV, polyepitope specific influx of Flu-specific T cells into the liver and to a bystander effect of INFγ-secreting T cells on HBsAg-expressing hepatocytes. This suggests that these functional effector T cells not only control rHBV expression, as shown in FIG. 16E, but also demonstrates HBV transgene expression in the liver.

In summary, the instant application presents a novel, efficient, and feasible strategy for the use of active immunization for the treatment of persistent viral infections, satisfying a long-felt need in the art.

Throughout this application, the terms "rHBe" and "rHBc" refer, without distinction, to the translational products of the modified preCC open reading frame.

REFERENCES

The following references are cited herein. The entire disclosure of each reference cited below, and also of those cited above, is relied upon and incorporated by reference herein.

1. Bertoletti, A., and A. J. Gehring. 2006. The immune response during hepatitis B virus infection. J Gen Virol 87:1439-49.
2. Chisari, F. V., and C. Ferrari. 1995. Hepatitis B virus immunopathogenesis. Annu Rev Immunol 13:29-60.
3. Ganem, D., and A. M. Prince. 2004. Hepatitis B virus infection—natural history and clinical consequences. N Engl J Med 350:1118-29.
4. Guidotti, L. G., and F. V. Chisari. 2001. Noncytolytic control of viral infections by the innate and adaptive immune response. Annu Rev Immunol 19:65-91.
5. Gunther, S., N. Piwon, A. Jung, A. Iwanska, H. Schmitz, and H. Will. 2000. Enhanced replication contributes to enrichment of hepatitis B virus with a deletion in the core gene. Virology 273:286-99.
6. Mancini, M., M. Hadchouel, H. L. Davis, R. G. Whalen, P. Tiollais, and M. L. Michel. 1996. DNA-mediated immunization in a transgenic mouse model of the hepatitis B surface antigen chronic carrier state. Proc. Natl. Acad. Sci. USA 93:12496-12501.
7. Mancini-Bourgine, M., H. Fontaine, D. Scott-Algara, S. Pol, C. Brechot, and M. L. Michel. 2004. Induction or expansion of T-cell responses by a hepatitis B DNA vaccine administered to chronic HBV carriers. Hepatology 40:874-82.
8. Morosan, S., S. Hez-Deroubaix, F. Lunel, L. Renia, C. Giannini, N. Van Rooijen, S. Battaglia, C. Blanc, W. Eling, R. Sauerwein, L. Hannoun, J. Belghiti, C. Brechot, D. Kremsdorf, and P. Druilhe. 2006. Liver-stage development of *Plasmodium falciparum*, in a humanized mouse model. J Infect Dis 193:996-1004.
9. Rehermann, B., and M. Nascimbeni. 2005. Immunology of hepatitis B virus and hepatitis C virus infection. Nat Rev Immunol 5:215-29.
10. Yang, P. L., A. Althage, J. Chung, and F. V. Chisari. 2002. Hydrodynamic injection of viral DNA: a mouse model of acute hepatitis B virus infection. Proc Natl Acad Sci USA 99:13825-30.
11. Nakabayashi, H., K. Taketa, K. Mlyano, T. Yamane, and J. Sato. 1982. Growth of human hepatoma cell lines with differentiated functions in chemically defined medium. Cancer Res. 42(9):3858-63.
12. ATCC number HB-8065.
13. Pajot, A., M. L. Michael, N. Fazilleau, V. Pancre, C. Auriault, D. M. Ojcius, F. A. Lemonnier, and Y. C. Lone. 2004. A mouse model of human adaptive immune functions: HLA-A2.1/HLA-DR1-transgenic H-2 class I/class II-knockout mice. Eur J Immunol. 34(11):3060-9.

Annex 1

Sequence for prHBV-1.3-III (polyepitope (polytope) sequence shadowed)

(SEQ ID NO: 16)

```
GACGGATCGGGAGATCTCCCGATCCCCTATGGTCGACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCAATCTAAGCAGGCTTTCACTTTCTCGCCAACTTACAAGGCCTTTCTG

TGTAAACAATACCTGAACCTTTACCCCGTTGCCCGGCAACGGCCAGGTCTGTGCCAAGTGTTTG

CTGACGCAACCCCCACTGGCTGGGGCTTGGTCATGGGCCATCAGCGCATGCGTGGAACCTTTTC

GGCTCCTCTGCCGATCCATACTGCGGAACTCCTAGC

CGCTTGTTTTGCTCGCAGCAGGTCTGGAGCAAACATTATCGGGACTGATAACTCTGTTGTCCTA

TCCCGCAAATATACATCGTTTCCATGGCTGCTAGGCTGTGCTGCCAACTGGATCCTGCGCGGGA

CGTCCTTTGTTTACGTCCCGTCGGCGCTGAATCCTGCGGACGACCCTTCTCGGGGTCGCTTGGG

ACTCTCTCGTCCCCTTCTCCGTCTGCCGTTCCGACCGACCACGGGGCGCACCTCTCTTTACGCG
```

Annex 1

```
GACTCCCCGTCTGTGCCTTCTCATCTGCCGGACCGTGTGCACTTCGCTTCACCTCTGCACGTCG

CATGGAGACCACCGTGAACGCCCACCAAATATTGCCCAAGGTCTTACATAAGAGGACTCTTGGA

CTCTCAGCAATGTCAACGACCGACCTTGAGGCATACTTCAAAGACTGTTTGTTTAAAGACTGGG

AGGAGTTGGGGGAGGAGATTAGGTTAAAGGTCTTTGTACTAGGAGGCTGTAGGCATAAATTGGT

CTGCGCACCAGCACCATGCAACTTTTTCACCTCTGCCTAATCATCTCTTGTTCATGTCCTACTG

TTCAAGCCTCCAAGCTGTGCCTTGGGTGGCTTTGGGGCATGGACATCGACCCTTATAAAGAATT

TGGAGCTACTGTGGAGTTACTCTCGTTTTTGCCTTCTGACTTCTTTCCTTCAGTAAGCTTCGAC
TACAAGGACGACGACGACAAGAGCCTGTTCAACACCGTGGCCACCCTGTACACCAAGGGCATCG
TGGGCTTCGTGTTCACCCTGAAGAACGCCGGCCTGTGCACCCTGGTGGCTATGCTGGGCCTGG
CCCCGGCAAGGCCAAGTTCGTGGCCGCCTGGACCCTGAAGGCTGCAGGGAACATGGAGCCCCT

ATCCTATCAACACTTCCGGAGACTACTGTTGTTAGACGACGAGGCAGGTCCCCTAGAAGAAGAA

CTCCCTCGCCTCGCAGACGAAGGTCTCAATCGCCGCGTCGCAGAAGATCTCAATCTCGGGAATC

TCAATGTTAGTATTCCTTGGACTCATAAGGTGGGGAACTTTACTGGGCTTTATTCTTCTACTGT

ACCTGTCTTTAATCCTCATTGGAAAACACCATCTTTTCCTAATATACATTTACACCAAGACATT

ATCAAAAAATGTGAACAGTTTGTAGGCCCACTCACAGTTAATGAGAAAAGAAGATTGCAATTGA

TTATGCCTGCCAGGTTTTATCCAAAGGTTACCAAATATTTACCATTGGATAAGGGTATTAAACC

TTATTATCCAGAACATCTAGTTAATCATTACTTCCAAACTAGACACTATTTACACACTCTATGG

AAGGCGGGTATATTATATAAGAGAGAAACAACACATAGCGCCTCATTTTGTGGGTCACCATATT

CTTGGGAACAAGATCTACAGCATGGGGCAGAATCTTTCCACCAGCAATCCTCTGGGATTCTTTC

CCGACCACCAGTTGGATCCAGCCTTCAGAGCAAACACCGCAAATCCAGATTGGGACTTCAATCC

CAACAAGGACACCTGGCCAGACGCCAACAAGGTAGGAGCTGGAGCATTCGGGCTGGGTTTCACC

CCACCGCACGGAGGCCTTTTGGGGTGGAGCCCTCAGGCTCAGGGCATACTACAAACTTTGCCAG

CAAATCCGCCTCCTGCCTCCACCAATCGCCAGTCAGGAAGGCAGCCTACCCCGCTGTCTCCACC

TTTGAGAAACACTCATCCTCAGGCCATGCAGTGGAATTCCACAACCTTCCACCAAACTCTGCAA

GATCCCAGAGTGAGAGGCCTGTATTTCCCTGCTGGTGGCTCCAGTTCAGGAACAGTAAACCCTG

TTCTGACTACTGCCTCTCCCTTATCGTCAATCTTCTCGAGGATTGGGGACCCTGCGCTGAACAT

GGAGAACATCACATCAGGATTCCTAGGACCCCTTCTCGTGTTACAGGCGGGGTTTTTCTTGTTG

ACAAGAATCCTCACAATACCGCAGAGTCTAGACTCGTGGTGGACTTCTCTCAATTTTCTAGGGG

GAACTACCGTGTGTCTTGGCCAAAATTCGCAGTCCCCAACCTCCAATCACTCACCAACCTCTTG

TCCTCCAACTTGTCCTGGTTATCGCTGGATGTGTCTGCGGCGTTTTATCATCTTCCTCTTCATC

CTGCTGCTATGCCTCATCTTCTTGTTGGTTCTTCTGGACTATCAAGGTATGTTGCCCGTTTGTC

CTCTAATTCCAGGATCCTCAACAACCAGCACGGGACCATGCCGGACCTGCATGACTACTGCTCA

AGGAACCTCTATGTATCCCTCCTGTTGCTGTACCAAACCTTCGGACGGAAATTGCACCTGTATT

CCCATCCCATCATCCTGGGCTTTCGGAAAATTCCTATGGGAGTGGGCCTCAGCCCGTTTCTCCT

GGCTCAGTTTACTAGTGCCATTTGTTCAGTGGTTCGTAGGGCTTTCCCCCACTGTTTGGCTTTC

AGTTATATGGATGATGTGGTATTGGGGGCCAAGTCTGTACAGCATCTTGAGTCCCTTTTTACCG

CTGTTACCAATTTTCTTTTGTCTTTGGGTATACATTTAAACCCTAACAAAACAAAGAGATGGGG

TTACTCTCTAAATTTTATGGGTTATGTCATTGGATGTTATGGGTCCTTGCCACAAGAACACATC

ATACAAAAAATCAAAGAATGTTTTAGAAAACTTCCTATTAACAGGCCTATTGATTGGAAAGTAT

GTCAACGAATTGTGGGTCTTTTGGGTTTTGCTGCCCCTTTTACACAATGTGGTTATCCTGCGTT

GATGCCTTTGTATGCATGTATTCAATCTAAGCAGGCTTTCACTTTCTCGCCAACTTACAAGGCC
```

Annex 1

```
TTTCTGTGTAAACAATACCTGAACCTTTACCCCGTTGCCCGGCAACGGCCAGGTCTGTGCCAAG

TGTTTGCTGACGCAACCCCCACTGGCTGGGGCTTGGTCATGGGCCATCAGCGCATGCGTGGAAC

CTTTTCGGCTCCTCTGCCGATCCATACTGCGGAACTCCTAGCCGCTTGTTTTGCTCGCAGCAGG

TCTGGAGCAAACATTATCGGGACTGATAACTCTGTTGTCCTATCCCGCAAATATACATCGTTTC

CATGGCTGCTAGGCTGTGCTGCCAACTGGATCCTGCGCGGGACGTCCTTTGTTTACGTCCCGTC

GGCGCTGAATCCTGCGGACGACCCTTCTCGGGGTCGCTTGGGACTCTCTCGTCCCCTTCTCCGT

CTGCCGTTCCGACCGACCACGGGGCGCACCTCTCTTTACGCGGACTCCCCGTCTGTGCCTTCTC

ATCTGCCGGACCGTGTGCACTTCGCTTCACCTCTGCACGTCGCATGGAGACCACCGTGAACGCC

CACCAAATATTGCCCAAGGTCTTACATAAGAGGACTCTTGGACTCTCAGCAATGTCAACGACCG

ACCTTGAGGCATACTTCAAAGACTGTTTGTTTAAAGACTGGGAGGAGTTGGGGGAGGAGATTAG

GTTAAAGGTCTTTGTACTAGGAGGCTGTAGGCATAAATTGGTCTGCGCACCAGCACCATGCAAC

TTTTTCACCTCTGCCTAATCATCTCTTGTTCATGTCCTACTGTTCAAGCCTCCAAGCTGTGCCT

TGGGTGGCTTTGGGGCATGGACATCGACCCTTATAAAGAATTTGGAGCTACTGTGGAGTTACTC

TCGTTTTTGCCTTCTGACTTCTTTCCTTCAGTACGAGATCCACTAGTTCTAGAGCGGCCGCCAC

CGCGGTGGAGCTCCAGCTTTTGTTCCCTTTAGTGAGGGTTAATTGCGCGCATGCCCGACGGCGA

GGATCTCGTCGTGACCCATGGCGATGCCTGCTTGCCGAATATCATGGTGGAAAATGGCCGCTTT

TCTGGATTCATCGACTGTGGCCGGCTGGGTGTGGCGGACCGCTATCAGGACATAGCGTTGGCTA

CCCGTGATATTGCTGAAGAGCTTGGCGGCGAATGGGCTGACCGCTTCCTCGTGCTTTACGGTAT

CGCCGCTCCCGATTCGCAGCGCATCGCCTTCTATCGCCTTCTTGACGAGTTCTTCTGAGCGGGA

CTCTGGGGTTCGAAATGACCGACCAAGCGACGCCCAACCTGCCATCACGAGATTTCGATTCCAC

CGCCGCCTTCTATGAAAGGTTGGGCTTCGGAATCGTTTTCCGGGACGCCGGCTGGATGATCCTC

CAGCGCGGGATCTCATGCTGGAGTTCTTCGCCCACCCCAACTTGTTTATTGCAGCTTATAATG

GTTACAAATAAAGCAATAGCATCACAAATTTCACAAATAAAGCATTTTTTTCACTGCATTCTAG

TTGTGGTTTGTCCAAACTCATCAATGTATCTTATCATGTCTGTATACCGTCGACCTCTAGCTAG

AGCTTGGCGTAATCATGGTCATAGCTGTTTCCTGTGTGAAATTGTTATCCGCTCACAATTCCAC

ACAACATACGAGCCGGAAGCATAAAGTGTAAAGCCTGGGGTGCCTAATGAGTGAGCTAACTCAC

ATTAATTGCGTTGCGCTCACTGCCCGCTTTCCAGTCGGGAAACCTGTCGTGCCAGCTGCATTAA

TGAATCGGCCAACGCGCGGGGAGAGGCGGTTTGCGTATTGGGCGCTCTTCCGCTTCCTCGCTCA

CTGACTCGCTGCGCTCGGTCGTTCGGCTGCGGCGAGCGGTATCAGCTCACTCAAAGGCGGTAAT

ACGGTTATCCACAGAATCAGGGGATAACGCAGGAAAGAACATGTGAGCAAAAGGCCAGCAAAAG

GCCAGGAACCGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCAATGCTCACGCTGTAGGTATCTCAGTT

CGGTGTAGGTCGTTCGCTCCAAGCTGGGCTGTGTGCACGAACCCCCCGTTCAGCCCGACCGCTG

CGCCTTATCCGGTAACTATCGTCTTGAGTCCAACCCGGTAAGACACGACTTATCGCCACTGGCA

GCAGCCACTGGTAACAGGATTAGCAGAGCGAGGTATGTAGGCGGTGCTACAGAGTTCTTGAAGT

GGTGGCCTAACTACGGCTACACTAGAAGGACAGTATTTGGTATCTGCGCTCTGCTGAAGCCAGT

TACCTTCGGAAAAAGAGTTGGTAGCTCTTGATCCGGCAAACAAACCACCGCTGGTAGCGGTGGT
```

Annex 1

```
TTTTTTGTTTGCAAGCAGCAGATTACGCGCAGAAAAAAGGATCTCAAGAAGATCCTTTGATCT

TTTCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAAGT

ATATATGAGTAAACTTGGTCTGACAGTTACCAATGCTTAATCAGTGAGGCACCTATCTCAGCGA

TCTGTCTATTTCGTTCATCCATAGTTGCCTGACTCCCCGTCGTGTAGATAACTACGATACGGGA

GGGCTTACCATCTGGCCCCAGTGCTGCAATGATACCGCGAGACCCACGCTCACCGGCTCCAGAT

TTATCAGCAATAAACCAGCCAGCCGGAAGGGCCGAGCGCAGAAGTGGTCCTGCAACTTTATCCG

CCTCCATCCAGTCTATTAATTGTTGCCGGGAAGCTAGAGTAAGTAGTTCGCCAGTTAATAGTTT

GCGCAACGTTGTTGCCATTGCTACAGGCATCGTGGTGTCACGCTCGTCGTTTGGTATGGCTTCA

TTCAGCTCCGGTTCCCAACGATCAAGGCGAGTTACATGATCCCCCATGTTGTGCAAAAAAGCGG

TTAGCTCCTTCGGTCCTCCGATCGTTGTCAGAAGTAAGTTGGCCGCAGTGTTATCACTCATGGT

TATGGCAGCACTGCATAATTCTCTTACTGTCATGCCATCCGTAAGATGCTTTTCTGTGACTGGT

GAGTACTCAACCAAGTCATTCTGAGAATAGTGTATGCGGCGACCGAGTTGCTCTTGCCCGGCGT

CAATACGGGATAATACCGCGCCACATAGCAGAACTTTAAAAGTGCTCATCATTGGAAAACGTTC

TTCGGGGCGAAAACTCTCAAGGATCTTACCGCTGTTGAGATCCAGTTCGATGTAACCCACTCGT

GCACCCAACTGATCTTCAGCATCTTTTACTTTCACCAGCGTTTCTGGGTGAGCAAAAACAGGAA

GGCAAAATGCCGCAAAAAAGGGAATAAGGGCGACACGGAAATGTTGAATACTCATACTCTTCCT

TTTTCAATATTATTGAAGCATTTATCAGGGTTATTGTCTCATGAGCGGATACATATTTGAATGT

ATTTAGAAAAATAAACAAATAGGGGTTCCGCGCACATTTCCCCGAAAAGTGCCACCTGACGTC
```

Sequence for rHBe_III_(the recombinant protein; polyepitope (polytope) sequence shadowed)

```
MDIDPYKEFGATVELLSFLPSDFFPSVSFDYKDDDDKSLENTYSILYTKGILGPVFTLOAGLC
                              ........AEHGAPILSTLPETTVVRRRGRSPRRRTPSPRRRRSQSPR
RRRSQSRESQC     (SEQ ID NO: 17)
```

Sequence for polytope III (amino acids in small letters are flanking residues)
DYkDDDDK▓▓▓▓▓▓▓▓ytk▓▓▓▓▓▓▓▓kna▓▓▓▓▓▓▓▓gpgpg▓▓▓▓▓▓▓▓
(SEQ ID NO: 18)

Sequence for polytope IV (amino acids in small letters are flanking residues)
DYkDDDDKelr▓▓▓▓▓▓▓▓ytk▓▓▓▓▓▓▓▓kna▓▓▓▓▓▓▓▓gpgpg▓▓▓▓▓▓▓▓
(SEQ ID NO: 19)

Annex 2

Sequence for prHBV-1.3-IV (polyepitope (polytope) sequence shadowed)

(SEQ ID NO: 20)
```
GACGGATCGGGAGATCTCCCGATCCCCTATGGTCGACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCAATCTAAGCAGGCTTTCACTTTCTCGCCAACTTACAAGGCCTTTCTG

TGTAAACAATACCTGAACCTTTACCCCGTTGCCCGGCAACGGCCAGGTCTGTGCCAAGTGTTTG

CTGACGCAACCCCCACTGGCTGGGGCTTGGTCATGGGCCATCAGCGCATGCGTGGAACCTTTTC
```

-continued

Annex 2

GGCTCCTCTGCCGATCCATACTGCGGAACTCCTAGCCGCTTGTTTTGCTCGCAGCAGGTCTGGA

GCAAACATTATCGGGACTGATAACTCTGTTGTCCTATCCCGCAAATATACATCGTTTCCATGGC

TGCTAGGCTGTGCTGCCAACTGGATCCTGCGCGGGACGTCCTTTGTTTACGTCCCGTCGGCGCT

GAATCCTGCGGACGACCCTTCTCGGGGTCGCTTGGGACTCTCTCGTCCCCTTCTCCGTCTGCCG

TTCCGACCGACCACGGGCGCACCTCTCTTTACGCGGACTCCCCGTCTGTGCCTTCTCATCTGC

CGGACCGTGTGCACTTCGCTTCACCTCTGCACGTCGCATGGAGACCACCGTGAACGCCCACCAA

ATATTGCCCAAGGTCTTACATAAGAGGACTCTTGGACTCTCAGCAATGTCAACGACCGACCTTG

AGGCATACTTCAAAGACTGTTTGTTTAAAGACTGGGAGGAGTTGGGGGAGGAGATTAGGTTAAA

GGTCTTTGTACTAGGAGGCTGTAGGCATAAATTGGTCTGCGCACCAGCACCATGCAACTTTTTC

ACCTCTGCCTAATCATCTCTTGTTCATGTCCTACTGTTCAAGCCTCCAAGCTGTGCCTTGGGTG

GCTTTGGGCATGGACATCGACCCTTATAAAGAATTTGGAGCTACTGTGGAGTTACTCTCGTTT

TTGCCTTCTGACTTCTTTCCTTCAGTAAGCTTCGACTACAAGGACGACGACGACAAGGAATTAA

GAAGGCTCTACAACACCGTGGCCACCCTCTACAACAAGGGCATCCTGGGCTTCGTCTTCACCCT

GAAGCAACGCCGCCCTGTGCACCCTGGTGCCCATGCTGAGCCCCGGCCCCGGCAAGGCCAAGTTC

GTGGCGGCTGAACTCTGAAGGCTGCAGCCGAACATGGAGCCCCTATCCTATCAACACTTCCGG

AGACTACTGTTGTTAGACGACGAGGCAGGTCCCCTAGAAGAAGAACTCCCTCGCCTCGCAGACG

AAGGTCTCAATCGCCGCGTCGCAGAAGATCTCAATCTCGGGAATCTCAATGTTAGTATTCCTTG

GACTCATAAGGTGGGGAACTTTACTGGGCTTTATTCTTCTACTGTACCTGTCTTTAATCCTCAT

TGGAAAACACCATCTTTTCCTAATATACATTTACACCAAGACATTATCAAAAAATGTGAACAGT

TTGTAGGCCCACTCACAGTTAATGAGAAAAGAAGATTGCAATTGATTATGCCTGCCAGGTTTTA

TCCAAAGGTTACCAAATATTTACCATTGGATAAGGGTATTAAACCTTATTATCCAGAACATCTA

GTTAATCATTACTTCCAAACTAGACACTATTTACACACTCTATGGAAGGCGGGTATATTATATA

AGAGAGAAACAACACATAGCGCCTCATTTTGTGGGTCACCATATTCTTGGGAACAAGATCTACA

GCATGGGCAGAATCTTTCCACCAGCAATCCTCTGGGATTCTTTCCCGACCACCAGTTGGATCC

AGCCTTCAGAGCAAACACCGCAAATCCAGATTGGGACTTCAATCCCAACAAGGACACCTGGCCA

GACGCCAACAAGGTAGGAGCTGGAGCATTCGGGCTGGGTTTCACCCCACCGCACGGAGGCCTTT

TGGGGTGGAGCCCTCAGGCTCAGGGCATACTACAAACTTTGCCAGCAAATCCGCCTCCTGCCTC

CACCAATCGCCAGTCAGGAAGGCAGCCTACCCCGCTGTCTCCACCTTTGAGAAACACTCATCCT

CAGGCCATGCAGTGGAATTCCACAACCTTCCACCAAACTCTGCAAGATCCCAGAGTGAGAGGCC

TGTATTTCCCTGCTGGTGGCTCCAGTTCAGGAACAGTAAACCCTGTTCTGACTACTGCCTCTCC

CTTATCGTCAATCTTCTCGAGGATTGGGGACCCTGCGCTGAACATGGAGAACATCACATCAGGA

TTCCTAGGACCCCTTCTCGTGTTACAGGCGGGGTTTTCTTGTTGACAAGAATCCTCACAATAC

CGCAGAGTCTAGACTCGTGGTGGACTTCTCTCAATTTTCTAGGGGGAACTACCGTGTGTCTTGG

CCAAAATTCGCAGTCCCCAACCTCCAATCACTCACCAACCTCTTGTCCTCCAACTTGTCCTGGT

TATCGCTGGATGTGTCTGCGGCGTTTTATCATCTTCCTCTTCATCCTGCTGCTATGCCTCATCT

TCTTGTTGGTTCTTCTGGACTATCAAGGTATGTTGCCCGTTTGTCCTCTAATTCCAGGATCCTC

AACAACCAGCACGGGACCATGCCGGACCTGCATGACTACTGCTCAAGGAACCTCTATGTATCCC

TCCTGTTGCTGTACCAAACCTTCGGACGGAAATTGCACCTGTATTCCCATCCCATCATCCTGGG

CTTTCGGAAAATTCCTATGGGAGTGGGCCTCAGCCCGTTTCTCCTGGCTCAGTTTACTAGTGCC

ATTTGTTCAGTGGTTCGTAGGGCTTTCCCCCACTGTTTGGCTTTCAGTTATATGGATGATGTGG

-continued

Annex 2

```
TATTGGGGGCCAAGTCTGTACAGCATCTTGAGTCCCTTTTTACCGCTGTTACCAATTTTCTTTT

GTCTTTGGGTATACATTTAAACCCTAACAAAACAAAGAGATGGGGTTACTCTCTAAATTTTATG

GGTTATGTCATTGGATGTTATGGGTCCTTGCCACAAGAACACATCATACAAAAAATCAAAGAAT

GTTTTAGAAAACTTCCTATTAACAGGCCTATTGATTGGAAAGTATGTCAACGAATTGTGGGTCT

TTTGGGTTTTGCTGCCCCTTTTACACAATGTGGTTATCCTGCGTTGATGCCTTTGTATGCATGT

ATTCAATCTAAGCAGGCTTTCACTTTCTCGCCAACTTACAAGGCCTTTCTGTGTAAACAATACC

TGAACCTTTACCCCGTTGCCCGGCAACGGCCAGGTCTGTGCCAAGTGTTTGCTGACGCAACCCC

CACTGGCTGGGGCTTGGTCATGGGCCATCAGCGCATGCGTGGAACCTTTTCGGCTCCTCTGCCG

ATCCATACTGCGGAACTCCTAGCCGCTTGTTTTGCTCGCAGCAGGTCTGGAGCAAACATTATCG

GGACTGATAACTCTGTTGTCCTATCCCGCAAATATACATCGTTTCCATGGCTGCTAGGCTGTGC

TGCCAACTGGATCCTGCGCGGGACGTCCTTTGTTTACGTCCCGTCGGCGCTGAATCCTGCGGAC

GACCCTTCTCGGGGTCGCTTGGGACTCTCTCGTCCCCTTCTCCGTCTGCCGTTCCGACCGACCA

CGGGGCGCACCTCTCTTTACGCGGACTCCCCGTCTGTGCCTTCTCATCTGCCGGACCGTGTGCA

CTTCGCTTCACCTCTGCACGTCGCATGGAGACCACCGTGAACGCCCACCAAATATTGCCCAAGG

TCTTACATAAGAGGACTCTTGGACTCTCAGCAATGTCAACGACCGACCTTGAGGCATACTTCAA

AGACTGTTTGTTTAAAGACTGGGAGGAGTTGGGGGAGGAGATTAGGTTAAAGGTCTTTGTACTA

GGAGGCTGTAGGCATAAATTGGTCTGCGCACCAGCACCATGCAACTTTTTCACCTCTGCCTAAT

CATCTCTTGTTCATGTCCTACTGTTCAAGCCTCCAAGCTGTGCCTTGGGTGGCTTTGGGGCATG

GACATCGACCCTTATAAAGAATTTGGAGCTACTGTGGAGTTACTCTCGTTTTTGCCTTCTGACT

TCTTTCCTTCAGTACGAGATCCACTAGTTCTAGAGCGGCCGCCACCGCGGTGGAGCTCCAGCTT

TTGTTCCCTTTAGTGAGGGTTAATTGCGCGCATGCCCGACGGCGAGGATCTCGTCGTGACCCAT

GGCGATGCCTGCTTGCCGAATATCATGGTGGAAAATGGCCGCTTTTCTGGATTCATCGACTGTG

GCCGGCTGGGTGTGGCGGACCGCTATCAGGACATAGCGTTGGCTACCCGTGATATTGCTGAAGA

GCTTGGCGGCGAATGGGCTGACCGCTTCCTCGTGCTTTACGGTATCGCCGCTCCCGATTCGCAG

CGCATCGCCTTCTATCGCCTTCTTGACGAGTTCTTCTGAGCGGGACTCTGGGGTTCGAAATGAC

CGACCAAGCGACGCCCAACCTGCCATCACGAGATTTCGATTCCACCGCCGCCTTCTATGAAAGG

TTGGGCTTCGGAATCGTTTTCCGGGACGCCGGCTGGATGATCCTCCAGCGCGGGGATCTCATGC

TGGAGTTCTTCGCCCACCCCAACTTGTTTATTGCAGCTTATAATGGTTACAAATAAAGCAATAG

CATCACAAATTTCACAAATAAAGCATTTTTTTCACTGCATTCTAGTTGTGGTTTGTCCAAACTC

ATCAATGTATCTTATCATGTCTGTATACCGTCGACCTCTAGCTAGAGCTTGGCGTAATCATGGT

CATAGCTGTTTCCTGTGTGAAATTGTTATCCGCTCACAATTCCACACAACATACGAGCCGGAAG

CATAAAGTGTAAAGCCTGGGGTGCCTAATGAGTGAGCTAACTCACATTAATTGCGTTGCGCTCA

CTGCCCGCTTTCCAGTCGGGAAACCTGTCGTGCCAGCTGCATTAATGAATCGGCCAACGCGCGG

GGAGAGGCGGTTTGCGTATTGGGCGCTCTTCCGCTTCCTCGCTCACTGACTCGCTGCGCTCGGT

CGTTCGGCTGCGGCGAGCGGTATCAGCTCACTCAAAGGCGGTAATACGGTTATCCACAGAATCA

GGGGATAACGCAGGAAAGAACATGTGAGCAAAAGGCCAGCAAAAGGCCAGGAACCGTAAAAAGG

CCGCGTTGCTGGCGTTTTTCCATAGGCTCCGCCCCCCTGACGAGCATCACAAAAATCGACGCTC

AAGTCAGAGGTGGCGAAACCCGACAGGACTATAAAGATACCAGGCGTTTCCCCCTGGAAGCTCC

CTCGTGCGCTCTCCTGTTCCGACCCTGCCGCTTACCGGATACCTGTCCGCCTTTCTCCCTTCGG
```

Annex 2

```
GAAGCGTGGCGCTTTCTCAATGCTCACGCTGTAGGTATCTCAGTTCGGTGTAGGTCGTTCGCTC
CAAGCTGGGCTGTGTGCACGAACCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCTTCGGAAAAGAGTT
GGTAGCTCTTGATCCGGCAAACAAACCACCGCTGGTAGCGGTGGTTTTTTTGTTTGCAAGCAGC
AGATTACGCGCAGAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCACC
TAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTCTATTAA
TTGTTGCCGGGAAGCTAGAGTAAGTAGTTCGCCAGTTAATAGTTTGCGCAACGTTGTTGCCATT
GCTACAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTCCTCC
GATCGTTGTCAGAAGTAAGTTGGCCGCAGTGTTATCACTCATGGTTATGGCAGCACTGCATAAT
TCTCTTACTGTCATGCCATCCGTAAGATGCTTTTCTGTGACTGGTGAGTACTCAACCAAGTCAT
TCTGAGAATAGTGTATGCGGCGACCGAGTTGCTCTTGCCCGGCGTCAATACGGGATAATACCGC
GCCACATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCGCAAAAA
GGGAATAAGGGCGACACGGAAATGTTGAATACTCATACTCTTCCTTTTTCAATATTATTGAAGC
ATTTATCAGGGTTATTGTCTCATGAGCGGATACATATTTGAATGTATTTAGAAAAATAAACAAA
TAGGGGTTCCGCGCACATTTCCCCGAAAAGTGCCACCTGACGTC
```

Sequence for rHBe_IV_(the recombinant protein; polyepitope (polytope) sequence shadowed)

MDIDPYKEFGATVELLSFLPSDFFPSVSF[shaded polytope sequence]EHGAPILSTLPETTVVRRRGRSPRRRTPSPRRRRSQ
SPRRRRSQSRESQC (SEQ ID NO: 21)

---

What is claimed is:

1. A recombinant replication defective hepatitis virus comprising, a hepatitis B ayw3 (HBV ayw3) virus genome defective for the expression of hepatitis virus capsid protein (HBc), wherein the virus contains a heterologous nucleotide sequence of up to about 195 nucleotides encoding at least one immunogenic epitope, wherein the heterologous nucleotide sequence is located between nucleotide residue 1981 and nucleotide residue 2308 of the HBV ayw3 genome, wherein the numbering starts from the fourth nucleotide in the EcoRI site of the HBV genome of SEQ ID NO:22.

2. A immunogenic composition comprising the recombinant replication defective virus of claim 1 and a pharmaceutically acceptable carrier.

3. A recombinant hepatitis pseudo-virus comprising the recombinant, replication defective hepatitis virus as claimed in claim 1 complemented by HBc, wherein the pseudo-virus replicates in vitro in human hepatocytes.

4. A cloning and/or expression vector comprising a recombinant replication defective, hepatitis virus as claimed in claim 1.

5. An isolated hepatocyte cell of a vertebrate infected by the recombinant, replication defective hepatitis virus as claimed in claim 1.

6. The isolated hepatocyte cell as claimed in claim 5, wherein the cell further comprises a nucleotide sequence encoding HBc for complementation of the recombinant hepatitis virus to form a hepatitis pseudo-virus.

7. An isolated hepatocyte cell of a vertebrate infected by the hepatitis pseudo-virus as claimed in claim 3.

8. An isolated eukaryotic host cell comprising a vector as claimed in claim 4.

9. A method of forming a hepatitis pseudo-virus, wherein the method comprises culturing the hepatocyte cell as claimed in claim 6 under conditions for expression of the nucleotide sequence encoding the HBc and complementation of the recombinant, replication defective hepatitis virus to form a hepatitis pseudo-virus.

10. A method of producing hepatitis pseudo-virus, wherein the method comprises:

providing a host cell as claimed in claim 8; and expressing the hepatitis proteins under conditions in which the proteins assemble into hepatitis pseudo-virus, which are released from the host cell into extracellular space.

11. A method as claimed in claim 10, which comprises recovering the hepatitis pseudo-virus.

12. A method of treating a patient chronically infected by a hepatitis virus, wherein the method comprises administering to the virus-infected patient a recombinant, replication defective, hepatitis virus as claimed in claim 1 in an amount sufficient to clear virus from hepatitis virus-infected hepatic cells of the patient.

13. A method for stimulating a T cell response against cells infected with a virus in a patient persistently infected with said virus, wherein said method comprises administering to said patient a composition according to claim 2.

14. A method for targeting the expression of an epitope in a cell infected with a virus wherein said method comprises providing to the cell the recombinant replication defective virus of claim 1.

15. The method according to claim 13, wherein the patient is infected with HBV.

* * * * *